United States Patent

Nishi et al.

[11] 4,298,739
[45] Nov. 3, 1981

[54] NOVEL CARBOSTYRIL DERIVATIVES

[75] Inventors: Takao Nishi; Hiraki Ueda; Kazuyuki Nakagawa, all of Tokushima, Japan

[73] Assignee: Otsuka Pharmaceutical Co., Ltd., Tokyo, Japan

[21] Appl. No.: 142,057

[22] Filed: Apr. 21, 1980

Related U.S. Application Data

[63] Continuation of Ser. No. 914,589, Jun. 9, 1978, abandoned.

[30] Foreign Application Priority Data

Jun. 10, 1977 [JP] Japan ............... 52/69319
Jun. 24, 1977 [JP] Japan ............... 52/75863
Feb. 28, 1978 [JP] Japan ............... 53/23012

[51] Int. Cl.³ .................. C07D 215/22; A61K 31/47
[52] U.S. Cl. ..................... 546/158; 546/157; 424/258
[58] Field of Search .................... 546/157, 158

[56] References Cited

U.S. PATENT DOCUMENTS

| | | | |
|---|---|---|---|
| 3,919,239 | 11/1975 | Nakagawa et al. | 424/258 |
| 3,953,456 | 4/1976 | Nakagawa et al. | 424/258 |
| 4,022,784 | 5/1977 | Nakagawa et al. | 424/258 |
| 4,070,470 | 1/1978 | Nakagawa et al. | 424/258 |

FOREIGN PATENT DOCUMENTS 49-101387 9/1974 Japan .................. 546/157
54-119478 9/1979 Japan .................. 546/158

*Primary Examiner*—Donald G. Daus
*Assistant Examiner*—Diana G. Rivers

*Attorney, Agent, or Firm*—Finnegan, Henderson, Farabow, Garrett & Dunner

[57] ABSTRACT

Novel carbostyril derivatives having platelet aggregation inhibitory action, antiinflamatory action, antiulcer action, vasodilatory action and phosphodiesterase inhibitory action and are useful for preventing or curing thrombus, arteriosclerosis, hypertension, asthma and other like diseases, and also useful as an antiinflamatory or anti-ulcer agent, represented by the formula

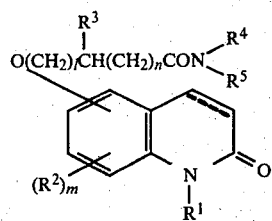

wherein $R^1$ is hydrogen, $C_{1-4}$ alkyl, $C_{2-4}$ alkenyl, phenyl-$C_{1-4}$ alkyl-; $R^2$ is hydrogen, a halogen atom, hydroxy, phenyl-$C_{1-4}$ alkoxy; $R^3$ is hydrogen, hydroxy, $C_{1-4}$ alkyl; $R^4$ is $C_{3-8}$ cycloalkyl, substituted or unsubstituted phenyl, $C_{3-8}$ cycloalkyl-$C_{1-4}$ alkyl, 2-(3,4-dimethoxyphenyl)-ethyl, $R^5$ is hydrogen, $C_{1-8}$ alkyl, $C_{2-4}$ alkenyl, phenyl, $C_{3-8}$ cycloalkyl, phenyl-$C_{1-4}$ alkyl, $C_{3-8}$ cycloalkyl-$C_{1-4}$ alkyl, m is an integer of 1 - 3, l and n which may be same or different, and are respectively 0 or an integer of 1 - 7 and the sum of l and n is not exceeding 7, the carbon-carbon bond at 3- and 4-positions in the carbostyril skelton is either single or double bond.

35 Claims, No Drawings

NOVEL CARBOSTYRIL DERIVATIVES

This is a continuation, of application Ser. No. 914,589, filed June 9, 1978, now abandoned.

The present invention relates to novel carbostyril derivatives.

The compounds provided according to the present invention are novel carbostyril derivatives and salts thereof represented by the following general formula:

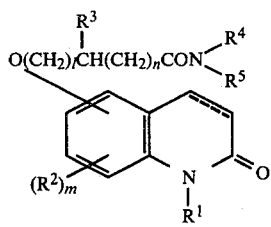

(1)

wherein $R^1$ is a hydrogen atom, an alkyl group having 1 to 4 carbon atoms, an alkenyl group having 2 to 4 carbon atoms or a phenylalkyl group formed from combination of a phenyl group and an a straight-chain or branched-chain alkylene group having 1 to 4 carbon atoms, $R^2$ is a hydrogen atom, a halogen atom, a hydroxy group or a phenylalkoxy group formed from combination of a phenyl group and an alkyleneoxy group having 1 to 4 carbon atoms, $R^3$ is a hydrogen atom, a hydroxy group or an alkyl group having 1 to 4 carbon atoms, $R^4$ is a substituted or unsubstituted cycloalkyl group having 3 to 8 carbon atoms, a substituted or unsubstituted phenyl group, a cycloalkylalkyl group formed from combination of a cycloalkyl group having 3 to 8 carbon atoms and an alkylene group having 1 to 4 carbon atoms, or 2-(3,4-dimethoxyphenyl)ethyl group, $R^5$ is a hydrogen atom, an alkyl group having 1 to 8 carbon atoms, an alkenyl group having 2 to 4 carbon atoms, a phenyl group, an unsubstituted cycloalkyl group having 3 to 8 carbon atoms, a phenylalkyl group formed from combination of a substituted or unsubstituted phenyl group and an alkylene group having 1 to 4 carbon atoms, or a cycloalkylalkyl group formed from combination of a cycloalkyl group having 3 to 8 carbon atoms and an alkylene group having 1 to 4 carbon atoms; m is an integer of 1 to 3, and l and n, which may be the same or different, and are respectively 0 or an integer of 1 to 7, and the sum of l and n is not exceeding 7; the carbon-carbon bond at 3- and 4-positions in the carbostyril skelton is either single or double bond.

The compounds of the present invention have a platelet aggregation inhibitory action, antiinflamatory action, antiuler action, vasodilatory action and phosphodiesterase (PDE) inhibitory action and are useful for preventing or curing thrombus, arteriosclerosis, hypertension, asthma and other like diseases, and also useful as an antiinflamatory or anti-ulcer agent.

In the general formula (1), as to the alkyl group having 1 to 4 carbon atoms represented by $R^1$ and $R^3$ may be more definitely specified as methyl group, ethyl group, propyl group, isopropyl group, butyl group, isobutyl group, sec-butyl group, tert-butyl group or the like. As to the alkyl group having 1 to 8 carbon atoms represented by $R^5$ may be more definitely specified as methyl group, ethyl group, propyl group, isopropyl group, butyl group, isobutyl group, sec-butyl group, tert-butyl group, pentyl group, isopentyl group, neopentyl group, 2-methylbutyl group, hexyl group, isohexyl group, 2-ethylbutyl group, heptyl group, 3-methylhexyl group or octyl group. As to the alkenyl group having 2 to 4 carbon atoms represented by $R^1$ and $R^5$ may be definitely specified as vinyl group, allyl group, isopropenyl group or 2-butenyl group. As to the phenylalkyl group represented by $R^1$ may be a phenylalkyl group formed from combination of a straight-chain or branched-chain alkylene group having 1 to 4 carbon atoms and a phenyl group, and examples of such phenylalkyl group are benzyl group, 2-phenylethyl group, 1-phenylethyl group, 3-phenylpropyl group, 4-phenylbutyl group and 1,1-dimethyl-2-phenylethyl group. The halogen atom represented by $R^2$ may be chlorine atom, bromine atom, iodine atom or fluorine atom. The phenylalkoxy group represented by $R^2$ may be the one formed from combination of the above-said phenylalkyl group and an oxygen atom, and examples of such phenylalkoxy group include benzyloxy group, 2-phenylethoxy group, 1-phenylethoxy group, 3-phenylpropoxy group, 4-phenylbutoxy group and 1,1-dimethyl-2-phenylethoxy group. The unsubstituted cycloalkyl group having 3 to 8 carbon atoms represented by $R^4$ and $R^5$ include, for example, cyclopropyl group, cyclobutyl group, cyclopentyl group, cyclohexyl group, cycloheptyl group and cyclooctyl group. The substituted cycloalkyl group having 3 to 8 carbon atoms represented by $R^4$ may be the above-said type of cycloalkyl group which has undergone substitution with one or two same or different substituents such as for example an alkyl group such as methyl, ethyl, propyl, isopropyl, butyl or tert-butyl group; an alkoxy group such as methoxy, ethoxy, propoxy, isopropoxy, butoxy or tert-butoxy group; a halogen atom such as chlorine atom, bromine atom, iodine atom or fluorine atom; an alkanoylamino group such as acetylamino, propionylamino, butyrylamino or isobutyrylamino group; an alkanoyloxy group such as acetyloxy, propionyloxy, butyryloxy or isoburyloxy group; an alkoxycarbonyl group such as methoxycarbonyl, ethoxycarbonyl, propoxycarbonyl, isopropoxycarbonyl or butoxycarbonyl group; an alkanoyl group such as acetyl, propionyl, butyryl or isobutyryl group; an alkylcarbamoyl group such as N-methylcarbamoyl, N-ethylcarbamoyl, N-propylcarbamoyl, N-isopropylcarbamoyl, N-butylcarbamoyl, N,N-diethylcarbamoyl or N-methyl-N-propylcarbamoyl group; an alkylamino group such as N,N-dimethylamino, N,N-diethylamino, N,N-dipropylamino, N-ethylamino, N-isopropylamino, N-methyl-N-ethylamino or N,N-dibutylamino group; a nitro group, a carboxy group, a hydroxyl group, an aminosulfonyl group, a carbamoyl group or an amino group. The substituted phenyl group represented by $R^4$ may be one which has undergone substitution with one or two substituent groups such as above-mentioned. The cycloalkylalkyl groups represented by $R^4$ and $R^5$ may be those formed from combination of a cycloalkyl group having 3 to 8 carbon atoms and a straight-chain or branched alkylene group having 1 to 4 carbon atoms, and as examples of such cycloalkylalkyl groups, one may cite the following: 4-cyclohexylbutyl group, 2-cyclopentylethyl group, cyclohexylmethyl group, 2-cyclopentylpropyl group, 3-cyclohexylpropyl group, cyclopentylmethyl group, 2-cyclohexylethyl group, 2-cyclohexylpropyl group, 2-cycloheptylethyl group, 3-cyclobutylpropyl group, 1,1-dimethyl-2-cyclohexylethyl group, and 1-methyl-2-cyclopentylethyl group. The substituted or unsubstituted phenylalkyl group represented by $R^5$, may be any of the above-mentioned phenylalkyl groups or those phenylalkyl groups which have, as substituent, one or two above-said alkoxy groups having 1 to 4 carbon atoms on the phenyl ring, and more definite examples of such phenylalkyl groups are 4-ethoxybenzyl, 2-(3,4-dimethoxyphenyl)ethyl, 1-(3,5-dimethoxyphenyl)ethyl, 3-(2-butoxyphenyl)propyl, 4-(3,4-dimethoxyphenyl)butyl and 1,1-dimethyl-2-(3,4-diethoxyphenyl)ethyl groups.

Listed below are the representative examples of the compounds provided according to this invention.

6-(N-Allyl-N-cyclopentylaminocarbonylmethoxy)-carbostyril
6-(N-Methyl-N-cycloheptylaminocarbonylmethoxy)-carbostyril
6-(N-Methylanilinocarbonylmethoxy)-3,4-dihydrocarbostyril
6-[2-(N-Ethyl-N-cyclooctylaminocarbonyl)-ethoxy]-carbostyril
6-[2-(N-Allyl-N-cycloheptylaminocarbonyl)-ethoxy]-3,4-dihydrocarbostyril
6-[3-(N-Cycloheptylaminocarbonyl)propoxy]-3,4-dihydrocarbostyril
6-[3-(N-Allyl-N-cyclohexylaminocarbonyl)-propoxy]-carbostyril
6-[3-(N-Methyl-N-cyclohexylaminocarbonyl)-propoxy]carbostyril
6-[3-(N-Ethyl-N-cyclohexylaminocarbonyl)-propoxy]-3,4-dihydrocarbostyril
6-[3-(N-Butyl-N-cyclooctylaminocarbonyl)-propoxy]-carbostyril
6-[3-(N-Methyl-N-cyclooctylaminocarbonyl)-propoxy]carbostyril
6-[3-(N-Butyl-N-cyclohexylaminocarbonyl)-propoxy]-carbostyril
6-[3-(o-Chloroanilinocarbonyl)propoxy]carbostyril
6-[3-(p-Methoxyanilinocarbonyl)propoxy]-3,4-dihydrocarbostyril
6-[3-(m-Hydroxyanilinocarbonyl)propoxy]carbostyril
6-[3-(N-Ethylanilinocarbonyl)propoxy]carbostyril
6-[3-(N,N-Diphenylaminocarbonyl)propoxy]carbostyril
6-[3-(N-Methyl-o-methylanilinocarbonyl)propoxy]-3,4-dihydrocarbostyril
6-[3-(N,N-Dicyclohexylaminocarbonyl)propoxy]-carbostyril
6-[3-(N-Cyclopentyl-N-cyclohexylaminocarbonyl)-propoxy]carbostyril
6-[3-(N-Cyclohexylanilinocarbonyl)propoxy]-3,4-dihydrocarbostyril
6-[4-(N-Ethyl-N-cyclohexylaminocarbonyl)-butoxy]-carbostyril
6-[4-(N-Methylanilinocarbonyl)butoxy]-3,4-dihydrocarbostyril
6-[4-(o,o-Dimethylanilinocarbonyl)butoxy]-carbostyril
6-[5-(N-Methyl-N-cyclohexylaminocarbonyl)-pentyloxy]carbostyril
6-[5-(N-Cyclohexylanilinocarbonyl)pentyloxy]-carbostyril
6-[6-(N-Methyl-N-cyclohexylaminocarbonyl)-hexyloxy]-3,4-dihydrocarbostyril
6-[6-(N-Ethylanilinocarbonyl)hexyloxy]carbostyril
5-(N-Methyl-N-cycloheptylaminocarbonylmethoxy)-3,4-dihydrocarbostyril
5-[2-(N-Methyl-N-cyclohexylaminocarbonyl)-ethoxy]-carbostyril
6-[8-(N-Ethyl-N-cyclohexylaminocarbonyl)-octyloxy]-carbostyril
5-[3-(N-Allyl-N-cyclopentylaminocarbonyl)-propoxy]-carbostyril
5-[3-(N-Methyl-N-cyclohexylaminocarbonyl)-propoxy]carbostyril
5-[3-(N-Propylanilinocarbonyl)propoxy]-carbostyril
5-[3-(N,N-Dicyclohexylaminocarbonyl)propoxy]-3,4-dihydrocarbostyril
5-[4-(N-Methyl-N-cyclohexylaminocarbonyl)-butoxy]-3,4-dihydrocarbostyril
5-[5-(N-Methyl-N-cyclohexylaminocarbonyl)-pentyloxy]carbostyril
7-[3-(N-Methyl-N-cyclohexylaminocarbonyl)-propoxy]carbostyril
7-[3-(N-Ethylanilinocarbonyl)propoxy]carbostyril
8-[3-(N-Ethyl-N-cyclohexylaminocarbonyl)-propoxy]-carbostyril
6-[3-(N-Octyl-N-cyclohexylaminocarbonyl)-propoxy]-carbostyril
5-[3-(N-Heptyl-N-cyclohexylaminocarbonyl)propoxy]-3,4-dihydrocarbostryil
6-{3-[N-Cyclohexyl-N-(2-phenylethyl)-aminocarbonyl]propoxy}carbostyril
5-(o-Chloro-p-nitroanilinocarbonylmethoxy)-3,4-dihydrocarbostyril
6-[3-(o-Carboxyanilinocarbonyl)propoxy]-carbostyril
6-[3-(N-Ethyl-p-aminosulfonylanilinocarbonyl)-propoxy]carbostyril
6-[3-(N-Methyl-o-carbamoylanilinocarbonyl)-propoxy]-3,4-dihydrocarbostyril
6-{3-[N-Methyl-N-(2-cyclohexylethyl)aminocarbonyl]propoxy}carbostyril
6-{3-[N-Phenyl-N-(2-cyclohexylethyl)aminocarbonyl]propoxy}carbostyril
6-{1-[o-(N-Methylcarbamoyl)anilinocarbonyl]-ethoxy}carbostyril
5-[1-(o-Carboxyanilinocarbonyl)ethoxy]-3,4-dihydrocarbostyril
1-Allyl-5-[1-(p-methoxyanilinocarbonyl)-ethoxy]-3,4-dihydrocarbostyril
1-Ethyl-6-[3-(N-methylanilinocarbonyl)-propoxy]carbostyril
1-Benzyl-6-[3-(N,N-diphenylaminocarbonyl)-propoxy]-carbostyril
6-[2-Methyl-3-(N-methyl-N-cyclohexylaminocarbonyl)propoxy]carbostyril
6-[2-Butyl-3-(N-allyl-N-cyclohexylaminocarbonyl)-propoxy]-3,4-dihydrocarbostyl
6-[4-Methyl-5-(N-propyl-N-cyclohexylaminocarbonyl)heptyloxy]carbostyril
5-[2-Methyl-3-(N-methyl-N-cyclohexylaminocarbonyl)propoxy]carbostyril
8-[2-Methyl-3-(N-ethyl-N-cyclohexylaminocarbonyl)propoxy]-3,4-dihydrocarbostyril
5-Chloro-6-[3-(N-ethyl-o-methylanilinocarbonyl)-propoxy]carbostyril
5-Fluoro-6-[3-(N-ethyl-N-cyclohexylaminocarbonyl)-propoxy]carbostyril
5-Chloro-6-[2-methyl-3-(N-methyl-N-cyclohexylaminocarbonyl)propoxy]-3,4-dihydrocarbostyril
5,6,7-Tribromo-8-[3-(N-methylanilinocarbonyl)-propoxy]-3,4-dihydrocarbostyril
5,6,7-Trichloro-8-[5-(N-ethyl-N-cyclohexylamino)pentyloxy]carbostyril
8-Bromo-5-[3-(N-methyl-N-cyclohexylaminocarbonyl)propoxy]carbostyril
8-Bromo-6-[2-methyl-3-(N-methyl-N-cyclohexylaminocarbonyl)propoxy]carbostyril 6,8-Dichloro-5-[3-(N-ethylanilinocarbonyl)-propoxy]-3,4-dihydrocarbostyril 5,7-Dichloro-6-[3-(N-methyl-N-cyclohexylaminocarbonyl)propoxy]carbostyril 5,7,8-Trichloro-6-[3-(N-methyl-N-cyclohexylaminocarbonyl)propoxy]carbostyril 8-Hydroxy-5-[3-(N-methyl-N-cyclohexylaminocarbonyl)propoxy]-3,4-dihydrocarbostyril 5-Benzyloxy-6-[3-(N-ethyl-N-cyclohexylaminocarbonyl)propoxy]carbostyril 7-Hydroxy-6-[3-(N-methyl-N-cyclohexylaminocarbonyl)propoxy]carbostyril 5,8-Dihydroxy-6-[3-(N-methyl-N-cyclohexylaminocarbonyl)propoxy]-3,4-dihydrocarbostyril 1-(4-Phenylbutyl)-5-[3-(N-ethyl-N-cyclopropylaminocarbonyl)propoxy]-3,4-dihydrocarbostyril 1-(2-Butenyl)-6-[3-(N-methyl-N-cyclohexylaminocarbonyl)propoxy]carbostyril 6,8-Dichloro-1-methyl-5-[4-(N-ethyl-N-cyclohexylaminocarbonyl)butoxy]carbostyril 8-Hydroxy-1-ethyl-5-[3-(N-methyl-N-cyclohexylaminocarbonyl)propoxy]carbostyril 1-Methyl-7-[2-methyl-3-(N-methyl-N-cyclohexylaminocarbonyl)propoxy]carbostyril 5-{1-[N-Ethyl-N-(3-methylcyclohexyl)aminocarbonyl]-propoxy}carbostyril 5-{3-[N-Methyl-N-(4-hydroxycyclohexyl)aminocarbonyl]propoxy}-3,4-dihydrocarbostyril 6-{3-[N-Methyl-N-(2-methylcyclohexyl)aminocarbonyl]propoxy}carbostyril 6-{3-[N-Methyl-N-(3-hydroxycyclohexyl)-aminocarbonyl]propoxy}carbostyril 6-[3-(N-4-Methoxycyclohexylaminocarbonyl)-propoxy]-3,4-dihydrocarbostyril 6-{3-[N-Methyl-N-(4-acetyloxycyclohexyl)-aminocarbonyl]propoxy}carbostyril 6-{2-Methyl-3-[N-methyl-N-(2-methylcyclohexyl)-aminocarbonyl]propoxy}-3,4-dihydrocarbostyril 1-Benzyl-6-[3-(N-4-ethoxycycloheptylaminocarbonyl)-propoxy]carbostyril 8-Hydroxy-5-{1-[N-methyl-N-(3-methylcyclohexyl)-aminocarbonyl]propoxy}carbostyril 5,6,8-Trichloro-6-{3-[N-methyl-N-(4-acetyloxycyclohexyl)aminocarbonyl]propoxy}-3,4-dihydrocarbostyril 6-{3-[N-Methyl-N-(2-hydroxy-5-methylcyclohexyl)-aminocarbonyl]propoxy}carbostyril 6-{3-[N-ethyl-N-(4-nitrocyclohexyl)aminocarbonyl]-propoxy}-3,4-dihydrocarbostyril 6-{3-[N-Methyl-N-(2-carboxycyclohexyl)aminocarbonyl]propoxy}carbostyril 6-{3-[N-Ethyl-N-(2-N-methylcarbamoylcyclohexyl)-aminocarbonyl]propoxy}carbostyril 5-{3-[N-Methyl-N-(2-N,N-diethylcarbamoylcyclohexyl)aminocarbonyl]propoxy}-3,4-dihydrocarbostyril 6-{3-[N-Ethyl-N-(2-carbamoylcyclohexyl)aminocarbonyl]propoxy}carbostyril 6-{3-[N-Methyl-N-(4-chlorocyclohexyl)aminocarbonyl]propoxy}carbostyril 6-{3-[N-Methyl-N-(3,4-dimethoxycyclohexyl)-aminocarbonyl]propoxy}carbostyril 6-{3-[N-Allyl-N-(4-aminosulfonylcyclohexyl)-aminocarbonyl]propoxy}-3,4-dihydrocarbostyril 6-{3-[N-Methyl-N-(3-acetylcyclohexyl)aminocarbonyl]propoxy}carbostyril 6-{3-[N-Methyl-N-(4-acetylaminocyclohexyl)-aminocarbonyl]propoxy}-3,4-dihydrocarbostyril 6-{3-[N-Methyl-N-(4-N,N-dimethylaminocyclohexyl)aminocarbonyl]propoxy}carbostyril 6-{3-[N-Methyl-N-(2,6-dimethylcyclohexyl)-aminocarbonyl]propoxy}carbostyril 6-{3-[N-ethyl-N-(2,5-dimethoxycyclohexyl)-aminocarbonyl]propoxy}-3,4-dihydrocarbostyril 6-{3-[N-Methyl-N-(2,5-dichlorocyclohexyl)-aminocarbonyl]propoxy}carbostyril 6-{3-[N-Cyclohexylmethyl-(2-chlorocyclohexyl)aminocarbonyl]propoxy}carbostyril 6-{3-[N-Methyl-N-(2-aminocyclohexyl)aminocarbonyl]propoxy}-3,4-dihydrocarbostyril 6-[2-Hydroxy-3-(N-methyl-N-cyclohexylaminocarbonyl)propoxy]carbostyril 5-[2-Hydroxy-3-(N-ethyl-p-methylanilinocarbonyl)-propoxy]-3,4-dihydrocarbostyril 6-[2-Hydroxy-3-(N-methylanilinocarbonyl)propoxy]-carbostyril 1-Ethyl-6-[2-hydroxy-3-(N-methyl-N-cyclohexylaminocarbonyl)propoxy]-3,4-dihydrocarbostyril 6-{3-[N-Methyl-N-(2-3',4'-dimethoxyphenylethyl)aminocarbonyl]propoxy}carbostyril 6-{3-[N-Allyl-N-(2-3',4'-dimethoxyphenylethyl)aminocarbonyl]propoxy}-3,4-dihydrocarbostyril 6-{3-[N-Benzyl-N-(2-3',4'-dimethoxyphenylethyl)-aminocarbonyl]propoxy}carbostyril 6-{3-[N-Phenyl-N-(2-3',4'-dimethoxyphenylethyl)-aminocarbonyl]propoxy}carbostyril 6-{3-[N-Cyclohexyl-N-(2-3',4'-dimethoxyphenylethyl)aminocarbonyl]propoxy}carbostyril 6-{2-Methyl-3-[N-ethyl-N-(2-3',4'-dimethoxyphenylethyl)aminocarbonyl]propoxy}carbostyril 5-Chloro-6-{3-[N-methyl-N-(2-3',4'-dimethoxyphenylethyl)aminocarbonyl]propoxy}carbostyril 1-Methyl-6-{3-[N-methyl-N-(2-3',4'-dimethoxyphenylethyl)aminocarbonyl]propoxy}-3,4-dihydrocarbostyril 8-Hydroxy-5-{3-[N-methyl-N-(2-3',4'-dimethoxyphenylethyl)aminocarbonyl]propoxy}carbostyril 6-{3-[N-Octyl-N-(2-methylcyclohexyl)aminocarbonyl]propoxy}carbostyril 6-{3-[N-Heptyl-N-(3-hydroxycyclohexyl)aminocarbonyl]propoxy}-3,4-dihydrocarbostyril 6-{3-[N-Octyl-N-(2-chlorocyclohexyl)aminocarbonyl]propoxy}carbostyril 6-[3-(N-Cyclohexyl-N-cyclohexylmethylaminocarbonyl)propoxy]carbostyril 6-{3-[N-(2-Cyclopentyl-1-methylethyl)aminocarbonyl]propoxy}carbostyril 6-{2-[N-(2-Cyclopentylethyl)aminocarbonyl]-ethoxy}-3,4-dihydrocarbostyril The compounds of this invention can be produced according to various processes such as for example expressed by the following reaction process formula-1 and reaction process formula-2:

Reaction process formula-1

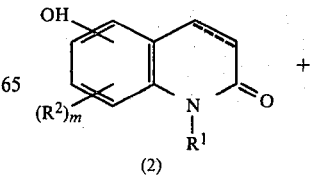

(2)

-continued

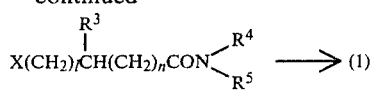
(3)

Reaction process formula-2

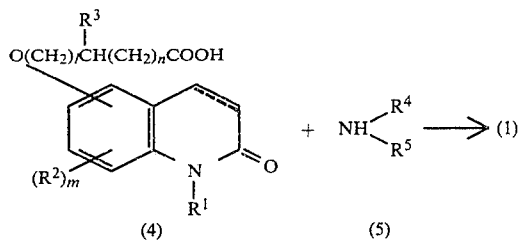

wherein X is a halogen atom, and $R^1$, $R^2$, $R^3$, $R^4$, $R^5$, m, l, n and carbon-carbon bond at 3- and 4-positions in the carbostyril skeleton are all same as defined above.

The starting materials used in this invention, that is, hydroxycarbostyril derivatives represented by the general formula (2), haloamide represented by the general formula (3), carboxyalkoxycarbostyril derivatives represented by the general formula (4) and amines represented by the general formula (5) may be all either known compounds or novel compounds and can be prepared according to the reaction process formulae $-5$ to $-11$ shown later.

The process expressed by the reaction process formula-1 is an ordinary method for carrying out a dehydrohalogenation reaction of a hydroxycarbostyril derivative represented by the general formula (2) with a haloamide represented by the general formula (3). The halogen atom in the haloamide may be bromine, chlorine or iodine atom. This dehydrohalogenation reaction is accomplished by using a basic compound as dehydrohalogenating agent. The basic compound used in said reaction may be selected from a wide variety of known basic compounds including inorganic bases such as sodium hydroxide, potassium hydroxide, sodium carbonate, potassium carbonate, sodium hydrogencarbonate, potassium hydrogencarbonate, silver carbonate, etc.; alkali metals such as sodium, potassium, etc.; alcoholates such as sodium methylate, sodium ethylate, etc.; and organic bases such as triethylamine, pyridine, N,N-dimethylaniline, etc. The above reaction can be carried out in the absence or presence of a solvent. The solvent used in this reaction may be of any known inert type which gives no adverse effect to the reaction. Among the examples of such solvent are alcohols such as methanol, ethanol, propanol, butanol, ethylene glycol, etc.; ethers such as diethyl ether, tetrahydrofuran, dioxane, monoglyme, diglyme, etc.; ketones such as acetone, methyl ethyl ketone, etc.; aromatic hydrocarbons such as benzene, toluene, xylene, etc.; esters such as methyl acetate, ethyl acetate, etc.; and aprotic polar solvents such as N,N-dimethylformamide, dimethylsulfoxide, hexamethylphosphoric triamide. It is advantageous to carry out the said reaction in the presence of a metallic iodide such as sodium iodide or potassium iodide. The ratio of amount of hydroxycarbostyril derivative (2) with haloamide (3) in the above method is not subject to any specific restriction and may be suitably selected from a wide range, but usually, it is desirable that the latter is used in equimolar to 5 times the molar quantity, preferably equimolar to double the molar quantity of the former. The reaction temperature is also not subject to any particular definition, but the reaction is usually carried out at room temperature to 200° C., preferably at 50° to 150° C. The reaction time is usually 1 to 30 hours, preferably 1 to 15 hours.

The process expressed by the reaction process formula-2 is a method for reacting a carboxyalkoxycarbostyril derivative represented by the general formula (4) with an amine represented by the general formula (5) according to an ordinary mode of amide bond forming reaction. The compound of the general formula (4) used in the invention may be substituted by a compound in which the carboxy groups were activated. It is also possible to use a compound having the activated amino groups in place of the amine represented by the general formula (5). The known amide bond forming reaction conditions may be easily applied to the practice of the amide bond forming reaction in this invention. For instance, the following methods are available for said reaction: (a) mixed acid anhydride method, thus on alkylhalocarboxylic acid is reacted with a carboxylic acid (4) to form a mixed acid anhydride and the latter is further reacted with an amine (5); (b) active ester method, thus a carboxylic acid (4) is converted into an active ester such as p-nitrophenyl ester, N-hydroxysuccinic acid imidoester, 1-hydroxybenzotriazole ester or the like and then such active ester is reacted with an amine (5); (c) carbodiimide method, thus an amine (5) is reacted with a carboxylic acid (4) in the presence of a dehydrating agent such as dicyclohexylcarbodiimide, carbonyldiimidazole, etc., to effect dehydration condensation; (d) other methods, thus a carboxylic acid (4) is converted into a carboxylic acid anhydride with a dehydrating agent such as acetic acid anhydride and then the carboxylic acid anhydride is reacted with an amine (5); high pressure and high temperature method, thus an amine (5) is reacted with an ester of a carboxylic acid (4) with a lower alcohol under a high pressure and high temperature condition; a method of reacting an amine (5) is reacted with an acid halide of a carboxylic acid (4), namely a carboxylic acid halide. Most preferrable method among these methods is mixed acid anhydride method. The alkylhalocarboxylic acid used in the mixed acid anhydride method may be for example methyl chloroformate, methyl bromoformate, ethyl chloroformate, ethyl bromoformate, isobutyl chloroformate or the like. The mixed acid anhydride may be obtained by an usual Schotten-Baumann reaction, and this substance, usually without isolation, is reacted with an amine (5) to produce the compound of the present invention. The Schotten-Baumann reaction is carried out in the presence of a basic compound. Such basic compound may be commonly used for the Schotten-Baumann reactions and may be for example an organic base such as triethylamine, trimethylamine, pyridine, N,N-dimethylaniline, N-methylmorpholine, etc.; or an inorganic base such as potassium carbonate, sodium carbonate, potassium hydrogencarbonate, sodium hydrogencarbonate, etc. Said reaction is usually carried out at a temperature within the range of $-20°$ to $100°$ C., preferably 0° to 50° C., for the period of 5 minutes to 10 hours, preferably 5 minutes to 2 hours. The reaction between the obtained mixed acid anhydride and an amine (5) is carried out at a temperature of $-20°$ to $150°$ C., preferably 10° to 50° C., for the period of 5 minutes to 10 hours, preferably 5 minutes to 5 hours. The mixed acid anhydride method is usually carried out in a solvent. Any type of solvent commonly used in the mixed acid anhydride method may be employed, for example halogenated hydrocarbons such as methylene chloride, chloroform, dichloroethane, etc.; aromatic hydrocarbons such as benzene, toluene, xylene, etc.; ethers such as diethyl ether, tetrahydrofuran, dimethoxyethane, etc.; esters such as methyl acetate, ethyl acetate, etc.; and aprotic polar solvents such as N,N-dimethylformamide (DMF), dimethylsulfoxide, hexamethylphosphoric acid triamide, etc. In this method, the carboxylic acid (4), alkylhalocarboxylic acid and amine (5) are usually used in the equimolar ratio to each other, but the alkylhalocarboxylic acid and amine (5) may be used in 1 to 1.5 times the molar quantity of the carboxylic acid (4).

The compounds of the invention can be also produced according to the processes expressed by the following reaction process formula-3 and reaction process formula-4. A compound of the general formula (1b) can be obtained by dehydrogenating a compound of the general formula (1a), while a compound of the general formula (1a) can be obtained by reducing a compound of the general formula (1b). A compound of the general formula (1d) can be produced from a dehydrohalogenation reaction of a compound of the general formula (1c) with a compound of the general formula (6).

Reaction process formula-3

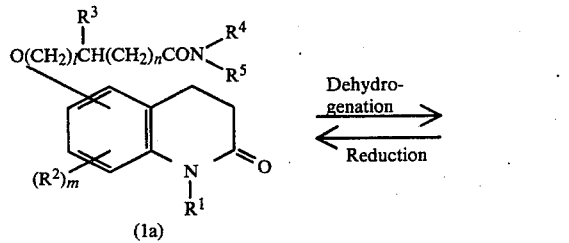

Reaction process formula-4

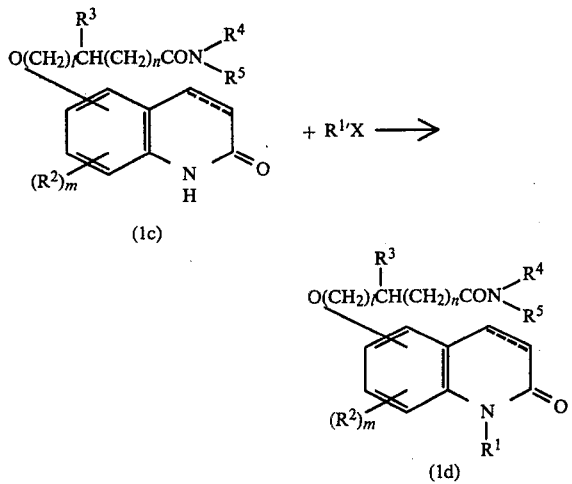

wherein $R^{1'}$ is an alkyl group with 1 to 4 carbon atoms, an alkenyl group with 2 to 4 carbon atoms or a phenylalkyl group, and $R^1$, $R^2$, $R^3$, $R^4$, $R^5$, m, l, n, X and carbon bond at 3- and 4-positions in the carbostyril skeleton are same as defined above. However, $R^2$ of the compound (1b) used as starting material for the reduction reaction in reaction process formula-3 is a hydrogen atom or a hydroxy group.

In reaction process formula-3, the dehydrogenation of a compound of the general formula (1a) can be accomplished according to an usual method by subjecting the compound to a dehydrogenation reaction in a suitable solvent by using an oxidizing agent. As to oxidizing agents which may be used in this reaction are, for example, benzoquinones such as 2,3-dichloro-5,6-dicyanobenzoquinone (hereinafter referred to as DDQ), chloranil (2,3,5,6-tetrachlorobenzoquinone), etc.; metallic catalysts such as selenium dioxide, palladium carbon, palladium black, platinum oxide, Raney nickel, etc.; and brominating agents such as N-bromosuccinimide, bromine, etc. As solvents which may be used in this reaction are, ethers such as dioxane, tetrahydrofuran, 2-methoxyethanol, dimethoxyethane, etc.; aromatic hydrocarbons such as benzene, toluene, xylene, etc.; halogenated hydrocarbons such as methylene chloride, dichloroethane, chloroform, carbon tetrachloride, etc.; alcohols such as butanol, amyl alcohol, hexanol, etc., and aprotic polar solvents such as N,N-dimethylformamide, dimethylsulfoxide, hexamethylphosphoric triamide, etc. This reaction is usually carried out at the temperature within the range of room temperature to 300° C., preferably 50° to 200° C., for the period of 1 hour to 2 days, preferably 1 to 20 hours. In case of using a benzoquinone or brominating agent as oxidating agent, it is usually used in an amount of 1 to 5 times, preferably 1 to 2 times the moles of compound (1a), and in case of using a metallic catalyst as oxidating agent, it may be used in an ordinary amount employed in an usual catalytic reaction.

In the reaction process formula-3, the catalytic reduction of the compound (1b) can be accomplished in the usual way by hydrogenating said compound in a suitable solvent by using a catalyst. Any known type of catalysts may be used for this reduction reaction. As examples thereof, one may cite platinum catalysts such as platinum wire, platinum plate, platinum sponge, platinum black, platinum oxide, colloidal platinum, etc.; palladium catalysts such as palladium sponge, palladium black, palladium oxide, palladium-barium sulfate, palladium-barium carbonate, palladium carbon, palladium silica gel, colloidal palladium, etc.; platinum group catalysts such as asbestos-filled rhodium, iridium, colloidal rhodium, ruthenium catalysts, colloidial iridium, etc., nickel catalysts such as reduced nickel, nickel oxide, Raney nickel, Urushibara nickel, nickel catalysts produced from thermal decomposition of nickel formate, nickel boride, etc.; cobalt catalysts such as reduced cobalt, Raney cobalt, Urushibara cobalt, etc; iron catalysts such as reduced iron, Raney iron, etc.; copper catalysts such as reduced copper, Raney copper, Ullmann copper, etc.; and other metallic catalysts such as zinc. The solvent used in the above reaction may be, for example, a lower alcohol (such as methanol, ethanol, isopropanol, etc.), water, acetic acid, an acetic acid ester (such as methyl acetate, ethyl acetate, etc.), ethylene glycol, an ether (such as diethyl ether, tetrahydrofuran, dioxane, etc.), an aromatic hydrocarbon (such as benzene, toluene, xylene, etc.), a cycloalkane (such as cyclopentane, cyclohexane, etc.), an n-alkane (such as n-hexane, n-pentane, etc.). The reaction is carried out under normal hydrogen pressure or under pressure, preferably under 1 to 20 atm., and at the temperature between room temperature and boiling point of the solvent, preferably between room temperature and 100° C.

In the reaction process formula-4, the reaction between the compound (1c) and the compound (6) is carried out by reacting the compound (1c) in the form of an alkali metal salt with the compound (6). The reaction for obtaining an alkali metal salt from the compound (1c) is conducted in the presence of an alkali metal compound. The alkali metal compound used here may be, for example, a metallic hydride such as sodium hydride, potassium hydride, etc.; an alkali metal such as metallic sodium, or sodium azide. This reaction is usually carried out in a solvent. Among the solvents usable in this reaction are aromatic hydrocarbon solvents such as benzene, toluene, xylene, etc.; ether solvents such as diethyl ether, 1,2-dimethoxyethylene, dioxane, etc.; and aprotic polar solvents such as dimethylformamide, dimethylsulfoxide, hexamethylphosphoric triamide, etc.; but the last-said aprotic polar solvents are most preferable. The alkali metal compound is usually used in an amount of 1 to 5 times, preferably 1 to 3 times the molar quantity of the compound (1c). The reaction temperature may be suitably selected from a wide range, usually 0° to 200° C., but the reaction advances most advantageously within the range of room temperature to 50° C. This reaction provides a compound (1c) where the nitrogen at 1-position has been substituted with an alkali metal. The reaction for obtaining the compound (1d) from an alkali metal salt of the above-obtained compound (1c) with the compound (6) is a condensation reaction. This condensation reaction may be accomplished easily in a usual way, but generally this reaction advances in a most preferred mode by reacting both compounds at room temperature in a solvent, for example, dimethylformamide. The amount of the compound (6) used may be suitably selected from a wide range, but usually it is desirably used in an amount of 1 to 5 times, most preferably 1 to 3 times the moles of the alkali metal salt of the compound (1c).

The process of the present invention is not limited to the above-described two-stage operation; it is of course possible to carry out the reaction by introducing the three compounds, that is, the compounds of the general formulae (1c) and (6) and said alkali metal compound simultaneously into the reaction system, and in this case, too, it is possible to obtain the compound of the present invention through the same course of reaction as said above.

Among the compounds represented by the general formula (2) used as the starting material in the present invention, the compound (2b) having a halogen atom as to R² can be easily obtained by halogenating the compound (2a) (known compound) which is among the compounds represented by the general formula (2) and which has a hydrogen atom as to R², as expressed by the following reaction process formula-5.

Reaction process formula-5

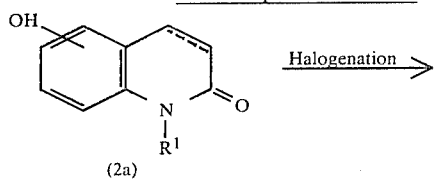

-continued
Reaction process formula-5

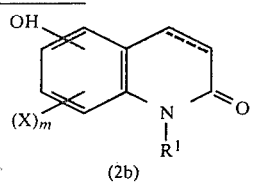

wherein X is a halogen atom, and R¹, m and carbon bond at 3- and 4-positions in the carbostyril skeleton are as defined above.

The halogenation reaction of the compound (2a) can be accomplished advantageously by using a known halogenating agent. Examples of such halogenating agent are fluorine, chlorine, bromine, iodine, xenon difluoride, sulfuryl chloride, sodium hypochlorite, hypochlorous acid, hypobromous acid, bleaching powder, etc. The amont of the halogenating agent may be suitably selected from a wide range in accordance with the number of the halogen atoms to be introduced into the compound (2a). In case of introducing one halogen atom, said halogenating agent is usually used in an amount of 1 to 2 times, preferably 1 to 1.5 times the molar quantity of the compound (2a), and in case of introducing two halogen atoms, said halogenating agent is used in an amount of 1.5 times the moles to large excess, preferably 2 to 3 times the moles of the compound (2a). In case of introducing three halogen atoms, said agent is used in an amount of 2.5 times the moles to large excess, preferably 3 to 5 times the moles of the compound (2a). Such halogenation reaction is usually conducted in a suitable solvent such as for example water, methanol, ethanol, chloroform, carbon tetrachloride, acetic acid or a mixture thereof. The reaction temperature is not subject to any particular definition and can be suitably selected from a wide range, but usually the reaction is carried out at the temperature of around −20° to 100° C., preferably 0° C. to room temperature. The reaction is completed within the period of about 30 minutes to 10 hours.

Among the compounds of the general formula (2b) used as starting material for the production of the compounds of this invention, the compound (2c) having the formula where m is 1 can be easily produced according to the process shown in the following reaction formula-6.

Reaction process formula-6

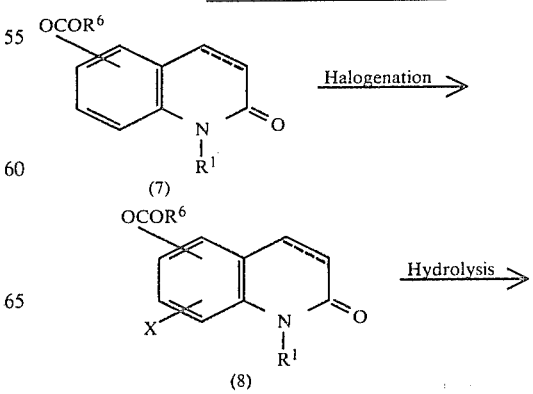

-continued
Reaction process formula-6

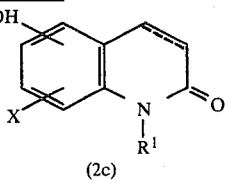

(2c)

wherein $R^6$ is an alkyl group, and $R^1$, X and carbon bond at 3- and 4-positions in the carbostyril skeleton are as defined above.

According to this process, a known acyloxycarbostyril derivative represented by the general formula (7) is halogenated and the obtained acyloxy-halogenocarbostyril derivative represented by the general formula (8) is hydrolyzed to produce a hydroxy-halogencarbostyril derivative represented by the general formula (2c). The halogenation reaction conditions are same as described above, and the hydrolysis reaction conditions may be same as described below.

Among the compounds represented by the general formula (4), those compounds which have a halogen atom, a hydroxy group or a phenylalkoxy group at the site of $R^2$ are novel compounds, and such compounds can be obtained from the process shown in the following reaction process formula-7.

Reaction process formula-7

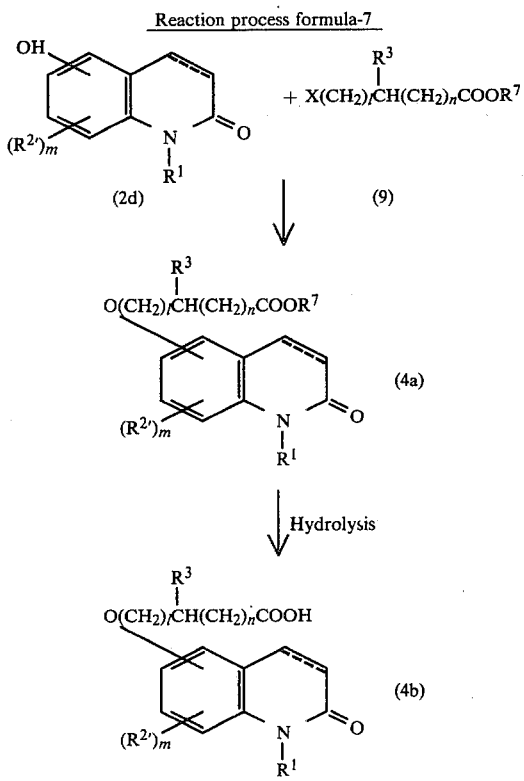

wherein $R^{2'}$ is a halogen atom, a hydroxy group or a phenylalkoxy group, $R^7$ is an organic residue, X is a halogen atom, and $R^1$, $R^3$, m, l, n and carbon bond at 3- and 4-positions in the carbostyril skeleton are as defined above.

According to this process, a hydroxycarbostyril derivative represented by the general formula (2d) is reacted with an ester derivative represented by the general formula (9) to obtain an ester carbostyril derivative represented by the general formula (4a), and the thus obtained compound of the general formula (4a) is hydrolyzed to produce a corresponding carboxyalkoxycarbostyril derivative represented by the general formula (4b).

The reaction between the compound (2d) and the compound (9) can be accomplished under the ordinary dehydrohalogenation reaction conditions. A variety of basic compounds may be used as the dehydrohalogenating agent in this reaction. Examples of such basic compounds include inorganic bases such as sodium hydroxide, potassium hydroxide, sodium carbonate, potassium carbonate, sodium hydrogencarbonate, potassium hydrogencarbonate, etc.; alkali metals such as sodium, potassium, etc.; and organic bases such as triethylamine, pyridine, N,N-dimethylaniline, etc. Such reaction can be conducted either in the presence or in the absence of a solvent. A variety of solvents that take no part in the reaction can be used. Recommended examples of such solvents for use in this reaction are alcohols such as methanol, ethanol, propanol, etc.; ethers such as diethyl ether, tetrahydrofuran, dioxane, ethylene glycol monomethyl ether, etc.; aromatic hydrocarbons such as benzene, toluene, xylene, chlorobenzene, etc.; and ketones such as acetone, methyl ethyl ketone, etc. The ratio of the amounts of compound (2d) to compound (9) is not subject to any specific limitations but can be suitably selected from a wide range. Usually, however, the latter is used in an amount of 1 to 5 times, preferably 1 to 2 times the moles of the former. The reaction temperature may be also suitably selected from a wide range, but usually the reaction is carried out at a temperature between room temperature and 200° C., preferably between 50° and 150° C., for the period of usually about 1 to 10 hours.

The hydrolysis reaction of the compound (4a) is usually conducted in the presence of a catalyst. The catalyst used may be of any type commonly employed for the hydrolysis reactions, and as typical examples of such catalyst, the following may be cited: basic compounds such as sodium hydroxide, potassium hydroxide, barium hydroxide, etc.; mineral acids such as sulfuric acid, hydrochloric acid, nitric acid, etc.; and organic acids such as acetic acid, aromatic sulfonic acid, etc. The amount of such catalyst used in the reaction is not defined to any specific extent but may be suitably selected from a wide range. Such hydrolysis reaction can be accomplished in an ordinary way but it proceeds advantageously in a solvent. It is possible to use a variety of solvents which take no part in the reaction, such as for example water, alcohols such as methanol, ethanol, isopropanol, etc.; ketones such as acetone, methyl ethyl ketone, or mixtures thereof. The reaction temperature is not critical and can be suitably selected from a wide range, but usually the reaction is practiced at a temperature between room temperature and 200° C., preferably between 50° and 150° C. The reaction is completed in usually about 5 minutes to 10 hours.

The amines of the general formula (5) used as the starting material in the present invention can be produced easily by various methods such as those expressed by the following reaction processes formulae-8, -9 and -10.

Reaction process formula-8

-continued

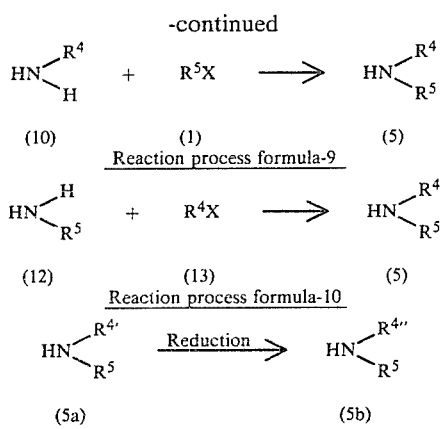

(10)     (1)     (5)

Reaction process formula-9

(12)     (13)     (5)

Reaction process formula-10

(5a)           (5b)

In the above formulae, $R^{4'}$ is a substituted or unsubstituted phenyl group or phenylalkyl group, $R^{4''}$ is a substituted or unsubstituted cyclohexyl or cyclohexylalkyl group, X is a halogen atom, and $R^4$ and $R^5$ are as defined above.

According to the reaction process formula-8, the amine represented by the general formula (5) can be easily obtained by subjecting a known amine of the general formula (10) and a known halogen compound of the general formula (11) to a dehydrohalogenation reaction in the presence of a basic compound. According to the reaction process formula-9, the amine represented by the general formula (5) can be produced by subjecting a known amine of the general formula (12) and a known halogen compound of the general formula (13) to a dehydrohalogenation reaction in the presence of a basic compound. These reactions can be simply accomplished similar to a dehydrohalogenation reaction between the compound of the general formula (2) and the compound of the general formula (3).

According to the reaction process formula-10, the cyclohexylamine derivative or cyclohexylalkylamine derivative represented by the general formula (5b) can be easily produced by reducing the benzene nucleus of a known compound of the general formula (5a). Various known nuclear hydrogenation reaction methods may be used for effecting the reduction of the benzene nucleus, but in the present invention, the catalytic reduction method is most advantageous. Such catalytic reduction is carried out in a solvent by using a catalyst according to a commonly employed method. The catalyst used in this reduction reaction may be of the type commonly employed for the nuclear hydrogenation reactions. Examples of such catalyst are platinum catalysts such as platinum black, platinum oxide, colloidal platinum, etc.; palladium catalysts such as palladium black, palladium carbon, colloidal palladium, etc.; rhodium catalysts such as asbestos-filled rhodium, rhodium alumina, etc.; ruthenium catalysts, nickel catalysts such as Raney nickel, nickel oxide, etc.; and cobalt catalysts. The solvent used in this reaction may be, for example, a lower alcohol (such as methanol, ethanol, isopropanol, etc.), water, acetic acid, acetic acid ester, ethylene glycol, an ether (tetrahydrofuran, dioxane, etc.) and a cycloalkane (such as cyclohexane, cyclopentane, etc.). This reaction is carried out under hydrogen pressure (preferably 1 to 100 atm.) at a temperature between room temperature and 100° C. for a period of 1 hour to 2 days.

The haloamides of the general formula (3) used as another starting material in the present invention can be obtained in various ways, for example, by reacting an amine of the general formula (5) and a known halocarboxylic acid of the general formula (14) as shown by the following reaction process formula-11.

Reaction process formula-11

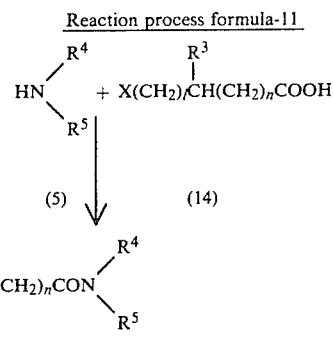

(5)        (14)

(3)

wherein $R^3$, $R^4$, $R^5$, l, n and X are all as defined above.

The reaction between the compound (5) and compound (14) can be accomplished in the same way as the above-said amide bond generating reaction. It is also possible in this invention to substitute the compound (14) with a compound having an activated carboxyl group.

Among the compounds of the present invention represented by the general formula (1), the compounds having a hydrogen as to $R^1$ and also having the double carbon-carbon bonds at 3- and 4-positions in the carbostyril skeleton may be prepared in the form of lactam-lactim type tautomeric compounds ((1e) and (1f)) as shown in the following reaction process formula-12.

Reaction process formula-12

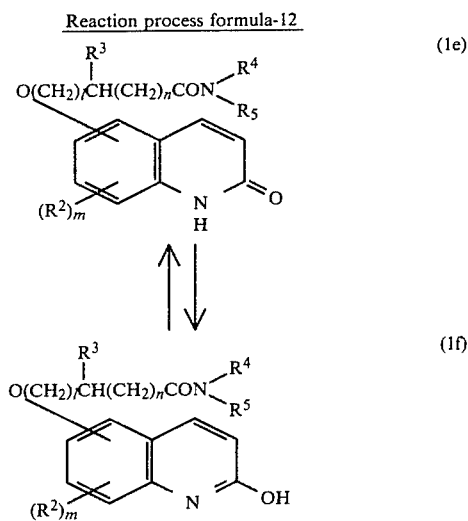

wherein $R^2$, $R^3$, $R^5$, m, l and n are as defined above.

Among the compounds represented by the general formula (1), those compounds which have an acidic group can easily form salts with the pharmaceutically acceptable basic compounds. Such basic compounds include the inorganic base compounds, for example metallic hydroxides such as sodium hydroxide, potassium hydroxide, lithium hydroxide, calcium hydroxide, barium hydroxide, aluminum hydroxide, etc.; metal carbonates such as sodium carbonate, potassium carbonate, potassium hydrogencarbonate, sodium hydrogencarbonate, etc.; alkali metal alcoholates such as sodium methylate, potassium ethylate, etc.; and alkali metals such as sodium, potassium, etc.; and the organic basic compounds such as morpholine, piperazine, piperidine, diethylamine, aniline, etc. Of the compounds represented by the general formula (1), those having a basic group can easily form salts with the usual pharmaceutically acceptable acids which include inorganic acids such as sulfuric acid, nitric acid, hydrochloric acid, hydrobromic acid, etc.; and organic acids such as acetic acid, p-toluenesulfonic acid, succinic acid, benzoic acid, etc.

The thus obtained compounds of the present invention can be easily isolated and refined by the usual separation means such as precipitation, extraction, recrystallization, column chromatography and preparative thin layer chromatography.

The compounds of the present invention can be administered, either in the form as they are or together with a pharmaceutically acceptable carrier, to animals as well as to human being. No particular restriction is placed on the administration unit forms and the compounds can be used in any desired unit form. Suitable administration unit forms include such oral administration forms as tablets, capsules, granules, etc.; and parenteral administration forms such as injections. The dosage of the active ingredient to be administered is not subject to any particular definition and admits of selection from a wide range, but in order to obtain a desired pharmacological effect, it is recommended to select said dosage from the range of 0.06 to 10 mg per kg body weight per day. It is also suggested to contain 1 to 500 mg of the active ingredient in each unit dose of the administration forms.

The compounds of the present invention can be formed into the desired peroral preparations such as tablets, capsules, solutions, etc., according to a common method. For preparation of tablets, a compound of the present invention is mixed with a pharmaceutically acceptable excipient such as gelatin, starch, lactose, magnesium stearate, talc, gum arabic or the like and shaped into tablets. Capsules can be obtained by mixing a compound of this invention with an inert pharmaceutically acceptable filler or diluent and filling the mixture into rigid gelatin capsules or soft capsules. Sirup or elixir may be prepared by mixing a compound of the present invention with a sweetening such as sucrose, antiseptic such as methyl- and propyl-parabens, colorant, seasoning and/or other suitable additives.

Parenteral preparations can be also obtained according to a common method. In this case, the compound of the present invention is dissolved in a sterilized liquid vehicle. Preferred vehicle is water or saline water. Liquid preparations having desired transparency, stability and parenteral use adaptability can be obtained by dissolving approximately 1 to 500 mg of the active ingredient in a solution of polyethylene glycol which is soluble in both water and organic solvents. Desirably, such liquid preparations contain a lubricant such as sodium carboxymethyl cellulose, methyl cellulose, polyvinyl pyrrolidone, polyvinyl alcohol or the like. Said liquid preparations may also contain a bactericide and fungicide such as benzyl alcohol, phenol or thimerosal and, if necessary, an isotonic agent such as sucrose or sodium chloride, a local anesthetic, stabilizer, buffer, etc. For additional ensurance of stability, the parenteral compositions may be freezed after filling and dehydrated by the known freeze-drying techniques. The freeze-dried powder can be returned to the normal use form just before use.

PREPARATION OF TABLETS 1,000 Tablets for peroral use, each containing 5 mg of 6-[3-(N-methyl-N-cyclohexylaminocarbonyl)propoxy]carbostyril, are prepared from the following prescription.

| Ingredient | Amount (g) |
| --- | --- |
| 6-[3-(N-Methyl-N-cyclohexylaminocarbonyl)propoxy]carbostyril | 5 |
| Lactose (J.P. = Japanese Pharmacopoeia) | 50 |
| Corn starch (J.P.) | 25 |
| Crystalline cellulose (J.P.) | 25 |
| Methyl cellulose (J.P.) | 1.5 |
| Magnesium stearate (J.P.) | 1 |

The above specified 6-[3-(N-methyl-N-cyclohexylaminocarbonyl)propoxy]carbostyril, lactose, corn starch and crystalline cellulose are mixed well, and the mixture is added with a 5% aqueous solution of methyl cellulose and then granulated. The obtained granules are passed through a 200 mesh sieve and then dried carefully.

PREPARATION OF TABLETS 1,000 Tablets for peroral use, each containing 5 mg of 6-{3-[N-methyl-N-(4-acetoxycyclohexyl)aminocarbonyl]propoxy}carbostyril, are preared in the similar way from the following prescription.

| Ingredient | Amount (g) |
| --- | --- |
| 6-{3-[N-Methyl-N-(4-acetoxycyclohexyl)aminocarboxyl]propoxy}carbostyril | 5 |
| Lactose (J.P.) | 50 |
| Corn starch (J.P.) | 25 |
| Crystalline cellulose (J.P.) | 25 |
| Methyl cellulose (J.P.) | 1.5 |
| Magnesium stearate (J.P.) | 1 |

PREPARATION OF CAPSULES 1,000 Pieces of two-piece rigid gelation capsules for peroral use, each containing 10 mg of 6-[3-(N-methyl-N-cyclohexylaminocarbonyl)propoxy]carbostyril, are prepared from the following prescription.

| Ingredient | Amount (g) |
| --- | --- |
| 6-[3-(N-Methyl-N-cyclohexylaminocarbonyl)propoxy]carbostyril | 10 |
| Lactose (J.P.) | 80 |
| Starch (J.P.) | 30 |
| Talc (J.P.) | 5 |
| Magnesium stearate (J.P.) | 1 |

The above components are finely ground, then stirred and mixed sufficiently to form a uniform mixture and then filled into the gelatin capsules with a size convenient for peroral administration.

PREPARATION OF CAPSULES 1,000 Pieces of two-piece rigid gelatin capsules for peroral use, each containing 10 mg of 6-{3-[N-methyl-N-(4-acetoxycyclohexyl)aminocarbonyl]propoxy}carbostyril, are prepared in the similar way from the following prescription.

| Ingredient | Amount (g) |
| --- | --- |
| 6-{3-[N-Methyl-N-(4-acetoxy-cyclohexyl)aminocarbonyl]-propoxy}carbostyril | 10 |
| Lactose (J.P.) | 80 |
| Starch (J.P.) | 30 |
| Talc (J.P.) | 5 |
| Magnesium stearate (J.P.) | 1 |

PREPARATION OF INJECTIONS

A sterile aqueous solution suited for parenteral use is prepared from the following prescription.

| Ingredient | Amount (g) |
| --- | --- |
| 6-[3-(N-Methyl-N-cyclohexyl-aminocarbonyl)propoxy]carbostyril | 1 |
| Polyethylene glycol (J.P.), [molecular weight: 4,000] | 0.3 |
| Sodium chloride (J.P.) | 0.9 |
| Polyoxyethylene sorbitan monooleate (J.P.) | 0.4 |
| Sodium metabisulfite | 0.1 |
| Methyl-p-hydroxybenzoate (J.P.) | 0.18 |
| Propyl p-hydroxybenzoate (J.P.) | 0.02 |
| Distilled water for injection | 100 ml |

A mixture of the above-prescribed methyl p-hydroxybenzoate, propyl p-hydroxybenzoate, sodium metabisulfite and sodium chloride, while stirred, is dissolved in about half the quantity of distilled water at 80° C. The obtained solution is cooled to 40° C., and then 6-[3-(N-methyl-N-cyclohexylaminocarbonyl)propoxy]carbostyril, polyethylene glycol and polyoxyethylene sorbitan monooleate are dissolved in that order in said solution. This solution is further added with distilled water for injection to the final regulated volume and then sterilized by sterile filtration with a suitable filter paper.

PREPARATION OF INJECTIONS

A sterile aqueous solution suited for parenteral use is prepared in the way similar to the above from the following prescription.

| Ingredient | Amount (g) |
| --- | --- |
| 6-{3-[N-Methyl-N-(4-acetoxycyclohexyl)aminocarbonyl]propoxy}-carbostyril | 1 |
| Polyethylene glycol (J.P.) [molecular weight: 4,000] | 0.3 |
| Sodium chloride (J.P.) | 0.9 |
| Polyoxyethylene sorbitan monooleate (J.P.) | 0.4 |
| Sodium metabisulfite | 0.1 |
| Methyl p-hydroxybenzoate (J.P.) | 0.18 |
| Propyl p-hydroxybenzoate (J.P.) | 0.02 |
| Distilled water for injection | 100 ml |

The results of the pharmacological tests on the compounds of this invention are shown below.

PHARMACOLOGICAL TEST 1

The platelet aggregation inhibitory effect is measured by using AG-II Aggregometer (manufactured by Bryston Manufacturing Co.). The blood sample used for the test is a 1/9 (by volume) mixture of sodium citrate and whole blood collected from rabbit. Said sample is subjected to 10-minute centrifugal separation at 1,000 r.p.m. to obtain a platelet rich plasma (PRP). The thus obtained PRP is separated, and the remaining blood sample is further subjected to 15-minute centrifugal separation at 3,000 r.p.m. to obtain a platelet poor plasma (PPP).

The number of platelets in the PRP is counted by the Brecher-Clonkite Method, and the PRP is diluted with the PPP to prepare a PRP sample with platelet concentration of 300,000/mm$^3$ for the adenosine diphosphate (ADP)-induced aggregation test. There is also prepared a PRP sample with platelet concentration of 450,000/mm$^3$ for the collagen-induced aggregation test.

0.6 ml of said PRP sample is added into 0.01 ml of a solution of a test compound of a predetermined concentration and the mixture is placed in a 37° C. thermostat for one minute. Then 0.07 ml of an ADP or collagen solution is added to the mixture. Transmittance of this mixture is determined and the change of transmittance is recorded by using the aggregometer at stirrer speed of 1,100 r.p.m. In this test, Auren Beronal buffer (pH 7.35) is used for the preparation of the ADP or collagen solution. ADP is adjusted to a concentration of $7.5 \times 10^{-5}$ M, and the collagen solution is prepared by triturating 100 mg of collagen with 5 ml of said buffer and the supernatant is used as collagen inducer. Adenosine and acetylsalicylic acid are used as controls for the ADP-induced aggregation test and the collagen-induced aggregation test, respectively. The platelet aggregation inhibitory effect is measured in terms of percent inhibition with respect to the aggregation rate of the controls. The aggregation rate is calculated from the following formula:

$$\text{Aggregation rate} = (c-a)/(b-a) \times 100$$

wherein
a: transmittance of PRP
b: transmittance of PRP containing a test compound and an aggregation inducer
c: transmittance of PPP.

The inhibitory effect of the tested compounds on collagen-induced aggregation in rabbit platelets is shown in Table 1, and such effect on ADP-induced aggregation is shown in Table 2. The compounds tested are as follows.

TESTED COMPOUNDS

COMPOUNDS OF THE PRESENT INVENTION (NOS. 1–24)

| No. | |
| --- | --- |
| 1. | 6-{3-[N-Methyl-N-(2-methylcyclohexyl)aminocarbonyl]propoxy}carbostyril |
| 2. | 6-{3-[N-Methyl-N-(4-hydroxycyclohexyl)aminocarbonyl]propoxy}carbostyril |
| 3. | 6-{3-[N-Methyl-N-(4-acetyloxycyclohexyl)aminocarbonyl]propoxy}carbostyril |
| 4. | 6-{3-[N-Methyl-N-(2-3',4'-dimethoxyphenylethyl)aminocarbonyl]propoxy}carbostyril |
| 5. | 6-{3-(N-Cyclohexyl-N-benzylaminocarbonyl)propoxy]carbostyril |
| 6. | 5-Chloro-6-[3-(N-methyl-N-cyclohexylaminocarbonyl)propoxy]carbostyril |
| 7. | 6-{3-[N-Cyclohexyl-N-(2-chlorocyclohexyl)aminocarbonyl]propoxy}-3,4-dihydrocarbostyril |
| 8. | 6-[2-Hydroxy-3-(N-methyl-N-cyclohexylaminocarbonyl)propoxy]carbostyril |
| 9. | 6-[3-(N-Methyl-N-cyclohexylaminocarbonyl)-2-methylpropoxy]carbostyril |
| 10. | 8-Hydroxy-5-[3-(N-Methyl-N-cyclohexylaminocarbonyl)propoxy]-3,4-dihydrocarbostyril |
| 11. | 6-{3-[N-Benzyl-N-(2-3',4'-dimethoxyphenylethyl)- |

-continued

| No. | |
|---|---|
| | aminocarbonyl]propoxy}-3,4-dihydrocarbostyril |
| 12. | 6,8-Dichloro-5-[3-(N-ethylanilinocarbonyl)-propoxy]-3,4-dihydrocarbostyril |
| 13. | 6-[3-(N-Cyclohexylaminocarbonyl)propoxy]carbostyril |
| 14. | 6-[3-(N-Allyl-N-cyclohexylaminocarbonyl)propoxy]-3,4-dihydrocarbostyril |
| 15. | 6-[3-(N-Methyl-N-cyclohexylaminocarbonyl)propoxy]-3,4-dihydrocarbostyril |
| 16. | 6-[3-(N-Methyl-N-cyclohexylaminocarbonyl)propoxy]-carbostyril |
| 17. | 6-[3-(N-Cyclohexylanilinocarbonyl)propoxy]carbostyril |
| 18. | 6-[3-(N,N-Dicyclohexylaminocarbonyl)propoxy]-3,4-dihydrocarbostyril |
| 19. | 6-[3-(Anilinocarbonyl)propoxy]-3,4-dihydrocarbostyril |
| 20. | 6-[3-(N-Ethylanilinocarbonyl)propoxy]carbostyril |
| 21. | 6-[3-(o,o-Dichloroanilinocarbonyl)propoxy]-3,4-dihydrocarbonstyril |
| 22. | 6-[4-(N-Butyl-N-cyclohexylaminocarbonyl)-buthoxy]-3,4-dihydrocarbostyril |
| 23. | 5-[3-(N-Methyl-N-cyclohexylaminocarbonyl)propoxy]-3,4-dihydrocarbostyril |
| 24. | 6-[3-(N,N-Diphenylaminocarbonyl)propoxy]-3,4-dihydrocarbostyril |

KNOWN COMPOUNDS (COMPARATIVE COMPOUNDS) (NOS. 25-46)

| No. | |
|---|---|
| 25. | 6-(1-Ethoxycarbonylethoxy)-3,4-dihydrocarbostyril |
| 26. | 6-(1-Ethoxycarbonylethoxy)carostyril |
| 27. | 1-Methyl-6-(1-ethoxycarbonylethoxy)-3,4-dihydrocarbostyril |
| 28. | 7-(1-ethoxycarbonylethoxy)-3,4-dihydrocarbostyril |
| 29. | 6-(3-Ethoxycarbonylpropoxy)-3,4-dihydrocarbostyril |
| 30. | 6-(1-Amyloxycarbonylethoxy)-3,4-dihydrocarbostyril |
| 31. | 6-(1-Isopropoxycarbonylethoxy)carbostyril |
| 32. | 5-(3-Ethoxycarbonylpropoxy)-3,4-dihydrocarbostyril |
| 33. | 6-(3-Amyloxycarbonylpropoxy)-3,4-dihydrocarbostyril |
| 34. | 6-(3-Ethoxycarbonylpropoxy)carbostyril |
| 35. | 6-(6-Ethoxycarbonylhexyloxy)-3,4-dihydrocarbostyril |
| 36. | 6-(6-Carboxyhexyloxy)-3,4-dihydrocarbostyril |
| 37. | 8-(1-Ethoxycarbonylethoxy)-3,4-dihydrocarbostyril |
| 38. | 6-(1-Methyl-1-carboxyethoxy)-3,4-dihydrocarbostyril |
| 39. | 6-(3-Carboxypropoxy)carbostyril |
| 40. | 6-(3-Cyclohexyloxycarbonylpropoxy)-3,4-dihydrocarbostyril |
| 41. | 5-(N-Isopropylaminocarbonylethoxy)-3,4-dihydrocarbostyril |
| 42. | 5-(Morpholinocarbonylmethoxy)-3,4-dihydrocarbostyril |
| 43. | 5-(N,N-dimethylaminocarbonylmethoxy)-3,4-dihydrocarbostyril |
| 44. | 1-Ethyl-5-[3-(N-benzylaminocarbonyl)propoxy]-3,4-dihydrocarbostyril |
| 45. | 6-[3-(N-Propylaminocarbonyl)-2-methylpropoxy]-3,4-dihydrocarbostyril |
| 46. | Aspirin |

TABLE 1

Inhibition effect of carbostyril derivatives on collagen induced aggregation in rabbit platelet

| | Test compound No. | Concentration of the test compound solution | | | |
|---|---|---|---|---|---|
| | | $10^{-4}$ mole | $10^{-5}$ mole | $10^{-6}$ mole | $10^{-7}$ mole |
| Compounds of the present invention | 1 | —% | 100.0% | 100.0% | 21.1% |
| | 2 | — | 100.0 | 89.7 | — |
| | 3 | 90.8 | 84.8 | 61.9 | — |
| | 4 | 82.9 | 46.5 | 19.2 | — |
| | 5 | — | 91.8 | 88.4 | 30.6 |
| | 6 | 100.0 | 53.3 | 12.3 | — |
| | 7 | 91.5 | 89.9 | 50.3 | — |
| | 8 | 85.5 | 86.8 | 2.9 | — |
| | 9 | 100.0 | 100.0 | 100.0 | 11.2 |
| | 10 | 91.8 | 29.3 | — | — |
| | 11 | 88.1 | 75.8 | 28.1 | — |
| | 12 | 82.6 | 65.2 | 33.8 | — |
| | 13 | 87.5 | 45.8 | 23.3 | — |
| | 14 | 82.4 | 42.3 | 15.7 | — |
| | 15 | 94.0 | 92.6 | 34.1 | — |
| | 16 | — | 90.5 | 90.2 | 57.0 |
| | 17 | 91.5 | 53.8 | 16.7 | — |
| | 18 | 87.5 | 59.4 | 50.0 | — |
| | 19 | 93.8 | 17.4 | — | — |
| | 20 | 91.3 | 76.3 | 43.2 | — |
| | 21 | 95.1 | 27.6 | — | — |
| | 22 | 85.6 | 78.5 | 28.7 | — |
| | 23 | 76.5 | 58.7 | 13.5 | — |
| | 24 | 82.7 | 43.5 | 15.5 | — |
| Known compounds (Reference compounds) | 25 | 71 | 20 | 2 | — |
| | 26 | 67 | 12 | −6 | — |
| | 27 | 36 | — | 0 | — |
| | 28 | 2 | — | 8 | — |
| | 29 | 92 | 38 | 8 | — |
| | 30 | 88 | 8 | 0 | — |
| | 31 | 55 | 25 | 3 | — |
| | 32 | 90 | 8 | 5 | — |
| | 33 | 48 | 22 | 6 | — |
| | 34 | 100 | 86 | 18 | — |
| | 35 | 31 | 13 | 6 | — |
| | 36 | 15 | 14 | 2 | — |
| | 37 | 5 | — | 2 | — |
| | 38 | 5 | 3 | 0 | — |
| | 39 | 28 | 15 | 0 | — |
| | 40 | 12 | 8 | 0 | — |
| | 41 | 17 | — | 0 | — |
| | 42 | 5 | 0 | 0 | — |
| | 43 | 27 | 13 | 0 | — |
| | 44 | 7 | 0 | 0 | — |
| | 45 | 12 | 5 | 0 | — |
| | 46 | 65 | 9 | 7 | — |

TABLE 2

Inhibition effect of carbostyril derivatives on ADP-induced aggregation in rabbit platelet

| | Test compound No. | Concentration of the test compound solution | | | |
|---|---|---|---|---|---|
| | | $10^{-4}$ mole | $10^{-5}$ mole | $10^{-6}$ mole | $10^{-7}$ mole |
| Compounds of the present invention | 1 | 100.0% | 73.0% | 42.4% | 4.3% |
| | 2 | — | 90.3 | 54.3 | — |
| | 3 | 91.5 | 75.0 | 20.8 | — |
| | 4 | 70.4 | 16.1 | 6.9 | — |
| | 5 | — | 90.7 | 61.2 | 18.9 |
| | 6 | 87.2 | 5.4 | — | — |
| | 7 | 89.8 | 82.9 | 38.4 | — |
| | 8 | 91.7 | 41.1 | — | — |
| | 9 | 92.8 | 70.4 | 5.8 | — |
| | 10 | 53.9 | 18.4 | — | — |
| | 11 | 87.5 | 12.5 | 16.9 | — |
| | 12 | 71.7 | 33.8 | 12.7 | — |
| | 13 | 39.6 | 24.8 | 18.0 | — |
| | 14 | 41.3 | 25.7 | 15.1 | — |
| | 15 | 88.3 | 26.8 | 10.8 | — |
| | 16 | — | 91.7 | 62.1 | 32.8 |
| | 17 | 82.5 | 38.7 | 12.3 | — |
| | 18 | 86.4 | 37.5 | 12.6 | — |
| | 19 | 24.6 | 16.2 | — | — |
| | 20 | 82.5 | 31.7 | 13.5 | — |
| | 21 | 36.8 | 5.3 | — | — |
| | 22 | 71.5 | 32.7 | 10.5 | — |

TABLE 2-continued

Inhibition effect of carbostyril derivatives on ADP-induced aggregation in rabbit platelet

| Test compound No. | Concentration of the test compound solution | | | |
|---|---|---|---|---|
| | $10^{-4}$ mole | $10^{-5}$ mole | $10^{-6}$ mole | $10^{-7}$ mole |
| 23 | 73.6 | 26.1 | 8.7 | — |
| 24 | 43.2 | 22.3 | 13.4 | — |
| Known compounds (Reference compounds) 25 | 57 | 25 | 5 | — |
| 26 | 86 | 54 | −6 | — |
| 27 | 36 | — | 0 | — |
| 28 | −18 | — | 14 | — |
| 29 | 100 | 97 | 10 | — |
| 30 | 100 | 79 | 20 | — |
| 31 | 74 | 38 | 7 | — |
| 32 | 65 | 18 | 2 | — |
| 33 | 82 | 58 | 0 | — |
| 34 | 100 | 90 | 25 | — |
| 35 | 37 | 15 | 10 | — |
| 36 | 13 | 8 | 7 | — |
| 37 | 3 | — | 11 | — |
| 38 | 10 | 5 | 3 | — |
| 39 | 52 | 23 | 5 | — |
| 40 | 28 | 16 | 7 | — |
| 41 | 18 | 13 | 7 | — |
| 42 | 13 | 6 | 0 | — |
| 43 | 22 | 17 | 8 | — |
| 44 | 14 | 6 | 0 | — |
| 45 | 32 | 17 | 9 | — |
| 46 | 7 | 0 | — | — |

PHARMACOLOGICAL TEST 2

A water suspension of test compound was administered at the dose of 30 mg/kg to the overnight fasted male Wister rats and male beagle dogs, and after a predetermined period of time, blood was collected from said animals to obtain plasma. 2 to 3 Milliliters of 0.1 N-NaOH and 2 ml of CHCl$_3$ were added to 1 ml of the obtained plasma, and the mixture was shaken and extracted in a shaker for 2 hours, and after centrifugal separation, the organic layer was washed with 2 ml of 0.1 N-HCl. This organic layer was then subjected to a freezing and thawing treatment, and after evaporating chloroform under nitrogen stream, the residue was redissolved in 100 μl of chloroform and spotted on a thin layer plate of "Silica Gel 60 F$_{254}$" manufactured by Merck & Co., Inc. This was developed in a chloroform: butanol mixed solvent (5:1) and determined by measuring the spots with same Rf value as the test compound according to the absorbance method by using Shimazu CS-910 Thin Layer Chromato-scanner, and therefrom the concentration (μg/ml) of test compound A in blood was determined. The results are shown in Table 3.

TABLE 3

| Test compound No. | Test animal | Concentration in blood (μg/ml) | | | | | |
|---|---|---|---|---|---|---|---|
| | | 1 hr. | 2 hr. | 4 hr. | 6 hr. | 8 hr. | 12 hr. |
| Compounds of the present invention 1 | Rat | 1.05 | 1.62 | 0.94 | 0.53 | — | 0.48 |
| | Beagle dog | 0.28 | 0.31 | 0.21 | 0.13 | 0.08 | 0.05 |
| | Rat | 0.90 | 0.74 | 1.10 | 0.28 | — | 0.64 |
| 16 | Rat | 1.06 | 3.80 | 0.71 | 0.32 | — | 0.73 |
| | Rat | 0.88 | 0.88 | 0.83 | 0.02 | — | 0.78 |
| | Beagle dog | 0.23 | 0.28 | 0.14 | 0.11 | 0.05 | 0.04 |
| 18 | Beagle dog | 0.13 | 0.31 | 0.33 | 0.21 | 0.15 | 0.07 |
| | Rat | 1.32 | 1.74 | 1.02 | 0.69 | 0.56 | 0.42 |
| | Beagle dog | 0.36 | 0.23 | 0.32 | 0.17 | 0.13 | 0.06 |
| 20 | Rat | 0.95 | 1.37 | 0.92 | 0.46 | — | 0.28 |
| | Beagle dog | 0.32 | — | — | 0.08 | 0.05 | — |
| 23 | Rat | 1.53 | 2.24 | 0.94 | 0.54 | 0.39 | 0.52 |
| | Beagle dog | 0.43 | 0.29 | 0.21 | 0.14 | 0.05 | 0.07 |
| Known compounds 29 | Rat | 0.01 | 0 | 0 | — | — | — |
| | Beagle dog | 0.01 | 0 | 0 | — | — | — |
| 34 | Rat | 0.01 | 0 | 0 | — | — | — |
| | Beagle dog | 0 | 0 | — | — | — | — |

PHARMACOLOGICAL TEST 3

The obstructive action against cyclic AMP phosphodiesterase was measured according to the activity measuring method described in "Biochimica et Biophysica Acta", Vol. 429, pp. 485–497 (1976) and "Biochemical Medicine", Vol. 10, pp. 301–311 (1974).

That is, for determining the obstructive activity against cyclic AMP phosphodiesterase, 10 ml of a solution obtained by adding 1 mmol of MgCl$_2$ into 50 mmol of tris-hydrochloric acid buffer with pH 7.4 was added to the platelets obtained by further centrifuging the abovesaid rabbit PRP at 3,000 r.p.m. for 10 minutes, and the suspended platelets were ground by a Teflon potter type homogenizer. This was followed by two times of freezing and thawing treatment and 300-second fracturing with 200 watt supersonic waves. After additional 60-minute centrifugation with 100,000 xg, the supernatant was collected to use it as a crude enzyme solution.

10 Milliliters of this crude buffer solution was added to a 1.5×20 cm DEAE-cellulose column which has previously been buffered with 50 mmol of tris-acetate buffer (pH 6.0), followed by washing and elution with 30 ml of 50 mmol tris-acetate buffer, and this buffer solution was subjected to linear gradient elution with 0 to 0.5 moles of sodium acetate-tris-acetate buffer. The flow rate was 0.5 ml/min, and 5 ml of each fraction was batched out. This operation gave a fraction which has low activity of less than 2 n mole/ml/min with high (100 μmole) cyclic AMP substrate concentration and still has high activity of over 100 p mole/ml/min with low (0.4 μmole) cyclic AMP substrate concentration. This fraction was used as cyclic AMP phosphodiesterase.

0.1 Milliliter of an aqueous solution of each test compound of a specified concentration was mixed with 40 mmol of tris-hydrochloric acid buffer (pH 8.0, containing 50 μg of cow serum albumin and 4 mmol of MgCl$_2$) containing predetermined 1.0 μmol of cyclic AMP (tritium cyclic AMP), and 0.2 ml of this mixed solution was used as substrate solution.

0.2 Milliliter of the above-prepared cyclic AMP phosphodiesterase of a predetermined concentration was added to said substrate solution and the mixture was reaction at 30° C. for 20 minutes, producing tritium 5′-AMP from the tritium cyclic AMP.

The reaction system was then immersed in boiling water for 2 minutes to stop the reaction, and then this reaction solution was cooled in ice water and, for converting the produced tritium 5'-AMP into tritium adenosine, the solution was added with 0.05 ml (1 mg/ml) of snake poison as 5'-nucleotidase and reacted at 30° C. for 10 minutes. The whole amount of this reaction solution was then added to a cation exchange resin (AG 500 W×4, 200–400 meshes, manufactured by Bio-Rad Co., column size: 0.5×1.5 cm), and the produced tritium anodesine alone was allowed to combine, washed with 6 ml of distilled water and eluted with 1.5 ml of 3 N-ammonia water. The whole quantity of the elutant was added with 10 ml of a triton-toluene type scintillator and the produced tritium adenosine was measured by a liquid scintillation counter to determine the phosphodiesterase activity.

In this way, the phosphodiesterase activation value (Vs) of the test compounds of the respective concentrations was determined, and the phosphodiesterase obstruction rate (%) was determined from said activation value (Vs) and control value (Vc) (obtained from water not containing any test compound) from the following formula:

$$\text{Phosphodiesterase obstruction rate (\%)} = \frac{Vc - Vs}{Vc} \times 100$$

Known papaverine and 1-methyl-3-isobutylxanthine were used as controls. The results are shown in Table 4.

TABLE 4

| Test compound No. | Concentration of test compound solution | | | | | |
|---|---|---|---|---|---|---|
| | $10^{-4}$ mole | $10^{-5}$ mole | $10^{-6}$ mole | $10^{-7}$ mole | $10^{-8}$ mole | $10^{-9}$ mole |
| 3 | — | 98.5 | 95.5 | 88.4 | 61.1 | 13.4 |
| 16 | — | 80.5 | 87.5 | 79.3 | 22.3 | 7.1 |
| Papaverine | 100 | 99.8 | 91.4 | 57.3 | — | — |
| 1-Methyl-3-isobutyl-xanthine | 98.5 | 85.7 | 67.4 | 3.2 | — | — |

ACUTE TOXICITY TEST

The test compounds were administered orally to the mice and $LD_{50}$ (mg/kg) of the compounds was determined. The results are shown in Table 5 below.

TABLE 5

| | Test compound | $LD_{50}$ (mg) Male mice Oral administration |
|---|---|---|
| Compounds of the present invention | 1 | >1000 |
| | 2 | >1000 |
| | 3 | >1000 |
| | 4 | >1000 |
| | 5 | >1000 |
| | 6 | >1000 |
| | 7 | >1000 |
| | 8 | >1000 |
| | 9 | >1000 |
| | 10 | >1000 |
| | 11 | >1000 |
| | 12 | >1000 |
| | 13 | >1000 |
| | 14 | >1000 |
| | 15 | >1000 |
| | 16 | >1000 |
| | 17 | >1000 |
| | 18 | >1000 |
| | 19 | >1000 |
| | 20 | >1000 |
| | 21 | >1000 |
| | 22 | >1000 |
| | 23 | >1000 |

TABLE 5-continued

| | Test compound | $LD_{50}$ (mg) Male mice Oral administration |
|---|---|---|
| | 24 | >1000 |
| Known compounds | 25 | >1000 |
| | 26 | >1000 |
| | 27 | 800 ~ 1000 |
| | 28 | >1000 |
| | 29 | >1000 |
| | 30 | >1000 |
| | 31 | 900 ~ 1000 |
| | 32 | >1000 |
| | 33 | >1000 |
| | 34 | >1000 |
| | 35 | 750 ~ 1000 |
| | 36 | >1000 |
| | 37 | 900 ~ 1000 |
| | 38 | 800 ~ 1000 |
| | 39 | >1000 |
| | 40 | 500 ~ 800 |
| | 41 | 500 ~ 800 |
| | 42 | 400 ~ 600 |
| | 43 | 500 ~ 700 |
| | 44 | 500 ~ 600 |
| | 45 | 500 ~ 800 |

CONSIDERATION ON PHARMACOLOGICAL DATA (1) The results of Tables 1 to 3 indicate that the platelet aggregation inhibitory effect of the compounds of this invention is equal to or higher than that of the known carboxy or esterocarbostyril derivatives and yet the compounds of this invention are far longer in said effect retention time than the known derivatives.

It is also noted that the compounds of this invention are far higher in platelet aggregation inhibitory effect than the known amidocarbostyril derivatives and aspirin.

(2) The results of Table 4 indicate that the compounds of this invention are far stronger in phosphodiesterase obstructing action than known 1-methyl-3-isobutylxanthine and equal to or higher than papaverine and also selectively obstruct cyclic AMP phosphodiesterase.

Shown in the following are some reference examples for production of the compounds which are used as starting material in the preparation of the compounds of this invention.

REFERENCE EXAMPLE 1

24 Grams of 5-hydroxy-3,4-dihydrocarbostyril is suspended in 200 ml of acetic acid and 300 ml of chloroform. This suspension is adjusted to 40° to 50° C., and then 36 ml of sulfuryl chloride is added dropwise thereto under agitation, followed by one-hour agitation at the same temperature. The reaction solution is poured into ice-water and the precipitate is filtered out. This product is recrystallized from methanol to obtain 20 gr of 5-hydroxy-6,8-dichloro-3,4-dihydrocarbostyril in the form of colorless plate-like crystals with melting point of 246°–248° C.

REFERENCE EXAMPLE 2

20 Grams of 6-hydroxy-3,4-dihydrocarbostyril is suspended in 100 ml of acetic acid and 200 ml of chloroform, and after adjusting this suspension to 40° to 50° C., 28 ml of sulfuryl chloride is added dropwise to said suspension under agitation, followed by one-hour agitation at the same temperature. The reaction solution is poured into ice-water and the precipitate is filtered out and recrystallized from methanol, resultantly obtaining 3.5 g of 6-hydroxy-5,7,8-trichloro-3,4-dihydrocarbostyril in the form of colorless needle-like crystals with melting point of 251° C. (decomposed).

REFERENCE EXAMPLE 3

24 Grams of 8-hydroxy-3,4-dihydrocarbostyril is dissolved in 200 ml of acetic acid and 200 ml of chloroform, and after adjusting the temperature of this solution to 40° to 50° C., 36 ml of sulfuryl chloride is added dropwise to said solution under agitation and the mixture is further agitated for one hour at the same temperature. The reaction solution is poured into ice-water and the precipitate is filtered out and recrystallized from methanol, producing 25 g of 8-hydroxy-5,6,7-trichloro-3,4-dihydrocarbostyril in the form of white powdery crystals. Melting point: 267°–269° C. (decomposed).

REFERENCE EXAMPLES 4–5

The following compounds are obtained in the same way as above-shown Reference Examples 1–3.

| Reference Example No. | Compound | Crystal form | Melting point (°C.) |
|---|---|---|---|
| 4 | 5-Hydroxy-8-bromo-3,4-dihydrocarbostyril | Colorless needle-like crystals | 212–213.5 (decomposed) |
| 5 | 6-Hydroxy-5-chlorocarbostyril | Colorless crystals | 307.5–308.5 |

REFERENCE EXAMPLE 6

To a solution of 4.5 g of 5-hydroxy-8-bromo-3,4-dihydrocarbostyril in 100 ml of ethanol is added 3.8 g of ethyl bromoacetate and 3.8 g of potassium carbonate, and the mixture is agitated under reflux for 4 hours. The reaction solution is poured into ice-water and the precipitate is filtered out and recrystallized from methanol, obtaining 3.8 g of colorless needle-crystals of 5-ethoxycarbonylmethoxy-8-bromo-3,4-dihydrocarbostyril. m.p., 215°–216° C.

REFERENCE EXAMPLES 7–13

The following compounds are obtained by following the process of above-said Reference Example 6.

| Reference Example No. | | | |
|---|---|---|---|
| 7 | 5-(3-Ethoxycarbonylpropoxy)-8-bromo-3,4-dihydrocarbostyril | Colorless flake-like crystals | 161–161.5 |
| 8 | 5-(3-Ethoxycarbonylpropoxy)-8-iodo-3,4-dihydrocarbostyril | Colorless needle-like crystals | 171.5–172 |
| 9 | 5-(3-Ethoxycarbonylpropoxy)-6,8-diiodo-3,4-dihydrocarbostyril | Colorless needle-like crystals | 164–164.5 |
| 10 | 5-(3-Ethoxycarbonylpropoxy)-6,8-dichloro-3,4-dihydrocarbostyril | Colorless needle-like crystals | 146–147.5 |
| 11 | 5-Chloro-6-ethoxycarbonylmethoxycarbostyril | Colorless needle-like crystals | 247–248 |
| 12 | 5-Chloro-6-(3-methoxycarbonylpropoxy)carbostyril | Colorless flake-like crystals | 208.5–209 |
| 13 | 8-(3-Ethoxycarbonylpropoxy)-5,6,7-trichloro-3,4-dihydrocarbostyril | Colorless needle-like crystals | 142–143 |

REFERENCE EXAMPLE 14

3.6 Grams of 5-ethoxycarbonylmethoxy-8-bromo-3,4-dihydrocarbostyril is dissolved in 150 ml of ethanol, and to this solution is added a 50 ml water solution of 5 g of potassium hydroxide, and the mixture is refluxed for 5 hours. The solvent is distilled off and the residue is dissolved in water and then made acidic with hydrochloric acid. The precipitate is filtered out and recrystallized from aqueous ethanol to obtain 2.5 g of 5-carboxymethoxy-8-bromo-3,4-dihydrocarbostyril in the form of colorless needle-like crystals, m.p., 255°–256° C. (decomposed).

REFERENCE EXAMPLES 15–21

The following compounds are obtained by the method similar to Reference Example 14.

| Reference Example No. | | | |
|---|---|---|---|
| 15 | 5-(3-Carboxypropoxy)-8-bromo-3,4-dihydrocarbostyril | Colorless crystals | 226–227.5 |
| 16 | 5-(3-Carboxypropoxy)-8-iodo-3,4-dihydrocarbostyril | Colorless crystals | 233–234 (decomposed) |
| 17 | 5-(3-Carboxypropoxy)-6,8-diiodo-3,4-dihydrocarbostyril | Colorless crystals | 202.5–203.5 (decomposed) |
| 18 | 5-(3-Carboxypropoxy)-6,8-dichloro-3,4-dihydrocarbostyril | Colorless crystals | 203.5–204.5 |
| 19 | 6-Carboxymethoxy-5-chlorocarbostyril | Colorless needle-like crystals | 320 or higher |
| 20 | 6-(3-Carboxypropoxy)-5-chlorocarbostyril | Colorless needle-like crystals | 251–253 |
| 21 | 8-(3-Carboxypropoxy)-5,6,7-trichloro-3,4-dihydrocarbostyril | Colorless crystals | 203–205 |

REFERENCE EXAMPLE 22

17 Grams of p-methylaminophenol, 20 ml of triethylamine and 9 g of 5% rhodium alumina are added to 200 ml of methanol and the mixture is shaken at the temperature of 60° to 70° C. and under hydrogen pressure of 3 to 4 atm. for 16 hours to effect hydrogenation. After the reaction, the catalyst is filtered off and the mother liquor is concentrated and evaporated to dryness, and the residue is added with 500 ml of chloroform and 200 ml of 5% aqueous NaOH solution. After separating the liquid, the chloroform layer is washed with water and concentrated, and the residue is further distilled under reduced pressure. This treatment gives 11 g of 4-methylaminocyclohexanol with boiling point of 123°–129° C. (at 22 mmHg).

REFERENCE EXAMPLE 23

19 Grams of 2-aminocyclohexanol, 20 g of isopropyl iodide and 15 g of potassium carbonate are added to 50 ml of dimethylformamide and the mixture is agitated at 80°–90° C. for 20 hours. After the reaction, the solution is concentrated and the residue is dissolved in chloroform, washed with water and then dried with anhydrous sodium sulfate ($Na_2SO_4$). After filtering off the desiccant, the mother liquor is concentrated and the residue is crystallized with petroleum ether. The obtained crystals are recrystallized from ethanol, resultantly obtaining 8 g of 2-isopropylaminocyclohexanol in the form of colorless crystals. m.p. 54°–55° C.

REFERENCE EXAMPLE 24

26 Milliliters of N-methylcyclohexylamine is added to 400 ml of ethyl acetate, and then 25 ml of 4-chlorobutyryl chloride and 33.5 ml of triethylamine are added dropwise simultaneously to said solution under external ice cooling and agitation while maintaining the internal temperature at 10° to 20° C. This dropwise addition is performed by spending 20 minutes, followed by 1-hour agitation at room temperature. After the reaction, the reaction solution is added with water, and after separating the liquid, the organic layer is washed with a saturated potassium carbonate solution ($K_2CO_3$ water), 10% hydrochloric acid and water in that order and then dried with anhydrous $Na_2SO_4$. Sodium sulfate is filtered off and the mother liquor is concentrated and then distilled under reduced pressure to obtain 41.5 g of colorless liquid of N-(4-chlorobutyryl)-N-methylcyclohexylamine with boiling point of 133°–136° C. (2 mmHg).

Now the process for producing the compounds of this invention is described by way of examples.

EXAMPLE 1

2.5 Grams of 5-(3-carboxy)propoxy-3,4-dihydrocarbostyril and 2.0 ml of N-methylmorpholine are added to 200 ml of methylene chloride, and then 1.0 ml of methyl chloroformate is added dropwise to said solution under external ice cooling and agitation while maintaining the internal temperature at 10°–20° C. After this dropwise addition, the mixture is further agitated at room temperature for 30 minutes and then added with 1.3 ml of N-ethylaniline, followed by additional 4-hour agitation at the same temperature. After the reaction, the reaction solution is added with water, and after liquid separation, the organic layer is washed with a dilute aqueous NaOH solution, diluted hydrochloric acid and water in that order and then dried with anhydrous $Na_2SO_4$. After filtering out the inorganic matter, the mother liquor is concentrated and the residue is recrystallized from ethanol, consequently obtaining 2.6 g of 5-[3-(N-ethylanilinocarbonyl)propoxy]-3,4-dihydrocarbostyril in the form of colorless needle-like crystals. m.p. 179.5°–180.5° C.

EXAMPLE 2

2.5 Grams of 6-(3-carboxy)propoxycarbostyril and 1.8 ml of pyridine are added to 50 ml of tetrahydrofuran, and then 1.0 ml of methyl bromoformate is added dropwise to said solution under external ice cooling and agitation while maintaining the internal temperature at 5°–15° C. after addition, the mixture is further agitated at room temperature for 1 hour and then added with 1.2 g of N-methylcyclohexylamine, followed by additional 3-hour agitation. The reaction solution is poured into 200 ml of saturated NaCl solution and the precipitated crystals are filtered out and washed with water. The obtained crude crystals are recrystallized from chloroform-ethanol to obtain 2.3 g of 6-[3-(N-methyl-N-cyclohexylaminocarbonyl)propoxy]carbostyril in the form of colorless needle-like crystals with m.p. of 184.5°–186° C.

EXAMPLE 3

2.5 Grams of 6-(3-carboxy)propoxy-3,4-dihydrocarbostyril and 1.4 g of potassium carbonate are added to 50 ml of dimethylformamide, and then 1.1 ml of isobutyl chloroformate is added dropwise to said solution under external ice cooling and agitation while maintaining the internal temperature at 10°–20° C. After said dropwise addition, the mixture is further agitated at 30°–40° C. for 1.5 hours and then added with 1.4 g of N-allylcyclohexylamine, followed by additional 2-hour agitation at the same temperature. The reaction solution is poured into 200 ml of saturated NaCl solution and the precipitated crystals are filtered out and washed with water, and the obtained crude crystals are recrystallized from ethyl acetate petroleum ether, whereby there is obtained 2.7 g of colorless needle-like crystals of 6-[3-(N-allyl-N-cyclohexylaminocarbonyl)propoxy]-3,4-dihydrocarbostyril with melting point of 105°–107° C.

EXAMPLE 4

2.5 Grams of 6-(3-carboxy)propoxy-3,4-dihydrocarbostyril and 1.6 ml of triethylamine are added to 200 ml of ethyl acetate, and then 1.0 ml of ethyl chloroformate is added dropwise to this solution under external ice cooling and agitation while maintaining the internal temperature at 10°–20° C. After addition, the mixture is further agitated at room temperature for 1 hour and then added with 1.1 ml of N-methylaniline, followed by additional 2-hour agitation. The reaction solution is added with water, and after liquid separation, the organic layer is washed with a dilute aqueous NaOH solution, diluted hydrochloric acid and water in that order and then dried with anhydrous $Na_2SO_4$. After filtering out the inorganic matter, the mother liquor is concentrated and the residue is recrystallized from chloroform-petroleum ether to obtain 2.2 g of 6-[3-(N-methylanilinocarbonyl)propoxy]-3,4-dihydrocarbostyril in the form of colorless needlelike crystals, m.p. 129.5°–131.5° C.

EXAMPLES 5–68

The compounds shown in Table 6 below are obtained according to the similar process to Examples 1–4.

TABLE 6

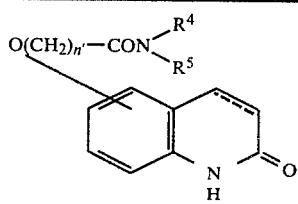

| Example No. | Position of the substituted side chain | Bonding at 3- and 4-positions | n' | R⁴ | R⁵ | Crystal form | Melting point (°C.) |
|---|---|---|---|---|---|---|---|
| 5 | 5 | Single bond | 3 | cyclohexyl | —CH₃ | Colorless rhombic crystals | 133–134 |
| 6 | 5 | Single bond | 3 | cyclohexyl | —CH₂CH=CH₂ | Colorless needle-like crystals | 116.5–118 |
| 7 | 5 | Single bond | 3 | 2-Cl-phenyl | H | Colorless needle-like crystals | 211–212.5 |
| 8 | 5 | Double bond | 3 | cyclohexyl | —CH₃ | Colorless needle-like crystals | 172.5–174 |
| 9 | 5 | Double bond | 3 | phenyl | —C₂H₅ | Colorless needle-like crystals | 216.5–218.5 |
| 10 | 5 | Single bond | 4 | cyclohexyl | —(CH₂)₃CH₃ | Colorless needle-like crystals | 121–123.5 |
| 11 | 6 | Single bond | 1 | cyclohexyl | —C₂H₅ | Colorless rhombic crystals | 133–135 |
| 12 | 6 | Single bond | 1 | phenyl | —(CH₂)₃CH₃ | Colorless rhombic crystals | 111–113 |
| 13 | 6 | Single bond | 1 | 4-OCH₃-phenyl | H | Colorless needle-like crystals | 197–198 |
| 14 | 6 | Single bond | 1 | cycloheptyl | H | Colorless needle-like crystals | 191.5–192.5 |
| 15 | 6 | Single bond | 3 | cyclohexyl | H | Colorless needle-like crystals | 220–221 |
| 16 | 6 | Single bond | 3 | cyclohexyl | —CH₃ | Colorless needle-like crystals | 144–146 |
| 17 | 6 | Single bond | 3 | cyclohexyl | cyclohexyl | Colorless needle-like crystals | 182–184 |
| 18 | 6 | Single bond | 3 | phenyl | H | Colorless plate-like crystals | 186–187 |
| 19 | 6 | Single bond | 3 | phenyl | —(CH₂)₃CH₃ | Colorless rhombic crystals | 108–110 |
| 20 | 6 | Single bond | 3 | phenyl | phenyl | Colorless needle-like crystals | 201–205 |
| 21 | 6 | Single bond | 3 | cyclopropyl | H | Colorless needle-like crystals | 186–187.5 |
| 22 | 6 | Single bond | 3 | 4-NHCOCH₃-phenyl | H | Colorless needle-like crystals | 265–266 (decomposed) |
| 23 | 6 | Single bond | 3 | 3-OH-phenyl | H | Colorless rhombic crystals | 214–215 (decomposed) |
| 24 | 6 | Single bond | 4 | cyclohexyl | —(CH₂)₃CH₃ | Colorless needle-like crystals | 109.5–111.5 |
| 25 | 6 | Single bond | 4 | phenyl | —CH₃ | Colorless rhombic crystals | 129.5–131 |

TABLE 6-continued

Structure: $O(CH_2)_{n'}-CON{<}^{R^4}_{R^5}$ substituted on a 2-oxo-1,2-dihydroquinoline ring.

| Example No. | Position of the sub-stituted side chain | Bonding at 3- and 4-positions | n' | R⁴ | R⁵ | Crystal form | Melting point (°C.) |
|---|---|---|---|---|---|---|---|
| 26 | 6 | Single bond | 4 | 2,3-dimethylphenyl (CH₃, CH₃) | H | Colorless needle-like crystals | 183–184.5 |
| 27 | 6 | Double bond | 3 | cyclohexyl | H | Colorless needle-like crystals | 251–252 |
| 28 | 6 | Double bond | 3 | cyclohexyl | —C₂H₅ | Colorless needle-like crystals | 167.5–169 |
| 29 | 6 | Double bond | 3 | cyclohexyl | —CH(CH₃)₂ | Colorless needle-like crystals | 174–175 |
| 30 | 6 | Double bond | 3 | cyclohexyl | —(CH₂)₃CH₃ | Colorless needle-like crystals | 159–160 |
| 31 | 6 | Double bond | 3 | cyclohexyl | cyclohexyl | Colorless needle-like crystals | 228.5–230.5 |
| 32 | 6 | Double bond | 3 | cyclohexyl | phenyl | Colorless needle-like crystals | 180–181.5 |
| 33 | 6 | Double bond | 3 | 2,3-dimethylphenyl (CH₃, CH₃) | H | Colorless needle-like crystals | 251.5–253 |
| 34 | 6 | Double bond | 3 | phenyl | —CH₃ | Colorless needle-like crystals | 187–189 |
| 35 | 6 | Double bond | 3 | phenyl | —C₂H₅ | Colorless needle-like crystals | 115.5–117 |
| 36 | 6 | Double bond | 3 | phenyl | —(CH₂)₃CH₃ | Colorless needle-like crystals | 159–160.5 |
| 37 | 6 | Double bond | 3 | 2-methylphenyl (CH₃) | —CH₃ | Colorless needle-like crystals | 143–143.5 |
| 38 | 6 | Double bond | 3 | 2-chlorophenyl (Cl) | H | Colorless needle-like crystals | 222.5–224 |
| 39 | 6 | Double bond | 3 | 4-methoxyphenyl (—OCH₃) | H | Colorless needle-like crystals | 236–237 |
| 40 | 6 | Double bond | 4 | cyclohexyl | —(CH₂)₃CH₃ | Colorless needle-like crystals | 151–153.5 |
| 41 | 5 | Single bond | 3 | 4-bromophenyl (—Br) | H | Colorless needle-like crystals | 241.5–242 |
| 42 | 5 | Single bond | 3 | 2-hydroxyphenyl (OH) | H | Colorless needle-like crystals | 206–207 |
| 43 | 5 | Single bond | 6 | phenyl | —C₂H₅ | Colorless plate-like crystals | 129–131.5 |

TABLE 6-continued

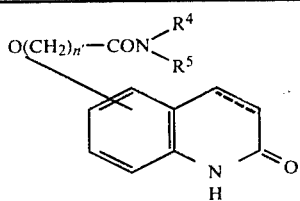

| Example No. | Position of the substituted side chain | Bonding at 3- and 4-positions | n' | R⁴ | R⁵ | Crystal form | Melting point (°C.) |
|---|---|---|---|---|---|---|---|
| 44 | 5 | Double bond | 3 | phenyl | —CH₃ | Colorless flake-like crystals | 223–225 (decomposed) |
| 45 | 5 | Double bond | 3 | 2-methoxyphenyl (OCH₃) | H | Colorless plate-like crystals | 171–175 |
| 46 | 5 | Double bond | 3 | phenyl-(CH₂)₂CH₃ | H | Colorless needle-like crystals | 241–242 (decomposed) |
| 47 | 6 | Single bond | 1 | phenyl-C₂H₅ | H | Colorless needle-like crystals | 202.5–204 |
| 48 | 6 | Double bond | 1 | cyclohexyl | —CH₃ | Pale-yellowish needle-like crystals | 131–133.5 |
| 49 | 6 | Single bond | 3 | phenyl-OH | —CH₃ | Colorless needle-like crystals | 108–112 |
| 50 | 6 | Single bond | 3 | phenyl-CH₃ | —C₂H₅ | Colorless needle-like crystals | 110–111.5 |
| 51 | 6 | Double bond | 3 | phenyl-OCH₃, OCH₃ | H | Colorless needle-like crystals | 209–210 |
| 52 | 6 | Double bond | 3 | cyclohexyl | —CH₂CH₂CH₃ | Colorless needle-like crystals | 182–184.5 |
| 53 | 6 | Double bond | 4 | cyclohexyl | —(CH₂)₃CH₃ | Colorless needle-like crystals | 151–153.5 |
| 54 | 6 | Single bond | 6 | cyclohexyl | —C₂H₅ | Colorless needle-like crystals | 111–112.5 |
| 55 | 6 | Single bond | 6 | cyclohexyl | —CH₂CH₂CH₃ | Colorless needle-like crystals | 90.5–92 |
| 56 | 7 | Single bond | 3 | cyclohexyl | —CH₃ | Colorless rhombic crystals | 114.5–117 |
| 57 | 8 | Double bond | 1 | phenyl-OCH₃, CH₃ | H | Colorless needle-like crystals | 235–236 |
| 58 | 8 | Double bond | 1 | cyclohexyl | —CH₃ | Colorless rhombic crystals | 176–178 |
| 59 | 8 | Single bond | 3 | cyclohexyl | —CH₃ | Colorless rhombic crystals | 141–142 |
| 60 | 8 | Single bond | 3 | phenyl-Cl, Cl | H | Colorless rhombic crystals | 193–195.5 |
| 61 | 6 | Double bond | 3 | cyclopropyl | —C₂H₅ | Colorless needle-like crystals | 150–152 |
| 62 | 6 | Double bond | 3 | cyclopentyl | —C₂H₅ | Colorless needle-like crystals | 158–160 |

TABLE 6-continued

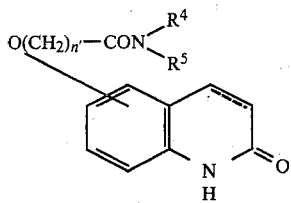

| Example No. | Position of the substituted side chain | Bonding at 3- and 4-positions | n' | R⁴ | R⁵ | Crystal form | Melting point (°C.) |
|---|---|---|---|---|---|---|---|
| 63 | 6 | Double bond | 3 | (cycloheptyl) | —C₂H₅ | Colorless needle-like crystals | 145–147 |
| 64 | 6 | Double bond | 3 | (cyclooctyl) | —C₂H₅ | Colorless needle-like crystals | 143–144.5 |
| 65 | 6 | Double bond | 3 | (cyclohexyl) | —(CH₂)₄CH₃ | Colorless needle-like crystals | 156.5–157.5 |
| 66 | 6 | Double bond | 3 | (cyclohexyl) | —(CH₂)₅CH₃ | Colorless needle-like crystals | 129–132 |
| 67 | 6 | Double bond | 3 | (cyclohexyl) | —(CH₂)₇CH₃ | Colorless crystals | 100–103 |
| 68 | 6 | Single bond | 3 | (cyclohexyl) | —(CH₂)₃CH₃ | Colorless rhombic crystals | 142–143.5 |

EXAMPLE 69

2.5 Grams of 6-(3-carboxy)propoxy-3,4-dihydrocarbostyril and 1.6 ml of triethylamine are added to 150 ml of dimethylformamide, and the mixture is further added dropwise with 1.3 ml of isobutyl chloroformate under external ice cooling and agitation while maintaining the internal temperature at 10° to 20° C. After this dropwise addition, the mixture is agitated at room temperature for 30 minutes, added with 1.3 ml of cyclohexylmethylamine and further agitated for 1 hour. After the reaction, the reaction solution is poured into about 1 liter of water and the precipitated crystals are filtered out and washed with water. The obtained crystals are dried and recrystallized from chloroform-petroleum ether to obtain 3.0 g of 6-{3-[N-(cyclohexylmethyl)aminocarbonyl]propoxy}-3,4-dihydrocarbostyril in the form of colorless needle-like crystals with m.p. of 170°–172° C.

EXAMPLES 70-72

The compounds shown in Table 7 are obtained according to the similar process of Example 69.

TABLE 7

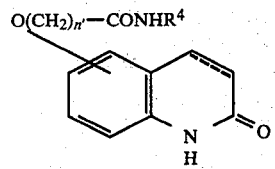

| Ex. No. | Bonding at 3,4-positions | n' | R⁴ | Crystal form | Melting point (°C.) |
|---|---|---|---|---|---|
| 70 | Single bond | 1 | —CH₂—⟨cyclohexyl⟩ | Colorless needle-like crystals | 174.5–176 |

TABLE 7-continued

| Ex. No. | Bonding at 3,4-positions | n' | R⁴ | Crystal form | Melting point (°C.) |
|---|---|---|---|---|---|
| 71 | Single bond | 3 | —CH(CH₃)CH₂—⟨cyclohexyl⟩ | Colorless needle-like crystals | 138–139.5 |
| 72 | Double bond | 3 | —CH(CH₃)CH₂—⟨cyclohexyl⟩ | Colorless needle-like crystals | 173–175 |

EXAMPLE 73

1.3 Grams of 5-(3-carboxy-2-methylpropoxy)-3,4-dihydrocarbostyril and 0.8 ml of triethylamine are added to 50 ml of DMF, and the mixture is added dropwise with 0.65 ml of isobutyl chloroformate under external ice cooling and agitation at internal temperature of 0° to 10° C. After this dropwise addition, the mixture is agitated at room temperature for 30 minutes, added dropwise with 0.7 g of N-ethylcyclohexylamine and further agitated at room temperature for 2 hours. The solvent is distilled off and the residue is dissolved in 200 ml of chloroform, washed with diluted hydrochloric acid, aqueous K₂CO₃ solution and water in that order and then dried with anhydrous Na₂SO₄. After filtering off the inorganic matter, the mother liquor is concentrated and the residue is recrystallized from ligroin-benzene to obtain 0.8 g of 5-[3-(N-cyclohexyl-N-ethylaminocarbonyl)-2-methylpropoxy]-3,4-dihydrocarbostyril in the form of colorless needle-like crystals. m.p. 114°–115.5° C.

EXAMPLE 74

1.3 Grams of 6-(3-carboxy-2-methylpropoxy)-carbostyril and 0.8 ml of triethylamine are added to 50 ml of DMF and dissolved, and to this solution is added dropwise 0.65 ml of isobutyl chloroformate under external ice cooling and agitation. Thereafter, the mixture is agitated at room temperature for 30 minutes and then 0.8 ml of N-methyl-2-methylcyclohexylamine is added dropwise thereto, followed by additional 3-hour agitation. After the reaction, the solvent is distilled off and the residue is dissolved in 300 ml of chloroform, washed with diluted hydrochloric acid, diluted aqueous $K_2CO_3$ solution and water in that order and then dried with anhydrous $Na_2SO_4$. After filtering out the inorganic matter, the residue is recrystallized from benzene-ligroin, resultantly obtaining 0.4 g of colorless needle-like crystals of 6-{3-[N-methyl-N-(2-methylcyclohexyl)aminocarbonyl]-2-methylpropoxy}carbostyril with melting point of 146°–149° C.

EXAMPLE 75

2.6 Grams of 1-methyl-6-(3-carboxypropoxy)-3,4-dihydrocarbostyril and 1.8 ml of pyridine are added to 50 ml of tetrahydrofuran, and then 1.0 ml of methyl bromoformate is added dropwise to this solution under external ice cooling and agitation while maintaining the internal temperature at 5° to 15° C. After this dropwise addition, the mixture is agitated at room temperature for 2 hours, added with 1.2 g of N-methylcyclohexylamine and further agitated for 3 hours. The reaction liquid is poured into 200 ml of saturated NaCl solution and the precipitated crystals are filtered out and washed with water. The thus obtained crude crystals are recrystallized from ligroin to obtain 2.1 g of 1-methyl-6-[3-(N-cyclohexyl)-N-methylaminocarbonylpropoxy]-3,4-dihydrocarbostyril in the form of colorless needle-like crystals, m.p. 104.5°–106.5° C.

EXAMPLE 76

2.6 Grams of 6-(3-carboxy-2-methylpropoxy)-carbostyril and 1.4 g of potassium carbonate are added to 50 ml of dimethylformamide, followed by dropwise addition of 1.1 ml of isobutyl chloroformate under external ice cooling and agitation while maintaining the internal temperature at 10° to 20° C. After this dropwise addition, the mixture is agitated at 30° to 40° C. for 2 hours and then added with 1.6 ml of N-methyl-2-methylcyclohexylamine, followed by additional 2-hour agitation at the same temperature. The reaction solution is poured into 200 ml of saturated NaCl solution and the precipitated crystals are filtered out and washed with water. The obtained crude crystals are recrystallized from benzene-ligroin to obtain 0.9 g of 6-{3-[N-methyl-N-(2-methylcyclohexyl)-aminocarbonyl]-2-methylpropoxy}carbostyril in the form of colorless needle-like crystals. m.p., 146°–149° C.

EXAMPLE 77

2.6 Grams of 5-(3-carboxy-2-methylpropoxy)-3,4-dihydrocarbostyril and 1.6 ml of triethylamine are added to 200 ml of ethyl acetate, followed by dropwise addition of 1.0 ml of ethyl chloroformate under external ice cooling and agitation while maintaining the internal temperature at 10° to 20° C. Thereafter, the mixture is agitated at room temperature for 1 hour, added with 1.4 g of N-ethylcyclohexylamine and further agitated for 1.5 hours. The reaction solution is poured into water to separate the liquid, and the organic layer is washed with dilute aqueous NaOH solution, diluted hydrochloric acid and water in that order and then dried with anhydrous $Na_2SO_4$. After filtering off the inorganic matter, the mother liquor is concentrated and the residue is recrystallized from ligroin-benzene, obtaining 1.5 g of 5-[3-(N-cyclohexyl-N-ethylaminocarbonyl)-2-methylpropoxy]-3,4-dihydrocarbostyril in the form of colorless needle-like crystals with melting point of 114°–115.5° C.

EXAMPLES 78–105

The compounds shown in Table 8 below are obtained from the reactions same as practiced in Examples 73–77.

TABLE 8

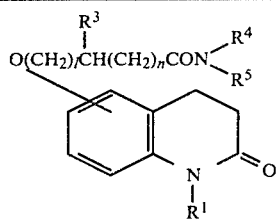

| Example No. | Position of the substituted side chain | $R^1$ | $R^3$<br>\|<br>$(CH_2)_l CH(CH_2)_n$ | $R^4$ | $R^5$ | Crystal form | Melting point (°C.) |
| --- | --- | --- | --- | --- | --- | --- | --- |
| 78 | 5 | H | —CH$_2$— | | H | Pale-yellowish crystals | 286–288.5 (decomposed) |
| 79 | 5 | CH$_3$ | " | | H | Colorless needle-like crystals | 186–187 |
| 80 | 5 | CH$_2$CH=CH$_2$ | CH$_3$<br>\|<br>—CH— | | H | Colorless needle-like crystals | 141.5–142 |

TABLE 8-continued

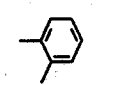

| Example No. | Position of the sub- stituted side chain | $R^1$ | $R^3$ $(CH_2)CH(CH_2)_n$ | $R^4$ | $R^5$ | Crystal form | Melting point (°C.) |
|---|---|---|---|---|---|---|---|
| 81 | 5 | H | " | 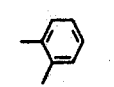 | H | Colorless needle-like crystals | 186–189 |
| 82 | 5 | H | " | 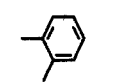 | H | Colorless needle-like crystals | 223–226 |
| 83 | 5 | H | " |  | H | Colorless flake-like crystals | 211–212 |
| 84 | 5 | H | $\begin{array}{c}C_2H_5\\-CH-\end{array}$ | 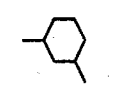 | $C_2H_5$ | Colorless needle-like crystals | 159–161 |
| 85 | 5 | H | " | 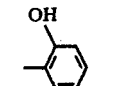 | H | Colorless needle-like crystals | 247–248.5 (decomposed) |
| 86 | 5 | H | $-(CH_2)_2-$ | 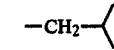 | H | Colorless needle-like crystals | 190.5–192 |
| 87 | 5 | H | $-(CH_2)_3-$ | 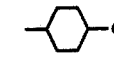 | H | Colorless needle-like crystals | 207–208.5 |
| 88 | 5 | H | " | 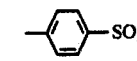 | H | Colorless needle-like crystals | 270–274 (decomposed) |
| 89 | 5 | H | " | 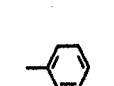 | H | Colorless needle-like crystals | 212–213 |
| 90 | 5 | H | " |  | $CH_3$ | Colorless needle-like crystals | 169–172 |
| 91 | 5 | $C_2H_5$ | " | 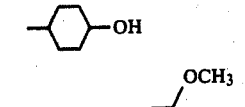 | H | Colorless needle-like crystals | 122.5–124 |
| 92 | 5 | " | " | 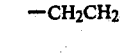 | H | Colorless needle-like crystals | 141.5–143 |
| 93 | 5 | H | $-(CH_2)_6-$ | 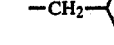 | $-CH_2-$ | Colorless needle-like crystals | 49–52 |
| 94 | 5 | H | $\begin{array}{c}CH_3\\-CH_2CHCH_2-\end{array}$ |  | H | Colorless needle-like crystals | 181–182.5 |
| 95 | 6 | H | $-(CH_2)_3-$ | 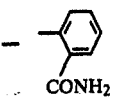 | H | Colorless needle-like crystals | 211.5–213 |
| 96 | 6 | H | " | 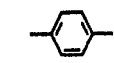 | $CH_3$ | Colorless needle-like crystals | 129.5–132.5 |

TABLE 8-continued

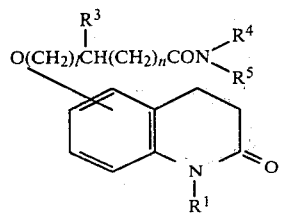

| Example No. | Position of the substituted side chain | $R^1$ | $R^3$ $(CH_2)CH(CH_2)_n$ | $R^4$ | $R^5$ | Crystal form | Melting point (°C.) |
|---|---|---|---|---|---|---|---|
| 97 | 6 | H | " | —CH$_2$CH$_2$—⟨benzene with OCH$_3$, OCH$_3$⟩ | " | Colorless crystals | 31–35 |
| 98 | 6 | CH$_2$CH=CH$_2$ | —(CH$_2$)$_6$— | ⟨cyclohexyl⟩ | H | Colorless needle-like crystals | 104–105.5 |
| 99 | 7 | H | $\begin{array}{c}C_2H_5\\|\\—CH—\end{array}$ | ⟨cyclohexyl⟩ | H | Colorless needle-like crystals | 182.5–183 |
| 100 | 5 | H | —(CH$_2$)$_3$— | ⟨cyclohexyl-CONH$_2$⟩ | H | Colorless needle-like crystals | 236–239 (decomposed) |
| 101 | 5 | H | $\begin{array}{c}OH\\|\\—CH_2CHCH_2—\end{array}$ | ⟨cyclohexyl⟩ | H | Colorless needle-like crystals | 156–158 |
| 102 | 6 | H | —(CH$_2$)$_3$— | ⟨cyclohexyl-OH⟩ | ⟨cyclopropyl⟩ | Colorless needle-like crystals | 160–161 |
| 103 | 6 | H | " | ⟨cyclohexyl-Cl⟩ | CH$_2$—⟨cyclohexyl⟩ | Colorless needle-like crystals | 166–168 |
| 104 | 6 | H | " | ⟨cyclohexyl-NHCOCH$_3$⟩ | H | Colorless needle-like crystals | 298–299 (decomposed) |
| 105 | 6 | H | " | ⟨cyclohexyl-N(CH$_3$)$_2$⟩ | H | Colorless crystals | 235–238 |

EXAMPLES 106–139

The compounds of Table 9 below are obtained from the reactions same as performed in Examples 73–77.

TABLE 9 (1-2)

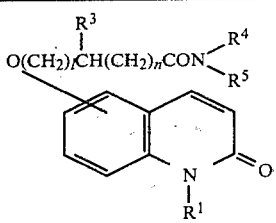

| Example No. | Position of the substituted side-chain | $R^1$ | $R^3$ $(CH_2)CH(CH_2)_n$ | $R^4$ | $R^5$ | Crystal form | Melting point (°C.) |
|---|---|---|---|---|---|---|---|
| 106 | 5 | H | —CH$_2$— | ⟨phenyl-COCH$_3$⟩ | H | Yellowish plate-like crystals | 183–186 |

TABLE 9-continued (1-2)

$$\text{Structure: } O(CH_2)\overset{R^3}{C}H(CH_2)_n CON\overset{R^4}{\underset{R^5}{}} \text{ attached to quinolin-2(1H)-one with } N-R^1$$

| Example No. | Position of the sub-stituted side-chain | $R^1$ | $\overset{R^3}{(CH_2)CH(CH_2)_n}$ | $R^4$ | $R^5$ | Crystal form | Melting point (°C.) |
|---|---|---|---|---|---|---|---|
| 107 | 5 | H | " | $-CH_2CH_2-\text{(3,4-dimethoxyphenyl)}$ (OCH$_3$, OCH$_3$) | H | Colorless plate-like crystals | 181.5–185 |
| 108 | 5 | H | " | $-CHCH_2-\text{cyclopentyl}$, with CH$_3$ branch | H | Colorless needle-like crystals | 202–204.5 |
| 109 | 5 | CH$_3$ | $-CH-$ with CH$_3$ | cyclopropyl | H | Colorless needle-like crystals | 189–190 |
| 110 | 5 | H | $-(CH_2)_3-$ | $-CH_2CH_2-\text{(3,4-dimethoxyphenyl)}$ | H | Colorless flake-like crystals | 168.5–171 |
| 111 | 5 | H | " | $CH_2-\text{cyclohexyl}$ | H | Colorless flake-like crystals | 236.5–237 (decomposed) |
| 112 | 6 | H | $-CH-$ with CH$_3$ | cyclohexyl | CH$_3$ | Colorless plate-like crystals | 172–176 |
| 113 | 6 | H | $-(CH_2)_3-$ | cyclohexyl-OH | H | Colorless needle-like crystals | 255–257 |
| 114 | 6 | $-CH_2-\text{phenyl}$ | " | cyclohexyl | CH$_3$ | Colorless needle-like crystals | 107.5–108.5 |
| 115 | 6 | H | " | cyclohexyl-OH | " | Colorless needle-like crystals | 199–201 |
| 116 | 6 | H | $-(CH_2)_3-$ | cyclohexyl-OCH$_3$ | H | Colorless crystals | 202.5–206 |
| 117 | 6 | H | " | phenyl-COOH | H | Colorless crystals | 268–269 |
| 118 | 6 | H | " | phenyl-COOC$_2$H$_5$ | H | Colorless needle-like crystals | 184–185 |
| 119 | 6 | CH$_3$ | " | cyclohexyl | CH$_3$ | Colorless needle-like crystals | 118.5–119.5 |
| 120 | 6 | H | " | cyclohexyl | $CH_2-\text{phenyl}$ | Colorless needle-like crystals | 185.5–187 |
| 121 | 6 | H | " | cyclohexyl-OCOCH$_3$ | CH$_3$ | Colorless crystals | 187–190 |
| 122 | 6 | H | $-(CH_2)_3-$ | cyclohexyl-CH$_3$ | C$_2$H$_5$ | Colorless needle-like crystals | 150.5–153 |
| 123 | 6 | H | " | cyclohexyl | $CH_2CH_2-\text{phenyl}$ | Colorless needle-like crystals | 163.5–164.5 |
| 124 | 6 | H | $-CH_2CHCH_2-$ with CH$_3$ | phenyl | CH$_2$CH$_2$CH$_3$ | Colorless plate-like crystals | 134.5–137.5 |

TABLE 9-continued

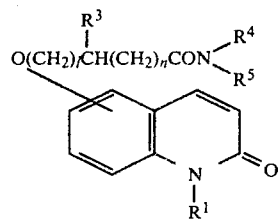

(1-2)

| Example No. | Position of the substituted side-chain | R¹ | $\underset{(CH_2)CH(CH_2)_n}{R^3}$ | R⁴ | R⁵ | Crystal form | Melting point (°C.) |
|---|---|---|---|---|---|---|---|
| 125 | 6 | H | —CH₂CH(OH)CH₂— | —⟨cyclohexyl⟩ | CH₃ | Colorless needle-like crystals | 188–190 (decomposed) |
| 126 | 8 | H | —CH₂— | —CH₂—⟨cyclohexyl⟩ | H | Colorless needle-like crystals | 192.5–193.5 |
| 127 | 6 | H | —(CH₂)₃— | ⟨cyclohexyl-CONH₂⟩ | H | Colorless needle-like crystals | 122–124 |
| 128 | 6 | H | " | ⟨cyclohexyl-CH₃⟩ | CH₃ | Colorless needle-like crystals | 137–140 |
| 129 | 6 | H | " | —CH₂CH₂—⟨C₆H₃(OCH₃)₂⟩ | ⟨cyclohexyl⟩ | Colorless crystals | 78–81 |
| 130 | 6 | H | " | ⟨cyclohexyl-NH₂⟩ | H | Pale yellowish crystals | 157–160 |
| 131 | 6 | H | " | ⟨cyclohexyl-NHCOCH₃⟩ | H | Colorless needle-like crystals | 105–109 |
| 132 | 6 | H | " | —CH₂CH(CH₃)CH₂—⟨cyclohexyl⟩ | CH₃ | Colorless needle-like crystals | 180–182 |
| 133 | 6 | H | " | —CH₂CH(OH)CH₂—⟨cyclohexyl⟩ | H | Colorless needle-like crystals | 201–203 |
| 134 | 6 | H | —(CH₂)₃— | —CH₂CH₂—⟨C₆H₃(OCH₃)₂⟩ | CH₃ | Colorless needle-like crystals | 127.5–129.5 |
| 135 | 6 | H | " | —CH(CH₃)CH₂—⟨cyclopentyl⟩ | C₂H₅ | Colorless rhombic crystals | 105–107 |
| 136 | 6 | H | " | —CH₂—⟨cyclohexyl⟩ | C₂H₅ | Colorless needle-like crystals | 166.5–168 |
| 137 | 6 | H | " | ⟨cyclohexyl-Cl⟩ | (CH₂)₇CH₃ | Colorless needle-like crystals | 127–128.5 |
| 138 | 6 | H | " | ⟨cyclohexyl-CH₃⟩ | (CH₂)₇CH₃ | Colorless crystals | 63.5–66.0 |
| 139 | 6 | H | " | ⟨cyclohexyl-OH⟩ | (CH₂)₇CH₃ | Colorless crystals | 86.0–89.5 |

EXAMPLE 140

The procedure of Example 77 is repeated by using a suitable starting material to obtain 6-{3-[N-benzyl-N-(2-3',4'-dimethoxyphenylethyl)aminocarbonyl]-propoxy}-3,4-dihydrocarbostyril. This compound is identified by the following physicochemical properties.

State: Colorless oil

Silica gel thin-layer chromatography: (Silica gel: "Silica Gel 60 F-254" manufactured by Merck & Co., Inc.); Developing solvent: A mixture of chloroform-methanol [8:1 (vol/vol)], Rf=0.65

Elemental analysis: Calcd. for $C_{30}H_{34}N_2O_5$: C, 71.69%; H, 6.82%; N, 5.57%; Found: C, 71.84%; H, 6.75%; N, 5.29%

Nuclear magnetic resonance spectrum (NMR): $\delta CDCl_3$=1.9–3.1 ppm (10H, m), 3.4 ppm (2H, t), 3.7–4.0 ppm (8H, m), 4.4 ppm (2H, d), 6.4–6.7 ppm (6H, m), 6.9–7.3 ppm (7H, m), 9.3 ppm (1H, br.)

The 6.9–7.3 ppm signal overlaps with the $CHCl_3$ proton signal.

Infrared absorption spectrum (IR): $(\nu_{max}^{film}$ (cm$^{-1}$)=3220, 3002, 2940, 2840, 1670, 1638, 1595, 1500, 1450, 1360, 1240, 1157, 1013, 960, 850, 800, 740

EXAMPLE 141

5.0 Grams of 5-chloro-6-(3-carboxypropoxy)carbostyril and 2.97 ml of triethylamine are added to 100 ml of DMF, followed by dropwise addition thereto of 2.33 ml of isobutyl chloroformate under external ice cooling and agitation while maintaining the internal temperature at 0° to 10° C. After this dropwise addition, the mixture is agitated at room temperature for 1 hour, added dropwise with 2.8 g of N-n-butylcyclohexylamine and further agitated at room temperature for 3 hours. After the reaction, the solvent is distilled off and the residue is dissolved in 600 ml of chloroform, washed with diluted hydrochloric acid, aqueous $K_2CO_3$ solution and water in that order and then dried with anhydrous $Na_2SO_4$. After removing the inorganic matter by filtration, the mother liquor is concentrated and the residue is recrystallized from ethanol, resultantly obtaining 2.5 g of 5-chloro-6-[3-N-cyclohexyl-N-butylaminocarbonyl)propoxy]carbostyril in the form of colorless needle-like crystals. m.p., 178.5°–179.5° C.

EXAMPLES 142–179

The compounds shown in Table 10 below are obtained by the method similar to Example 141. In Table 10, the respective compounds are expressed by the symbols shown in the following general formula (1-3):

TABLE 10

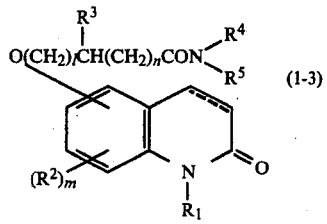

(1-3)

| Ex. No. | Position of the substituted side-chain | Bonding at 3- and 4- positions | $R^1$ | $(R^2)_m$ | Position(s) of the $R^2$ substituted | $R^3$ $\mid$ $(CH_2)_l CH(CH_2)_n$ | $R^4$ | $R^5$ | Crystal form | Melting point (°C.) |
|---|---|---|---|---|---|---|---|---|---|---|
| 142 | 5 | Single bond | H | Br | 8 | —CH$_2$— | —CH$_2$—⟨cyclohexyl⟩ | H | Colorless needle-like crystals | 212–212.5 |
| 143 | 5 | Single bond | H | Br | " | " | —⟨C$_6$H$_4$⟩—N(CH$_3$)$_2$ | H | Colorless needle-like crystals | 258–259.5 |
| 144 | 5 | Single bond | H | Br | " | —(CH$_2$)$_3$— | —⟨cyclohexyl⟩ | CH$_3$ | Colorless needle-like crystals | 134–135 |
| 145 | 5 | Single bond | H | Br | " | " | —⟨C$_6$H$_3$(Cl)(Cl)⟩ | H | Colorless needle-like crystals | 260.5–261 (decomposed) |
| 146 | 5 | Single bond | H | I | " | " | —CH$_2$CH$_2$—⟨C$_6$H$_3$(OCH$_3$)(OCH$_3$)⟩ | H | Colorless needle-like crystals | 190–191 |
| 147 | 5 | Single bond | H | (I)$_2$ | 6 8 | " | —⟨phenyl⟩ | —(CH$_2$)$_3$CH$_3$ | Colorless needle-like crystals | 109.5–110.5 |

TABLE 10-continued

| Ex. No. | Position of the substituted side-chain | Bonding at 3- and 4- positions | $R^1$ | $(R^2)_m$ | Position(s) of the $R^2$ substituted | $\underset{(CH_2)\overset{R^3}{\underset{|}{\overset{|}{C}H}}(CH_2)_n}{}$ | $R^4$ | $R^5$ | Crystal form | Melting point (°C.) |
|---|---|---|---|---|---|---|---|---|---|---|
| 148 | 5 | Single bond | H | $(Cl)_2$ | 6, 8 | " | 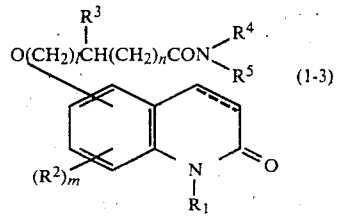 | $C_2H_5$ | Colorless rhombic crystals | 130–132 |
| 149 | 5 | Single bond | H | $(Cl)_2$ | 6, 8 | " | –NHCOCH$_3$ | H | Colorless needle-like crystals | 270–271 (decomposed) |
| 150 | 6 | Double bond | H | Cl | 5 | —CH$_2$— | $\underset{-CHCH_2-}{\overset{CH_3}{\underset{|}{}}}$ | H | Colorless needle-like crystals | 225–226 |
| 151 | 6 | Double bond | H | Cl | " | " | 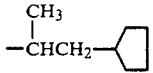 | H | Colorless needle-like crystals | 311.5–313 (decomposed) |
| 152 | 6 | Double bond | H | Cl | " | —(CH$_2$)$_3$— |  | CH$_3$ | Colorless needle-like crystals | 179–180.5 |
| 153 | 6 | Double bond | H | Cl | " | " | 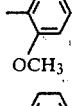 | " | Colorless needle-like crystals | 191.5–193 |
| 154 | 6 | Double bond | CH$_3$ | Cl | " | " |  | " | Pale-yellowish needle-like crystals | 137–138 |
| 155 | 6 | Double bond | H | Cl | " | " |  | $C_2H_5$ | Colorless needle-like crystals | 134.5–136 |
| 156 | 8 | Single bond | H | $(Cl)_3$ | 5, 6, 7 | " |  | CH$_3$ | Colorless needle-like crystals | 131–132.5 |
| 157 | 5 | Single bond | H | OH | 8 | " |  | " | Colorless crystals | 119–121 |
| 158 | 5 | Single bond | H | " | " | " |  | CH$_2$CH$_2$CH$_3$ | Colorless crystals | 116–117 |
| 159 | 5 | Single bond | H | OCH$_2$– | " | " |  | CH$_3$ | Colorless prism crystals | 106.5–110 |
| 160 | 5 | Single bond | H | " | " | " | 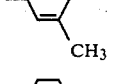 | CH$_2$CH$_2$CH$_3$ | Colorless plate-like crystals | 88–90.5 |

EXAMPLE 161

3.7 Grams of 6-[3-(p-nitrophenoxycarbonyl)propoxy]-carbostryil is dissolved in 40 ml of dimethylformamide, and the mixed solution is further added with 2.0 g of cyclohexylamine and allowed to stand overnight at room temperature. The reaction solution is concentrated under reduced pressure and evaporated to dryness, and the obtained residue is refined by silica gel column chromatography (silica gel: Wakogel C-200; eluent: chloroform) and then recrystallized from ethanol) to obtain 1.5 g of 6-[3-(N-cyclohexylaminocarbonyl)propoxy]carbostyril in the form of colorless needle-like crystals with melting point of 251°-252° C.

EXAMPLE 162

3.8 Grams of 6-[3-(p-nitrophenoxycarbonyl)-2-methylpropoxy]carbostyril is dissolved in 40 ml of dimethylformamide, followed by addition of 1.6 ml of N-methyl-2-methylcyclohexylamine and 12-hour agitation at 60°-70° C. After the reaction, the solvent is distilled off and the obtained residue is refined by silica gel column chromatography (silica gel: Wakogel C-200; eluent: 20/1 (V/V) chloroform/methanol) and the crude crystals are recrystallized from benzene-ligroin to obtain 1.6 g of 6-{3-[N-methyl-N-(2-methylcyclohexyl)aminocarbonyl]-2-methylpropoxy}carbostyril in the form of colorless needlelike crystals with melting point of 146°-149° C.

EXAMPLES 163-204

The compounds in Tables 11 to 13 below are obtained according to the procedure of Examples 161-162.

The respective compounds in Table 11, Table 12 and Table 13 are expressed by the symbols given in the afore-shown general formulae (1-1), (1-2) and (1-3), respectively.

TABLE 11

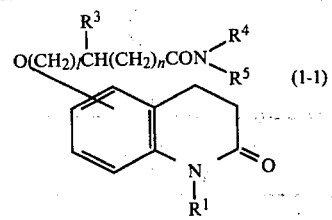

(1-1)

| Example No. | Position of the substituted side-chain | $R^1$ | $R^3$ $(CH_2)_xCH(CH_2)_n$ | $R^4$ | $R^5$ | Crystal form | Melting point (°C.) |
|---|---|---|---|---|---|---|---|
| 163 | 5 | H | —CH$_2$— | ![Cl,NO2-phenyl] | H | Pale-yellowish crystals | 286–288.5 (decomposed) |
| 164 | 5 | CH$_2$CH=CH$_2$ | CH$_3$<br>\|<br>—CH— | ![OCH3-phenyl] | H | Colorless needle-like crystals | 141.5–142 |
| 165 | 5 | H | " | ![CONHCH3-phenyl] | H | Colorless flake-like crystals | 211–212 |
| 166 | 5 | H | —(CH$_2$)$_3$— | ![OCH3-cyclohexyl] | H | Colorless needle-like crystals | 207–208.5 |
| 167 | 5 | H | CH$_3$<br>\|<br>—CH$_2$CHCH$_2$— | ![cyclohexyl] | C$_2$H$_5$ | Colorless needle-like crystals | 114–115.5 |
| 168 | 5 | H | —(CH$_2$)$_6$— | ![cyclohexyl] | —CH$_2$—![phenyl] | Colorless needle-like crystals | 49–52 |
| 169 | 6 | H | —(CH$_2$)$_3$— | ![N(CH3)2-phenyl] | H | Colorless needle-like crystals | 211.5–213 |
| 170 | 6 | CH$_3$ | " | ![cyclohexyl] | CH$_3$ | Colorless needle-like crystals | 104.5–106.5 |
| 171 | 6 | H | " | —CH$_2$CH$_2$—![(OCH3)2-phenyl] | " | Colorless crystals | 31–35 |
| 172 | 6 | CH$_2$CH=CH$_2$ | —(CH$_2$)$_6$— | ![cyclohexyl] | H | Colorless needle-like crystals | 104–105.5 |
| 173 | 7 | H | C$_2$H$_5$<br>\|<br>—CH— | ![cycloheptyl] | H | Colorless needle-like crystals | 182.5–183 |
| 174 | 5 | H | —(CH$_2$)$_3$— | ![cyclohexyl] | CH$_3$ | Colorless rhombic crystals | 133–134 |
| 175 | 6 | H | —(CH$_2$)$_3$— | ![cyclohexyl] | —CH$_2$CH=CH$_2$ | Colorless needle-like crystals | 105–107 |
| 176 | 6 | H | " | ![cyclohexyl] | ![cyclohexyl] | Colorless needle-like crystals | 182–184 |

TABLE 11-continued

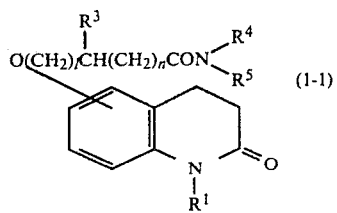
(1-1)

| Example No. | Position of the substituted side-chain | R¹ | $\overset{R^3}{(CH_2)CH(CH_2)_n}$ | R⁴ | R⁵ | Crystal form | Melting point (°C.) |
|---|---|---|---|---|---|---|---|
| 177 | 6 | H | —(CH₂)₄— | cyclohexyl | —(CH₂)₃CH₃ | Colorless needle-like crystals | 109.5–111.5 |
| 178 | 6 | H | " | 2,6-dimethylphenyl | H | Colorless needle-like crystals | 183–184.5 |

TABLE 12

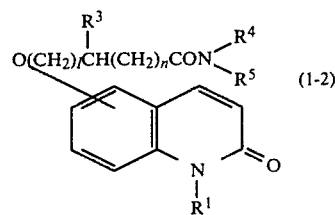
(1-2)

| Example No. | Position of the substituted side-chain | R¹ | $\overset{R^3}{(CH_2)CH(CH_2)_n}$ | R⁴ | R⁵ | Crystyal form | Melting point (°C.) |
|---|---|---|---|---|---|---|---|
| 179 | 5 | CH₃ | $-\overset{\overset{CH_3}{\vert}}{CH}-$ | cyclopropyl | H | Colorless needle-like crystals | 189–190 |
| 180 | 5 | H | —CH₂— | $-\overset{\overset{CH_3}{\vert}}{CH}CH_2-$ cyclopentyl | H | Colorless needle-like crystals | 202–204.5 |
| 181 | 6 | H | $-CH_2\overset{\overset{OH}{\vert}}{CH}CH_2-$ | cyclohexyl | CH₃ | Colorless needle-like crystals | 188–190 (decomposed) |
| 182 | 6 | H | —(CH₂)₃— | cyclohexyl-OCOCH₃ | " | Colorless crystals | 187–190 |
| 183 | 6 | H | " | cyclohexyl-CH₃ | C₂H₅ | Colorless needle-like crystals | 150.5–153 |
| 184 | 6 | H | " | cyclohexyl | CH₂CH₂-phenyl | Colorless needle-like crystals | 163.5–164.5 |
| 185 | 6 | H | " | cyclohexyl-OH | H | Colorless needle-like crystals | 255–257 |
| 186 | 6 | CH₂-phenyl | " | cyclohexyl | CH₃ | Colorless needle-like crystals | 107.5–108.5 |
| 187 | 6 | H | " | cyclohexyl-OH | " | Colorless needle-like crystals | 199–201 |
| 188 | 6 | H | " | cyclohexyl-OCH₃ | H | Colorless crystals | 202.5–206 |
| 189 | 6 | CH₃ | " | cyclohexyl | CH₃ | Colorless needle-like crystals | 118.5–119.5 |

TABLE 12-continued

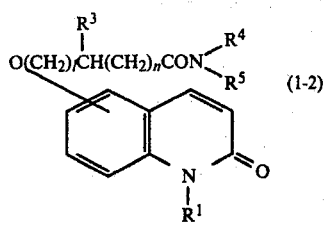
(1-2)

| Example No. | Position of the sub-stituted side-chain | R¹ | $R^3$<br>(CH$_2$)$_l$CH(CH$_2$)$_n$ | R⁴ | R⁵ | Crystal form | Melting point (°C.) |
|---|---|---|---|---|---|---|---|
| 190 | 6 | H | —(CH$_2$)$_3$— | cyclohexyl | CH$_2$-phenyl | Colorless needle-like crystals | 185.6–187 |
| 191 | 6 | H | CH$_3$<br>—CH— | cyclohexyl | CH$_3$ | Colorless plate-like crystals | 172–176 |
| 192 | 8 | H | —CH$_2$— | CH$_2$-cyclohexyl | H | Colorless needle-like crystals | 192.5–193.5 |
| 193 | 6 | H | —(CH$_2$)$_3$— | cyclohexyl | 3-methylphenyl | Colorless needle-like crystals | 180–181.5 |
| 194 | 6 | H | " | cyclohexyl | (CH$_2$)$_3$CH$_3$ | Colorless needle-like crystals | 159–160 |

TABLE 13

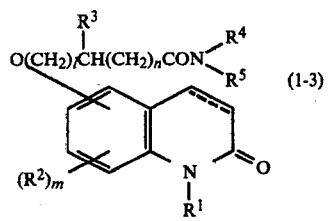
(1-3)

| Ex. No. | Position of the sub-stituted side-chain | Bonding at 3- and 4-positions | R¹ | (R²)$_m$ | Position(s) of the sub-stituted R² group | $R^3$<br>(CH$_2$)$_l$CH(CH$_2$)$_n$ | R⁴ | R⁵ | Crystal form | Melting point (°C.) |
|---|---|---|---|---|---|---|---|---|---|---|
| 195 | 5 | Single bond | H | Br | 8 | —CH$_2$— | CH$_2$-cyclohexyl | H | Colorless needle-like crystals | 212–212.5 |
| 196 | 5 | Single bond | H | (I)$_2$ | 6<br>8 | —(CH$_2$)$_3$— | phenyl | (CH$_2$)$_3$CH$_3$ | Colorless needle-like crystals | 109.5–110.5 |
| 197 | 8 | Single bond | H | (Cl)$_3$ | 5<br>6<br>7 | —(CH$_2$)$_3$— | cyclohexyl | CH$_3$ | Colorless needle-like crystals | 131–132.5 |
| 198 | 5 | Single bond | H | (Cl)$_2$ | 6<br>8 | —(CH$_2$)$_3$— | phenyl | C$_2$H$_5$ | Colorless rhombic crystals | 130–132 |
| 199 | 5 | Single bond | H | OCH$_2$-phenyl | 8 | " | cyclohexyl | CH$_3$ | Colorless prism-like crystals | 106.5–110 |
| 200 | 6 | Double bond | H | Cl | 5 | —CH$_2$— | CH$_3$<br>—CHCH$_2$-cyclopentyl | H | Colorless needle-like crystals | 225–226 |
| 201 | 6 | Double bond | H | Cl | " | " | 3-CH$_3$, 5-OCH$_3$-phenyl | H | Colorless needle-like crystals | 311.5–313 (decomposed) |

TABLE 13-continued

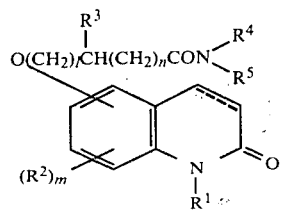

| Ex. No. | Position of the substituted side-chain | Bonding at 3- and 4- positions | $R^1$ | $(R^2)_m$ | Position(s) of the substituted $R^2$ group | $R^3$ $\mid$ $(CH_2)_l CH(CH_2)_n$ | $R^4$ | $R^5$ | Crystal form | Melting point (°C.) |
|---|---|---|---|---|---|---|---|---|---|---|
| 202 | 6 | Double bond | H | Cl | " | —(CH₂)₃— | cyclohexyl | CH₃ | Colorless needle-like crystals | 191.5–193 |
| 203 | 6 | Double bond | CH₃ | Cl | " | " | cyclohexyl | " | Pale-yellowish needle-like crystals | 137–138 |
| 204 | 5 | Single bond | H | OH | 8 | —(CH₂)₃— | phenyl | —CH₂CH₂CH₃ | Colorless crystals | 116–117 |

EXAMPLE 205

2.5 Grams of 6-(3-carboxy)propoxycarbostyril and 1.2 g of N-methylcyclohexylamine are added to a mixed solvent of 20 ml of dioxane and 20 ml of methylene chloride, and to this mixture is added dropwise a solution of 2.1 g of N,N'-dicyclohexylcarbodiimide in 5 ml of methylene chloride maintained at 10°–20° C. under external ice cooling and agitation, followed by additional 3.5-hour agitation at the same temperature. The precipitated crystals are filtered out and the filtrate is concentrated under reduced pressure and evaporated to dryness. The obtained residue is dissolved in 100 ml of methylene chloride and the organic layer is washed with a 5% aqueous solution of hydrochloric acid, a 5% aqueous solution of sodium carbonate and water in that order and then dried with anhydrous sodium sulfate. After distilling off the solvent under reduced pressure, the residue is recrystallized from chloroform-ethanol to obtain 1.9 g of 6-[3-(N-methyl-N-cyclohexylaminocarbonyl)propoxy]-carbostyril in the form of colorless needle-like crystals with melting point of 184.5°–186° C.

EXAMPLE 206

To a solution of 2.9 g of 5-(6-carboxyhexyloxy)-3,4-dihydrocarbostyril and 1.9 g of N-benzylcyclohexylamine in 100 ml of DMF is added gradually dropwise a solution of 2.1 g of N,N'-dicyclohexylcarbodiimide in 10 ml of DMF at room temperature and under agitation. After this agitation, the mixture is further agitated at room temperature for 5 hours. After the reaction, the insolubles are filtered off and the mother liquor is concentrated. The residue is dissolved in chloroform and subjected to silica gel thin-layer chromatography (solvent: chloroform-methanol (8:1) to scrape out the portion with Rf value of 0.8. The silica gel is extracted with chloroform, and after distilling off chloroform, the residue is recrystallized from benzene-ligroin to obtain 1.1 g of 5-[6-(N-cyclohexyl-N-benzylaminocarbonyl)hexyloxy]-3,4-dihydrocarbostyril in the form of colorless needle-like crystals with melting point of 49°–52° C.

EXAMPLES 207–243

The compounds shown in Tables 14–16 below are obtained by following the same procedure as Examples 205 and 206. The respective compounds in Table 14, Table 15 and Table 16 are expressed by the symbols given in the aforeshown general formulae (1-1); (1-2) and (1-3), respectively.

TABLE 14

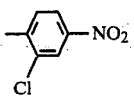
(1-1)

| Example No. | Position of the sub-stituted side-chain | $R^1$ | $R^3$<br>(CH$_2$)$_l$CH(CH$_2$)$_n$ | $R^4$ | $R^5$ | Crystal form | Melting point (°C.) |
|---|---|---|---|---|---|---|---|
| 207 | 5 | H | —CH$_2$— | 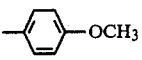 | H | Pale-yellowish crystals | 286–288.5 (decomposed) |
| 208 | 5 | CH$_2$CH=CH$_2$ | CH$_3$<br>—CH— | 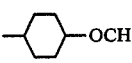 | H | Colorless needle-like crystals | 141.5–142 |
| 209 | 5 | H | —(CH$_2$)$_3$— | 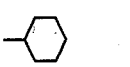 | H | Colorless needle-like crystals | 207–208.5 |
| 210 | 5 | H | CH$_3$<br>—CH$_2$CHCH$_2$— | 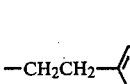 | C$_2$H$_5$ | Colorless needle-like crystals | 114–115.5 |
| 211 | 6 | H | —(CH$_2$)$_3$— | 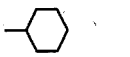 | CH$_3$ | Colorless crystals | 31–35 |
| 212 | 6 | CH$_3$ | " | 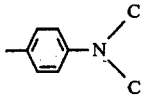 | CH$_3$ | Colorless needle-like crystals | 104.5–106.5 |
| 213 | 6 | H | " | 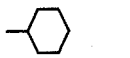 | H | Colorless needle-like crystals | 211.5–213 |
| 214 | 6 | CH$_2$CH=CH$_2$ | —(CH$_2$)$_6$— | 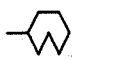 | H | Colorless needle-like crystals | 104–105.5 |
| 215 | 7 | H | C$_2$H$_5$<br>—CH— | 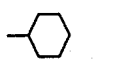 | H | Colorless needle-like crystals | 182.5–183 |
| 216 | 6 | H | —(CH$_2$)$_3$— | 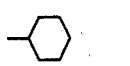 | —CH$_2$CH=CH$_2$ | Colorless needle-like crystals | 105–107 |
| 217 | 6 | H | " | 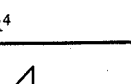 | 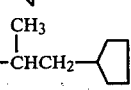 | Colorless needle-like crystals | 182–184 |

TABLE 15

O(CH$_2$)$_l$CH(CH$_2$)$_n$CON$R^4_{R^5}$ (1-2)

| Example No. | Position of the sub-stituted side-chain | $R^1$ | $R^3$<br>(CH$_2$)$_l$CH(CH$_2$)$_n$ | $R^4$ | $R^5$ | Crystal form | Melting point (°C.) |
|---|---|---|---|---|---|---|---|
| 218 | 5 | CH$_3$ | CH$_3$<br>—CH— | ◁ | H | Colorless needle-like crystals | 189–190 |
| 219 | 5 | H | —CH$_2$— | CH$_3$<br>—CHCH$_2$-cyclopentyl | H | Colorless needle-like crystals | 202–204.5 |
| 220 | 8 | H | " | —CH$_2$-cyclohexyl | H | Colorless needle-like crystals | 192.5–193.5 |

TABLE 15-continued $$\text{O(CH}_2\text{)CH(CH}_2\text{)}_n\text{CON}\begin{array}{c}R^3\\R^4\\R^5\end{array}\quad (1\text{-}2)$$

(quinolin-2(1H)-one structure with N-R¹)

| Example No. | Position of the sub- stituted side-chain | R¹ | $\overset{R^3}{(CH_2)CH(CH_2)_n}$ | R⁴ | R⁵ | Crystal form | Melting point (°C.) |
|---|---|---|---|---|---|---|---|
| 221 | 6 | H | —CH(CH₃)— | cyclohexyl | CH₃ | Colorless plate-like crystals | 172–176 |
| 222 | 6 | H | —(CH₂)₃— | 3-methylcyclohexyl | C₂H₅ | Colorless needle-like crystals | 150.5–153 |
| 223 | 6 | CH₂–phenyl | " | cyclohexyl | CH₃ | Colorless needle-like crystals | 107.5–108.5 |
| 224 | 6 | H | " | 4-(OCOCH₃)cyclohexyl | CH₃ | Colorless crystals | 187–190 |
| 225 | 6 | H | " | 4-(OCH₃)cyclohexyl | H | Colorless crystals | 202.5–206 |
| 226 | 6 | CH₃ | " | cyclohexyl | CH₃ | Colorless needle-like crystals | 118.5–119.5 |
| 227 | 6 | H | " | cyclohexyl | CH₂–phenyl | Colorless needle-like crystals | 185.5–187 |
| 228 | 6 | H | " | cyclohexyl | CH₂CH₂–phenyl | Colorless needle-like crystals | 163.5–164.5 |
| 229 | 6 | H | —CH₂CH(CH₃)CH₂— | cyclohexyl | CH₃ | Colorless needle-like crystals | 146–149 |
| 230 | 6 | H | —CH₂CH(OH)CH₂— | cyclohexyl | CH₃ | Colorless needlelike-crystals | 188–190 (decomposed) |
| 231 | 6 | H | —(CH₂)₃— | 2-methylphenyl | CH₃ | Colorless needle-like crystals | 143–143.5 |
| 232 | 6 | H | " | cyclohexyl | phenyl | Colorless needle-like crystals | 180–181.5 |
| 233 | 6 | H | —(CH₂)₄— | cyclohexyl | —(CH₂)₃CH₃ | Colorless needle-like crystals | 151–153.5 |

TABLE 16

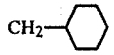

(1-3)

| Example No. | Position of the substituted side-chain | Bonding at 3- and 4- positions | R¹ | (R²)ₘ | Position(s) of the substituted R² group | R³ in (CH₂)ₓCH(CH₂)ₙ | R⁴ | R⁵ | Crystal form | Melting point (°C.) |
|---|---|---|---|---|---|---|---|---|---|---|
| 234 | 5 | Single bond | H | Br | 8 | —CH₂— | CH₂— | H | Colorless needle-like crystals | 212–212.5 |
| 235 | 5 | Single bond | H | (I)₂ | 6, 8 | —(CH₂)₃— |  | (CH₂)₃CH₃ | Colorless needle-like crystals | 109.5–110.5 |
| 236 | 8 | Single bond | H | (Cl)₃ | 5, 6, 7 | " |  | CH₃ | Colorless needle-like crystals | 131–132.5 |
| 237 | 5 | Single bond | H | (Cl)₂ | 6, 8 | —(CH₂)₃— |  | C₂H₅ | Colorless rhombic crystals | 130–132 |
| 238 | 5 | Single bond | H | OCH₂— | 8 | " | 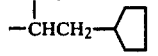 | (CH₂)₂CH₃ | Colorless plate-like crystals | 88–90.5 |
| 239 | 6 | Double bond | H | Cl | 5 | —CH₂— | CH₃<br>\|<br>—CHCH₂— | H | Colorless needle-like crystals | 225–226 |
| 240 | 6 | Double bond | H | Cl | " | " |  (with CH₃ and OCH₃) | H | Colorless needle-like crystals | 311.5–313 (decomposed) |
| 241 | 6 | Double bond | H | Cl | " | —(CH₂)₃— |  | CH₃ | Colorless needle-like crystals | 191.5–193 |
| 242 | 6 | Double bond | CH₃ | Cl | " | " |  | " | Pale-yellowish needle-like crystals | 137–138 |
| 243 | 5 | Single bond | H | OH | 8 | " | " | " | Colorless crystals | 119–121 |

EXAMPLE 244

2.7 Grams of 6-(3-ethoxycarbonyl-2-methylpropoxy)-carbostyril, 0.5 g of sodium ethylate and 5 ml of N-methyl-2-methylcyclohexylamine are added to 100 ml of ethanol, and the mixture is reacted in an autoclave under 110 atm. and at 140° to 150° C. for 6 hours. After cooling, the reaction solution is concentrated under reduced pressure and the residue is dissolved in 200 ml of chloroform, washed with a 1% aqueous K₂CO₃ solution, diluted hydrochloric acid and water in that order and then dried with anhydrous Na₂SO₄. The solvent is distilled off and the residue is refined by silica gel column chromatography (silica gel: Wakogel C-200; eluent: 20/1 (V/V) chloroform-methanol) and the obtained crude crystals are recrystallized from benzene-ligroin, resultantly obtaining 1.0 g of 6-{3-[N-methyl-N-(2-methylcyclohexyl)aminocarbonyl]-2-methylpropoxy}carbostyril in the form of colorless needle-like crystals with melting point of 146°–149° C.

EXAMPLES 245–283

The compounds of Tables 17–19 below are obtained by repeating the reaction process of Example 244. The respective compounds in Table 17, Table 18 and Table 19 are expressed by the symbols given in the general formulae (1-1), (1-2) and (1-3), respectively.

TABLE 17

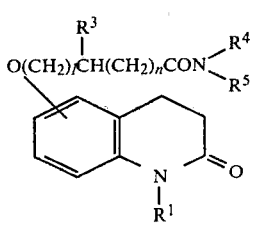

| Example No. | Position of the substituted side-chain | $R^1$ | $R^3$<br>$(CH_2)\overline{CH(CH_2)}_n$ | $R^4$ | $R^5$ | Crystal form | Melting point (°C.) |
|---|---|---|---|---|---|---|---|
| 245 | 5 | $CH_2CH=CH_2$ | $\underset{-CH-}{\overset{CH_3}{\mid}}$ | —⟨⟩—OCH₃ | H | Colorless needle-like crystals | 141.5–142 |
| 246 | 5 | H | $\underset{-CH-}{\overset{CH_3}{\mid}}$ | —⟨⟩— (2-CONHCH₃) | H | Colorless flake-like crystals | 211–212 |
| 247 | 5 | H | $-(CH_2)_3-$ | —⟨cyclohexyl⟩—OCH₃ | H | Colorless needle-like crystals | 207–208.5 |
| 248 | 5 | H | $-CH_2\overset{CH_3}{\underset{\mid}{CH}}CH_2-$ | —⟨cyclohexyl⟩ | $C_2H_5$ | Colorless needle-like crystals | 114–115.5 |
| 249 | 6 | H | $-(CH_2)_3-$ | $-CH_2CH_2-$⟨3,4-diOCH₃-phenyl⟩ | $CH_3$ | Colorless crystals | 31–35 |
| 250 | 6 | $CH_3$ | $-(CH_2)_3-$ | —⟨cyclohexyl⟩ | $CH_3$ | Colorless needle-like crystals | 104.5–106.5 |
| 251 | 6 | $CH_2CH=CH_2$ | $-(CH_2)_6-$ | —⟨cyclohexyl⟩ | H | Colorless needle-like crystals | 104–105.5 |
| 252 | 7 | H | $\underset{-CH-}{\overset{C_2H_5}{\mid}}$ | —⟨cyclopentyl⟩ | H | Colorless needle-like crystals | 182.5–183 |
| 253 | 5 | H | $-(CH_2)_6-$ | —⟨cyclohexyl⟩ | $CH_2$—⟨phenyl⟩ | Colorless needle-like crystals | 49–52 |
| 254 | 5 | H | $-(CH_2)_3-$ | —⟨cyclohexyl⟩ | $-CH_2CH=CH_2$ | Colorless needle-like crystals | 116.5–118 |
| 255 | 6 | H | $-(CH_2)_3-$ | —⟨cyclohexyl⟩ | $CH_3$ | Colorless needle-like crystals | 144–146 |
| 256 | 6 | H | $-(CH_2)_3-$ | —⟨phenyl⟩ | —⟨phenyl⟩ | Colorless needle-like crystals | 201–205 |
| 257 | 5 | H | $-(CH_2)_3-$ | —⟨2-Cl-phenyl⟩ | H | Colorless needle-like crystals | 211–212.5 |
| 258 | 6 | H | $-(CH_2)_3-$ | —⟨phenyl⟩ | —⟨cyclohexyl⟩ | Colorless needle-like crystals | 182–184 |

TABLE 18

$$\text{(1-2)}$$

Structure: O(CH$_2$)$_l$CH(R$^3$)(CH$_2$)$_n$CON(R$^4$)(R$^5$) substituent on quinolin-2(1H)-one ring with N-R$^1$.

| Example No. | Position of the substituted side-chain | R$^1$ | $\overset{R^3}{\underset{}{(CH_2)_l CH(CH_2)_n}}$ | R$^4$ | R$^5$ | Crystal form | Melting point (°C.) |
|---|---|---|---|---|---|---|---|
| 259 | 5 | H | —CH$_2$— | —CH(CH$_3$)CH$_2$-cyclopentyl | H | Colorless needle-like crystals | 202–204.5 |
| 260 | 8 | H | —CH$_2$— | —CH$_2$-cyclohexyl | H | Colorless needle-like crystals | 192.5–193.5 |
| 261 | 6 | H | —CH(CH$_3$)— | cyclohexyl | CH$_3$ | Colorless plate-like crystals | 172–176 |
| 262 | 6 | H | —(CH$_2$)$_3$— | 3-methylcyclohexyl | C$_2$H$_5$ | Colorless needle-like crystals | 150.5–153 |
| 263 | 6 | CH$_2$-phenyl | —(CH$_2$)$_3$— | cyclohexyl | CH$_3$ | Colorless needle-like crystals | 107.5–108.5 |
| 264 | 6 | H | —(CH$_2$)$_3$— | 4-methoxycyclohexyl | H | Colorless crystals | 202.5–206 |
| 265 | 6 | CH$_3$ | —(CH$_2$)$_3$— | cyclohexyl | CH$_3$ | Colorless needle-like crystals | 118.5–119.5 |
| 266 | 6 | H | —(CH$_2$)$_3$— | cyclohexyl | CH$_2$-phenyl | Colorless needle-like crystals | 185.5–187 |
| 267 | 6 | H | —(CH$_2$)$_3$— | cyclohexyl | CH$_2$CH$_2$-phenyl | Colorless needle-like crystals | 163.5–164.5 |
| 268 | 6 | H | —CH$_2$CH(OH)CH$_2$— | cyclohexyl | CH$_3$ | Colorless needle-like crystals | 188–190 (decomposed) |
| 269 | 6 | H | —(CH$_2$)$_3$— | cyclohexyl | H | Colorless needle-like crystals | 251–252 |
| 270 | 6 | H | —(CH$_2$)$_3$— | cyclohexyl | CH$_3$ | Colorless needle-like crystals | 184.5–186 |
| 271 | 6 | H | —(CH$_2$)$_3$— | cyclohexyl | —(CH$_2$)$_3$CH$_3$ | Colorless needle-like crystals | 159–160 |
| 272 | 6 | H | —(CH$_2$)$_3$— | phenyl | C$_2$H$_5$ | Colorless needle-like crystals | 115.5–117 |
| 273 | 6 | H | —(CH$_2$)$_3$— | 2-chlorophenyl | H | Colorless needle-like crystals | 222.5–224 |

TABLE 19

| Example No. | Position of the substituted side-chain | Bonding at 3- and 4- positions | R¹ | (R²)ₘ | Position(s) of the substituted R² group | R³ (CH₂)ᵢCH(CH₂)ₙ | R⁴ | R⁵ | Crystal form | Melting point (°C.) |
|---|---|---|---|---|---|---|---|---|---|---|
| 274 | 5 | Single bond | H | Br | 8 | —CH₂— | CH₂— | H | Colorless needle-like crystals | 212–212.5 |
| 275 | 5 | Single bond | H | (I)₂ | 6, 8 | —(CH₂)₃— |  | (CH₂)₃CH₃ | Colorless needle-like crystals | 109.5–110.5 |
| 276 | 8 | Single bond | H | (Cl)₃ | 5, 6, 7 | —(CH₂)₃— |  | CH₃ | Colorless needle-like crystals | 131–132.5 |
| 277 | 8 | Single bond | H | (Cl)₂ | 6, 8 | —(CH₂)₃— |  | C₂H₅ | Colorless rhombic crystals | 130–132 |
| 278 | 5 | Single bond | H | OCH₂— | 8 | —(CH₂)₃— | 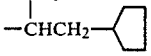 | CH₃ | Colorless prism-like crystals | 106.5–110 |
| 279 | 6 | Double bond | H | Cl | 5 | —CH₂— | CH₃<br>\|<br>—CHCH₂— | H | Colorless needle-like crystals | 225–226 |
| 280 | 6 | Double bond | H | Cl | 5 | —CH₂— |  (with CH₃ and OCH₃) | H | Colorless needle-like crystals | 311.5–313 (decomposed) |
| 281 | 6 | Double bond | H | Cl | 5 | —(CH₂)₃— |  | CH₃ | Colorless needle-like crystals | 191.5–193 |
| 282 | 6 | Double bond | CH₃ | Cl | 5 | —(CH₂)₃— |  | CH₃ | Pale-yellowish needle-like crystals | 137–138 |
| 283 | 5 | Single bond | H | OH | 8 | —(CH₂)₃— |  | CH₃ | Colorless crystals | 119–121 |

EXAMPLE 284

2.5 Grams of 6-(3-carboxypropoxy)carbostyril is suspended in 200 ml of chloroform, followed by addition of 1.5 ml of triethylamine, and then 1.2 g of thionyl chloride is added dropwise to the solution under agitation while maintaining the internal temperature at 0° to 20° C. After this addition, the mixture is agitated at the same temperature for 1 hour and then added dropwise with 2 ml of N-methylcyclohexylamine, followed by additional 3-hour agitation at room temperature. The reaction solution is washed well with a 5% aqueous K₂CO₃ solution, then further washed with water and diluted hydrochloric acid and then dried with anhydrous Na₂SO₄. After removing the solvent by distillation, the residue is refined by silica gel column chromatography (silica gel: Wakogel C-200; eluent: 10:1 chloroform/methanol (V/V)) and then recrystallized from chloroform-ethanol to obtain 0.4 g of 6-[3-(N-methyl-N-cyclohexylaminocarbonyl)propoxy]-carbostyril with melting point of 184.5°–186° C.

EXAMPLE 285

2.6 Grams of 5-(3-carboxy-2-methylpropoxy)-3,4-dihydrocarbostyril is suspended in 200 ml of methylene chloride, followed by addition of 2 ml of pyridine. Then 1.4 g of thionyl chloride is added dropwise to this mixed solution while maintaining the internal temperature at 0° to 20° C. After the end of this addition, the mixture is further agitated at the same temperature for 1 hour and then added dropwise with 2 ml of N-ethylcyclohexylamine, followed by additional 4-hour agitation at room temperature. The reaction solution is washed well with an aqueous K₂CO₃ solution and then with water and diluted hydrochloric acid and then dried with anhydrous Na$_2$SO$_4$. Thereafter, the solvent is distilled off and the resultant residue is isolated and refined by silica gel column chromatography (silica gel: Wakogel C-200; eluent: chloroform-methanol (20:1 (V/V)) and then recrystallized from ligroinbenzene to obtain 0.6 g of 5-[3-(N-cyclohexyl-N-ethylaminocarbonyl)-2-methylpropoxy]-3,4-dihydrocarbostyril in the form of colorless needle-like crystals, m.p., 114°–115.5° C.

EXAMPLES 286–316

The compounds shown in Tables 20–22 below are obtained by the method similar to Examples 284–285. The respective compounds in Table 20, Table 21 and Table 22 are expressed by the symbols given in the general formulae (1-1), (1-2) and (1-3), respectively.

TABLE 20

(1-1)

| Example No. | Position of the substituted side-chain | R$^1$ | R$^3$ / (CH$_2$)ℓCH(CH$_2$)$_n$ | R$^4$ | R$^5$ | Crystal form | Melting point (°C.) |
|---|---|---|---|---|---|---|---|
| 286 | 5 | H | —CH$_2$— | 3-Cl-4-NO$_2$-phenyl | H | Pale yellowish crystals | 286–288.5 (decomposed) |
| 287 | 5 | CH$_2$CH=CH$_2$ | —CH(CH$_3$)— | 4-OCH$_3$-phenyl | H | Colorless needle-like crystals | 141.5–142 |
| 288 | 5 | H | —(CH$_2$)$_3$— | 4-OCH$_3$-cyclohexyl | H | Colorless needle-like crystals | 207–208.5 |
| 289 | 6 | CH$_2$CH=CH$_2$ | —(CH$_2$)$_6$— | cyclohexyl | H | Colorless needle-like crystals | 104–105.5 |
| 290 | 5 | H | —(CH$_2$)$_6$— | cyclohexyl | CH$_2$-phenyl | Colorless needle-like crystals | 49–52 |
| 291 | 6 | CH$_3$ | —(CH$_2$)$_3$— | cyclohexyl | CH$_3$ | Colorless needle-like crystals | 104.5–106.5 |
| 292 | 6 | H | —(CH$_2$)$_3$— | —CH$_2$CH$_2$-(2,3-di-OCH$_3$-phenyl) | CH$_3$ | Colorless crystals | 31–35 |
| 293 | 7 | H | —CH(C$_2$H$_5$)— | cyclohexenyl | H | Colorless needle-like crystals | 182.5–183 |
| 294 | 6 | H | —(CH$_2$)$_3$— | cyclohexyl | cyclohexyl | Colorless needle-like crystals | 182–184 |
| 295 | 6 | H | —(CH$_2$)$_3$— | phenyl | (CH$_2$)$_3$CH$_3$ | Colorless rhombic crystals | 108–110 |
| 296 | 6 | H | —(CH$_2$)$_3$— | phenyl | CH$_3$ | Colorless needle-like crystals | 144–146 |

TABLE 21

$$O(CH_2)\overset{R^3}{\underset{|}{C}H}(CH_2)_nCON\overset{R^4}{\underset{R^5}{\diagdown}} \quad (1\text{-}2)$$

(quinolin-2(1H)-one with N-R¹)

| Example No. | Position of the substituted side-chain | R¹ | $\overset{R^3}{\underset{|}{(CH_2)CH(CH_2)_n}}$ | R⁴ | R⁵ | Crystal form | Melting point (°C.) |
|---|---|---|---|---|---|---|---|
| 297 | 8 | H | —CH₂— | —CH₂-cyclohexyl | H | Colorless needle-like crystals | 192.5–193.5 |
| 298 | 6 | H | —CH(CH₃)— | cyclohexyl | CH₃ | Colorless plate-like crystals | 172–176 |
| 299 | 6 | H | —(CH₂)₃— | 3-methylcyclohexyl | C₂H₅ | Colorless plate-like crystals | 150.5–153 |
| 300 | 6 | H | —(CH₂)₃— | cyclohexyl | —CH₂CH₂-phenyl | Colorless plate-like crystals | 163.5–164.5 |
| 301 | 6 | H | —CH₂CH(CH₃)CH₂— | cyclohexyl | CH₃ | Colorless needle-like crystals | 146–149 |
| 302 | 6 | CH₂-phenyl | —(CH₂)₃— | cyclohexyl | CH₃ | Colorless needle-like crystals | 107.5–108.5 |
| 303 | 6 | H | —(CH₂)₃— | 4-methoxycyclohexyl | H | Colorless crystals | 202.5–206 |
| 304 | 6 | CH₃ | —(CH₂)₃— | cyclohexyl | CH₃ | Colorless needle-like crystals | 118.5–119.5 |
| 305 | 6 | H | —(CH₂)₃— | cyclohexyl | CH₂-phenyl | Colorless needle-like crystals | 185.5–187 |
| 306 | 5 | CH₃ | —CH(CH₃)— | cyclopropyl | H | Colorless needle-like crystals | 189–190 |
| 307 | 5 | H | —CH₂— | —CH(CH₃)CH₂-cyclopentyl | H | Colorless needle-like crystals | 202–204.5 |

TABLE 22

$$O(CH_2)\overset{R^3}{\underset{|}{C}H}(CH_2)_nCON\overset{R^4}{\underset{R^5}{\diagdown}} \quad (1\text{-}3)$$

(with $(R^2)_m$ substituents on quinolin-2(1H)-one, N-R¹)

| Example No. | Position of the substituted side-chain | Bonding at 3- and 4-positions | R¹ | (R²)ₘ | Position(s) of the substituted R² group | $\overset{R^3}{\underset{|}{(CH_2)CH(CH_2)_n}}$ | R⁴ | R⁵ | Crystal form | Melting point (°C.) |
|---|---|---|---|---|---|---|---|---|---|---|
| 308 | 5 | Single bond | H | Br | 8 | —CH₂— | —CH₂-cyclohexyl | H | Colorless needle-like crystals | 212–212.5 |
| 309 | 5 | Single bond | H | (I)₂ | 6, 8 | —(CH₂)₃— | phenyl | (CH₂)₃CH₃ | Colorless needle-like crystals | 109.5–110.5 |

TABLE 22-continued

(1-3)

| Example No. | Position of the substituted side-chain | Bonding at 3- and 4-positions | R¹ | (R²)ₘ | Position(s) of the substituted R² group | $R^3$<br>$\|$<br>$(CH_2)_l CH(CH_2)_n$ | R⁴ | R⁵ | Crystal form | Melting point (°C.) |
|---|---|---|---|---|---|---|---|---|---|---|
| 310 | 8 | Single bond | H | (Cl)₃ | 5<br>6<br>7 | —(CH₂)₃— |  | CH₃ | Colorless needle-like crystals | 131–132.5 |
| 311 | 5 | Single bond | H | (Cl)₂ | 6<br>8 | —(CH₂)₃— |  | C₂H₅ | Colorless rhombic crystals | 130–132 |
| 312 | 5 | Single bond | H | OCH₂—⟨⟩ | 8 | —(CH₂)₃— |  | CH₃ | Colorless prism-like crystals | 106.5–110 |
| 313 | 6 | Double bond | H | Cl | 5 | —CH₂— | CH₃<br>$\|$<br>—CHCH₂— | H | Colorless needle-like crystals | 225–226 |
| 314 | 6 | Double bond | H | Cl | 5 | —CH₂— | 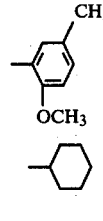 | H | Colorless needle-like crystals | 311.5–313 (decomposed) |
| 315 | 6 | Double bond | H | Cl | 5 | —(CH₂)₃— |  | CH₃ | Colorless needle-like crystals | 191.5–193 |
| 316 | 6 | Double bond | CH₃ | Cl | 5 | —(CH₂)₃— |  | CH₃ | Pale-yellowish needle-like crystals | 137–138 |

EXAMPLE 317

3.2 Grams of 6-hydroxy-3,4-dihydrocarbostyril, 0.9 g of potassium hydroxide, 3.2 g of sodium iodide and 5.0 g of N-methyl-N-(4-chlorobutyryl)cyclohexylamine are added to 50 ml of dimethylsulfoxide, and the mixture is agitated at 70° to 80° C. for 4.5 hours. After the reaction, the reaction solution is poured into 400 ml of saturated NaCl solution and the precipitated crystals are filtered out and washed with water. The thus obtained crude crystals are then recrystallized from benzene-petroluem ether to obtain 2.9 g of 6-[3-(N-methyl-N-cyclohexylaminocarbonyl)propoxy]-3,4-dihydrocarbostyril in the form of colorless needlelike crystals with melting point of 144°–146° C.

EXAMPLE 318

1.6 Grams of 5-hydroxy-3,4-dihydrocarbostyril, 0.8 g of pyridine, 1.8 g of potassium iodide and 2.8 g of N-methyl-N-(4-chlorobutyryl)cyclohexylamine are added to 30 ml of dioxane, and the mixture is refluxed under agitation for 12 hours. After the reaction, the reaction solution is poured into 200 ml of saturated NaCl solution and the precipitated crystals are filtered out. The crude crystals are dissolved in 50 ml of chloroform and the organic layer is washed with 1 N sodium hydroxide (50 ml×2), water and then, dried with anhydrous sodium sulfate, followed by removal of the solvent by distillation, and the resultant residue is recrystallized from ethyl acetate to obtain 0.8 g of 5-[3-(N-methyl-N-cyclohexylaminocarbonyl)propoxy]-3,4-dihydrocarbostyril in the form of colorless prism-like crystals with melting point of 133°–134° C.

EXAMPLE 319

1.6 Grams of 6-hydroxycarbostyril, 0.7 g of sodium ethylate, 1.6 g of sodium iodide and 2.4 g of N-methyl-N-(4-chlorobutyryl)aniline are added to 30 ml of ethanol and refluxed under agitation for 6 hours. After the reaction, the reaction solution is poured into 200 ml of saturated NaCl solution and the precipitated crystals are filtered out and washed with water. The obtained crude crystals are recrystallized from chloroform-petroleum ether to obtain 1.3 g of 6-[3-(N-methylanilinocarbonyl)propoxy]carbostyril in the form of colorless needle-like crystals with melting point of 187°–189° C.

EXAMPLE 320

0.5 Gram of metallic sodium is dissolved in 50 ml of methanol under ice cooling, and to this solution is added 3.2 g of 6-hydroxy-3,4-dihydrocarbostyril, 3.2 g of sodium iodide and 4.6 g of N-(4-chlorobutyryl)cyclohexylamine, followed by 5-hour refluxing under agitation. After the reaction, the reaction solution is poured into 400 ml of saturated NaCl solution and the precipitated crystals are filtered out and washed with water. The resultant crude crystals are recrystallized from methanol to obtain 3.1 g of 6-[3-(N-cyclohexylaminocarbonyl)propoxy]-3,4-dihydrocarbostyril in the form of colorless needle-like crystals with melting point of 220°–221° C.

EXAMPLE 321

1.6 Grams of 6-hydroxycarbostyril, 1.4 g of $K_2CO_3$, 1.6 g of sodium iodide and 2.5 g of N-methyl-N-(4-chlorobutyryl)cyclohexylamine are added to 30 ml of DMF and the mixture is agitated at 70° to 80° C. for 4 hours. After the reaction, the reaction solution is poured into 200 ml of saturated NaCl solution and the precipitated crystals are filtered out and washed with water. The resultant crude crystals are recrystallized from chloroformethanol to obtain 1.5 g of 6-[3-(N-methyl-N-cyclohexylaminocarbonyl)propoxy]carbostyril in the form of colorless needle-like crystals with melting point of 184.5°–186° C.

EXAMPLES 322–384

The compounds shown in Table 23 below are obtained according to the procedure of Examples 317–321.

TABLE 23

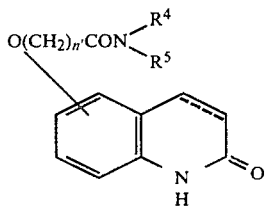

| Example No. | Position of the substituted side-chain | Bonding at 3- and 4- positions | n' | $R^4$ | $R^5$ | Crystal form | Melting point (°C.) |
|---|---|---|---|---|---|---|---|
| 322 | 5 | Single bond | 3 | –cyclohexyl | –$CH_2CH=CH_2$ | Colorless needle-like crystals | 116.5–118 |
| 323 | 5 | Single bond | 3 | –phenyl | –$C_2H_5$ | Colorless needle-like crystals | 179.5–180.5 |
| 324 | 5 | Single bond | 3 | Cl-phenyl | H | Colorless needle-like crystals | 211–212.5 |
| 325 | 5 | Double bond | 3 | –cyclohexyl | –$CH_3$ | Colorless needle-like crystals | 172.5–174 |
| 326 | 5 | Double bond | 3 | –phenyl | –$C_2H_5$ | Colorless needle-like crystals | 216.5–218.5 |
| 327 | 5 | Single bond | 4 | –cyclohexyl | –$(CH_2)_3CH_3$ | Colorless needle-like crystals | 121–123.5 |
| 328 | 6 | Single bond | 1 | –cyclohexyl | –$C_2H_5$ | Colorless rhombic crystals | 133–135 |
| 329 | 6 | Single bond | 1 | –phenyl | –$(CH_2)_3CH_3$ | Colorless rhombic crystals | 111–113 |
| 330 | 6 | Single bond | 1 | –phenyl-$OCH_3$ | H | Colorless needle-like crystals | 197–198 |
| 331 | 6 | Single bond | 1 | –cycloheptyl | H | Colorless needle-like crystals | 191.5–192.5 |
| 332 | 6 | Single bond | 3 | –cyclohexyl | –$CH_2CH=CH_2$ | Colorless needle-like crystals | 105–107 |
| 333 | 6 | Single bond | 3 | –cyclohexyl | –cyclohexyl | Colorless needle-like crystals | 182–184 |
| 334 | 6 | Single bond | 3 | –phenyl | H | Colorless plate-like crystals | 186–187 |
| 335 | 6 | Single bond | 3 | –phenyl | –$CH_3$ | Colorless needle-like crystals | 129.5–131.5 |
| 336 | 6 | Single bond | 3 | –phenyl | –$(CH_2)_3CH_3$ | Colorless rhombic crystals | 108–110 |
| 337 | 6 | Single bond | 3 | –phenyl | –phenyl | Colorless needle-like crystals | 201–205 |

TABLE 23-continued

| Example No. | Position of the substituted side-chain | Bonding at 3- and 4- positions | n' | R⁴ | R⁵ | Crystal form | Melting point (°C.) |
|---|---|---|---|---|---|---|---|
| 338 | 6 | Single bond | 3 | cyclopropyl | H | Colorless needle-like crystals | 186–187.5 |
| 339 | 6 | Single bond | 3 | –C₆H₄–NHCOCH₃ | H | Colorless needle-like crystals | 265–266 (decomposed) |
| 340 | 6 | Single bond | 3 | –C₆H₄–OH | H | Colorless rhombic crystals | 214–215 (decomposed) |
| 341 | 6 | Single bond | 4 | cyclohexyl | –(CH₂)₃CH₃ | Colorless needle-like crystals | 109.5–111.5 |
| 342 | 6 | Single bond | 4 | phenyl | –CH₃ | Colorless rhombic crystals | 129.5–131 |
| 343 | 6 | Single bond | 4 | 2,3-dimethylphenyl | H | Colorless needle-like crystals | 183–184.5 |
| 344 | 6 | Double bond | 3 | cyclohexyl | H | Colorless needle-like crystals | 251–252 |
| 345 | 6 | Double bond | 3 | cyclohexyl | –C₂H₅ | Colorless needle-like crystals | 167.5–169 |
| 346 | 6 | Double bond | 3 | cyclohexyl | –CH(CH₃)₂ | Colorless needle-like crystals | 174–175 |
| 347 | 6 | Double bond | 3 | cyclohexyl | –(CH₂)₃CH₃ | Colorless needle-like crystals | 159–160 |
| 348 | 6 | Double bond | 3 | cyclohexyl | cyclohexyl | Colorless needle-like crystals | 228.5–230.5 |
| 349 | 6 | Double bond | 3 | cyclohexyl | phenyl | Colorless needle-like crystals | 180–181.5 |
| 350 | 6 | Double bond | 3 | 2,3-dimethylphenyl | H | Colorless needle-like crystals | 251.5–253 |
| 351 | 6 | Double bond | 3 | phenyl | –C₂H₅ | Colorless needle-like crystals | 115.5–117 |
| 352 | 6 | Double bond | 3 | phenyl | –(CH₂)₃CH₃ | Colorless needle-like crystals | 159–160.5 |
| 353 | 6 | Double bond | 3 | 2-methylphenyl | –CH₃ | Colorless needle-like crystals | 143–143.5 |
| 354 | 6 | Double bond | 3 | 2-chlorophenyl | H | Colorless needle-like crystals | 222.5–224 |
| 355 | 6 | Double bond | 3 | 4-methoxyphenyl | H | Colorless needle-like crystals | 236–237 |

TABLE 23-continued $$O(CH_2)_{n'}CON\begin{matrix}R^4\\R^5\end{matrix}$$

[Structure: quinolin-2(1H)-one with O(CH2)n'CON(R4)(R5) substituent]

| Example No. | Position of the substituted side-chain | Bonding at 3- and 4- positions | n' | $R^4$ | $R^5$ | Crystal form | Melting point (°C.) |
|---|---|---|---|---|---|---|---|
| 356 | 6 | Double bond | 4 | cyclohexyl | $-(CH_2)_3CH_3$ | Colorless needle-like crystals | 151–153.5 |
| 357 | 5 | Single bond | 3 | 4-Br-phenyl | H | Colorless needle-like crystals | 241.5–242 |
| 358 | 5 | Single bond | 3 | 3-OH-phenyl | H | Colorless needle-like crystals | 206–207 |
| 359 | 5 | Single bond | 6 | phenyl | $C_2H_5$ | Colorless plate-like crystals | 129–131.5 |
| 360 | 5 | Double bond | 3 | phenyl | $CH_3$ | Colorless flake crystals | 223–225 (decomposed) |
| 361 | 5 | Double bond | 3 | 2-OCH3-phenyl | H | Colorless plate-like crystals | 171–175 |
| 362 | 5 | Double bond | 3 | 4-(CH2)2CH3-phenyl | H | Colorless needle-like crystals | 241–242 (decomposed) |
| 363 | 6 | Single bond | 1 | 4-C2H5-phenyl | H | Colorless needle-like crystals | 202.5–204 |
| 364 | 6 | Double bond | 1 | cyclohexyl | $CH_3$ | Pale-yellowish needle-like crystals | 131–133.5 |
| 365 | 6 | Single bond | 3 | 4-OH-phenyl | $CH_3$ | Colorless needle-like crystals | 108–112 |
| 366 | 6 | Single bond | 3 | 3-CH3-phenyl | $C_2H_5$ | Colorless needle-like crystals | 110–111.5 |
| 367 | 6 | Double bond | 3 | 3,4-di-OCH3-phenyl | H | Colorless needle-like crystals | 209–210 |
| 368 | 6 | Double bond | 3 | cyclohexyl | $CH_2CH_2CH_3$ | Colorless needle-like crystals | 182–184.5 |
| 369 | 6 | Double bond | 4 | cyclohexyl | $(CH_2)_3CH_3$ | Colorless needle-like crystals | 151–153.5 |
| 370 | 6 | Single bond | 6 | cyclohexyl | $C_2H_5$ | Colorless needle-like crystals | 111–112.5 |
| 371 | 6 | Single bond | 6 | phenyl | $CH_2CH_2CH_3$ | Colorless needle-like crystals | 90.5–92 |
| 372 | 7 | Single bond | 3 | cyclohexyl | $CH_3$ | Colorless rhombic crystals | 114.5–117 |
| 373 | 8 | Double bond | 1 | CH3O-(2,4-di-CH3)-phenyl | H | Colorless needle-like crystals | 235–236 |

TABLE 23-continued

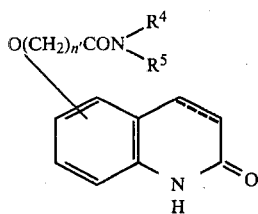

| Example No. | Position of the substituted side-chain | Bonding at 3- and 4- positions | n' | R$^4$ | R$^5$ | Crystal form | Melting point (°C.) |
|---|---|---|---|---|---|---|---|
| 374 | 8 | Double bond | 1 | cyclohexyl | CH$_3$ | Colorless rhombic crystals | 176–178 |
| 375 | 8 | Single bond | 3 | cyclohexyl | CH$_3$ | Colorless rhombic crystals | 141–142 |
| 376 | 8 | Single bond | 3 | 2,4-dichlorophenyl | H | Colorless rhombic crystals | 193–195.5 |
| 377 | 6 | Double bond | 3 | cyclopropyl | C$_2$H$_5$ | Colorless needle-like crystals | 150–152 |
| 378 | 6 | Double bond | 3 | cyclopentyl | C$_2$H$_5$ | Colorless needle-like crystals | 158–160 |
| 379 | 6 | Double bond | 3 | cycloheptyl | C$_2$H$_5$ | Colorless needle-like crystals | 145–147 |
| 380 | 6 | Double bond | 3 | cyclooctyl | C$_2$H$_5$ | Colorless needle-like crystals | 143–144.5 |
| 381 | 6 | Double bond | 3 | cyclohexyl | (CH$_2$)$_4$CH$_3$ | Colorless needle-like crystals | 156.5–157.5 |
| 382 | 6 | Double bond | 3 | cyclohexyl | (CH$_2$)$_5$CH$_3$ | Colorless needle-like crystals | 129–132 |
| 383 | 6 | Double bond | 3 | cyclohexyl | (CH$_2$)$_7$CH$_3$ | Colorless crystals | 100–103 |
| 384 | 6 | Single bond | 3 | cyclohexyl | (CH$_2$)$_3$CH$_3$ | Colorless rhombic crystals | 142–143.5 |

EXAMPLE 385

1.6 Grams of 6-hydroxy-3,4-dihydrcarbostyril, 1.4 g of K$_2$CO$_3$, 1.6 g of sodium iodide and 2.7 g of N-(4-chlorobutyryl)-2-cyclopentyl-1-methylethylamine are added to 30 ml of dimethylformamide, and the mixture is agitated at 70° to 80° C. for 3.5 hours. After the reaction, the reaction solution is poured into 200 ml of saturated NaCl solution and the precipitated crystals are filtered out and washed with water. The resultant crystals are recrystallized from chloroform-petroleum ether to obtain 3.4 g of 6-{3-[N-(2-cyclopentyl-1-methylethylaminocarbonyl]propoxy}-3,4-dihydrocarbostyril in the form of colorless needle-like crystals with melting point of 138°–139.5° C.

EXAMPLES 386–388

The compounds of Table 24 below are obtained in the same way as Example 385.

TABLE 24

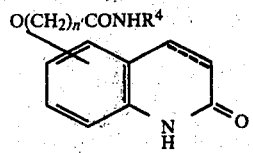

| Example No. | Bonding at 3- and 4- positions | n' | R$^4$ | Crystal form | Melting point (°C.) |
|---|---|---|---|---|---|
| 386 | Single bond | 3 | —CH$_2$—cyclohexyl | Colorless needle-like crystals | 170–172 |
| 387 | Single bond | 1 | —CH$_2$—cyclohexyl | Colorless needle-like crystals | 174.5–176 |
| 388 | Double bond | 3 | —CH(CH$_3$)CH$_2$—cyclobutyl | Colorless needle-like crystals | 173–175 |

EXAMPLE 389

1.75 Grams of 1-methyl-6-hydroxycarbostyril, 1.8 g of $K_2CO_3$ and 0.5 g of KI are added to 50 ml of DMF, and then 2.8 g of N-methyl-N(4-chlorobutyryl)cyclohexylamine is added gradually dropwise to this solution at 60° to 70° C. under agitation, followed by additional 4-hour agitation at the same temperature and removal of the solvent by distillation. The residue is dissolved in 200 ml of chloroform, washed with diluted hydrochloric acid, a 1% aqueous NaOH solution and water and then dried with anhydrous $Na_2SO_4$. After filtering off the inorganic matter, the mother liquor is concentrated and the residue is crystallized from petroleum ether. The obtained crystals are recrystallized from benzene-ligroin to produce 0.6 g of 1-methyl-6-[3-(N-cyclohexyl-N-methylaminocarbonyl)-propoxy]carbostyril in the form of colorless needle-like crystals with melting point of 118.5°–119.5° C.

EXAMPLE 390

3.4 Grams of 1-methyl-6-hydroxy-3,4-dihydrocarbostyril, 0.9 g of potassium hydroxide, 3.2 g of sodium iodide and 5.0 g of N-methyl-N-(4-chlorobutyryl)-cyclohexylamine are added to 50 ml of dimethylsulfoxide and agitated at 70° to 80° C. for 4.5 hours. After the reaction, the reaction solution is poured into 400 ml of saturated NaCl solution and the precipitated crystals are filtered out and washed with water. The resultant crude crystals are recrystallized from ligroin to obtain 3.1 g of 1-methyl-6-[3-(N-cyclohexyl-N-methylaminocarbonyl)propoxy]-3,4-dihydrocarbostyril in the form of colorless needle-like crystals with melting point of 104.5°–106.5° C.

EXAMPLE 391

1.6 Grams of 5-hydroxy-3,4-dihydrocarbostyril, 0.8 g of pyridine, 1.8 g of potassium iodide and 3.1 g of N-ethyl-N-(4-chloro-3-methylbutyryl)cyclohexylamine are added to 30 ml of dioxane and the mixture is refluxed under agitation for 12 hours. After the reaction, the reaction solution is poured into 200 ml of saturated NaCl solution and the precipitated crystals are filtered out. The crude crystals are dissolved in 50 ml of chloroform and the organic layer is washed with 1 N NaOH (50 ml×2), water and dried with anhydrous $Na_2SO_4$, followed by removal of the solvent by distillation. The resultant residue is recrystallized from ligroin-benzene to produce 0.9 g of 5-[3-(N-ethyl-N-cyclohexylamiocarbonyl)-2-methylpropoxy]-3,4-dihydrocarbostyril in the form of colorless needle-like crystals with melting point of 114°–115.5° C.

EXAMPLE 392

0.5 Gram of metallic sodium is dissolved in 50 ml of methanol under ice cooling, followed by addition thereto of 3.4 g of 1-methyl-6-hydroxy-3,4-dihydrocarbostyril, 3.2 g of sodium iodide and 5.0 g of N-methyl-N-(4-chlorobutyryl)cyclohexylamine and 4.5-hour reflux under agitation. After the reaction, the reaction solution is poured into 400 ml of saturated NaCl solution and the precipitated crystals are filtered out and washed with water. The resultant crude crystals are recrystallized from ligroin to produce 2.9 g of 1-methyl-6-[3-(N-cyclohexyl-N-methylaminocarbonyl)propoxy]-3,4-dihydrocarbostyril in the form of colorless needle-like crystals with melting point of 104.5°–106.5° C.

EXAMPLE 393

1.6 Grams of 6-hydroxycarbostyril, 0.7 g of sodium ethylate, 1.6 g of sodium iodide and 3.3 g of N-ethyl-N-(4-chloro-3-methylbutyryl)-2-methylcyclohexylamine are added to 30 ml of ethanol and the mixture is refluxed under agitation for 5 hours. After the reaction, the reaction solution is poured into 200 ml of saturated NaCl solution and the precipitated crystals are filtered out and washed with water. The resultant crude crystals are recrystallized from benzene-ligroin to obtain 1.4 g of 6-{3-[N-methyl-N-(2-methylcyclohexyl)aminocarbonyl]-2-methylpropoxy}carbostyril with melting point of 146°–149° C.

EXAMPLE 394

1.6 Grams of 6-hydroxycarbostyril, 1.4 g of $K_2CO_3$, 1.6 g of sodium iodide and 3.3 g of N-ethyl-N-(4-chloro-3-methylbutyryl)-2-methylcyclohexylamine are added to 30 ml of DMF and agitated at 70° to 80° C. for 4.5 hours. After the reaction, the reaction solution is poured into 200 ml of saturated NaCl solution and the precipitated crystals are filtered out and washed with water. The resultant crude crystals are recrystallized from benzene-ligroin to produce 1.4 g of 6-{3-[N-methyl-N-(2-methylcyclohexyl)aminocarbonyl]-2-methylpropoxy}carbostyril with melting point of 146°–149° C.

EXAMPLES 395–469

The compounds in Tables 25–27 below are obtained from the procedures of Examples 389–394. The respective compounds in these tables are expressed by the symbols given in the general formulae (1-1), (1-2) and (1-3), respectively.

TABLE 25

(1-1)

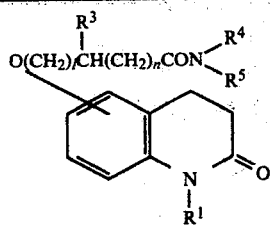

| Example No. | Position of the substituted side-chain | $R^1$ | $R^3$ $(CH_2)CH(CH_2)_n$ | $R^4$ | $R^5$ | Crystal form | Melting point (°C.) |
|---|---|---|---|---|---|---|---|
| 395 | 5 | H | $-CH_2-$ | 3-Cl-4-NO$_2$-C$_6$H$_3$- | H | Pale-yellowish crystals | 286–288.5 (decomposed) |
| 396 | 5 | CH$_3$ | " | 3-OC$_2$H$_5$-C$_6$H$_4$- | H | Colorless needle-like crystals | 186–187 |
| 397 | 5 | CHCH$_2$=CH$_2$ | $-CH(CH_3)-$ | 4-OCH$_3$-C$_6$H$_4$- | H | Colorless needle-like crystals | 141.5–142 |
| 398 | 5 | H | " | 2-COOC$_2$H$_5$-C$_6$H$_4$- | H | Colorless needle-like crystals | 186–189 |
| 399 | 5 | H | " | 2-CONHCH$_3$-C$_6$H$_4$- | H | Colorless flake-like crystals | 211–212 |
| 400 | 5 | H | $-CH(C_2H_5)-$ | 4-CH$_3$-cyclohexyl | C$_2$H$_5$ | Colorless needle-like crystals | 159–161 |
| 401 | 5 | H | $-(CH_2)_2-$ | $-CH_2-$cyclohexyl | H | Colorless needle-like crystals | 190.5–192 |
| 402 | 5 | H | $-(CH_2)_3-$ | 4-OCH$_3$-cyclohexyl | H | Colorless needle-like crystals | 207–208.5 |
| 403 | 5 | H | " | 4-SO$_2$NH$_2$-C$_6$H$_4$- | H | Colorless needle-like crystals | 270–274 (decomposed) |
| 404 | 5 | H | " | 2-COCH$_3$-C$_6$H$_4$- | H | Colorless needle-like crystals | 212–213 |
| 405 | 5 | H | " | 4-OH-cyclohexyl | CH$_3$ | Colorless needle-like crystals | 169–172 |
| 406 | 5 | C$_2$H$_5$ | " | $-CH_2CH_2-$(3,4-(OCH$_3$)$_2$-C$_6$H$_3$) | H | Colorless needle-like crystals | 122.5–124 |
| 407 | 5 | " | " | $-CH_2-$cyclohexyl | H | Colorless needle-like crystals | 141.5–143 |
| 408 | 5 | H | $-(CH_2)_6-$ | cyclohexyl | CH$_2$C$_6$H$_5$ | Colorless needle-like crystals | 49–52 |
| 409 | 5 | H | $-CH_2CH(CH_3)CH_2-$ | 2-CONH$_2$-C$_6$H$_4$- | H | Colorless needle-like crystals | 181–182.5 |
| 410 | 6 | H | $-(CH_2)_3-$ | 4-N(CH$_3$)$_2$-C$_6$H$_4$- | H | Colorless needle-like crystals | 211.5–213 |
| 411 | 6 | H | " | 4-OCOCH$_3$-C$_6$H$_4$- | CH$_3$ | Colorless needle-like crystals | 129.5–132.5 |

TABLE 25-continued (1-1)

$$O(CH_2)CH(CH_2)_nCON\begin{subarray}{l}R^4\\R^5\end{subarray}$$ substituent on tetrahydroquinolin-2(1H)-one with $R^3$ and $R^1$ on N

| Example No. | Position of the sub-stituted side-chain | $R^1$ | $(CH_2)CH(CH_2)_n$ with $R^3$ | $R^4$ | $R^5$ | Crystal form | Melting point (°C.) |
|---|---|---|---|---|---|---|---|
| 412 | 6 | H | " | —CH₂CH₂—(2,3-dimethoxyphenyl) with OCH₃, OCH₃ | " | Colorless crystals | 31–35 |
| 413 | 6 | CH₂CH=CH₂ | —(CH₂)₆— | cyclohexyl | H | Colorless needle-like crystals | 104–105.5 |
| 414 | 7 | H | —CH— with C₂H₅ | cycloheptyl | H | Colorless needle-like crystals | 182.5–183 |
| 415 | 5 | H | —(CH₂)₃— | cyclohexyl-CONH₂ | H | Colorless needle-like crystals | 236–239 (decomposed) |
| 416 | 5 | H | —CH₂CHCH₂— with OH | cyclohexyl | H | Colorless needle-like crystals | 156–158 |
| 417 | 6 | H | —(CH₂)₃— | cyclohexyl-OH | cyclopropyl | Colorless needle-like crystals | 160–161 |
| 418 | 6 | H | " | cyclohexyl-Cl | —CH₂-cyclohexyl | Colorless needle-like crystals | 166–168 |
| 419 | 6 | H | " | cyclohexyl-NHCOCH₃ | H | Colorless needle-like crystals | 298–299 (decomposed) |
| 420 | 6 | H | " | cyclohexyl-N(CH₃)₂ | H | Colorless crystals | 235–238 |

TABLE 26

(1-2)

$$O(CH_2)CH(CH_2)_nCON\begin{subarray}{l}R^4\\R^5\end{subarray}$$ substituent on quinolin-2(1H)-one with $R^3$ and $R^1$ on N

| Example No. | Position of the sub-stituted side-chain | $R^1$ | $(CH_2)CH(CH_2)_n$ with $R^3$ | $R^4$ | $R^5$ | Crystal form | Melting point (°C.) |
|---|---|---|---|---|---|---|---|
| 421 | 5 | H | —CH₂— | 3-acetylphenyl (COCH₃) | H | Yellowish plate-like crystals | 183–186 |
| 422 | 5 | H | " | —CH₂CH₂—(2,3-dimethoxyphenyl) with OCH₃, OCH₃ | H | Colorless plate-like crystals | 181.5–185 |

TABLE 26-continued (1-2)

Structure: O(CH₂)CH(CH₂)ₙCONR⁴R⁵ substituted quinolin-2(1H)-one with R³ on side-chain carbon and R¹ on N.

| Example No. | Position of the substituted side-chain | R¹ | R³ / (CH₂)/CH(CH₂)ₙ | R⁴ | R⁵ | Crystal form | Melting point (°C.) |
|---|---|---|---|---|---|---|---|
| 423 | 5 | H | " | −CHCH₂−cyclopentyl with CH₃ | H | Colorless needle-like crystals | 202–204.5 |
| 424 | 5 | CH₃ | −CH− with CH₃ | cyclopropyl | H | Colorless needle-like crystals | 189–190 |
| 425 | 5 | H | −(CH₂)₃− | −CH₂CH₂−(3,4-dimethoxyphenyl) | H | Colorless flake-like crystals | 168.5–171 |
| 426 | 5 | H | " | −CH₂−cyclohexyl | H | Colorless flake-like crystals | 236.5–237 (decomposed) |
| 427 | 6 | H | −CH− with CH₃ | cyclohexyl | CH₃ | Colorless plate-like crystals | 172–176 |
| 428 | 6 | H | −(CH₂)₃− | 4-hydroxycyclohexyl | H | Colorless needle-like crystals | 255–257 |
| 429 | 6 | CH₂−phenyl | " | cyclohexyl | CH₃ | Colorless needle-like crystals | 107.5–108.5 |
| 430 | 6 | H | " | 4-hydroxycyclohexyl | CH₃ | Colorless needle-like crystals | 199–201 |
| 431 | 6 | H | " | 4-methoxycyclohexyl | H | Colorless crystals | 202.5–206 |
| 432 | 6 | H | " | 2-(ethoxycarbonyl)phenyl | H | Colorless needle-like crystals | 184–185 |
| 433 | 6 | H | " | cyclohexyl | CH₂−phenyl | Colorless needle-like crystals | 185.5–187 |
| 434 | 6 | H | " | 4-acetoxycyclohexyl | CH₃ | Colorless crystals | 187–190 |
| 435 | 6 | H | " | 3-methylcyclohexyl | C₂H₅ | Colorless needle-like crystals | 150.5–153 |
| 436 | 6 | H | " | cyclohexyl | CH₂CH₂−phenyl | Colorless needle-like crystals | 163.5–164.5 |
| 437 | 6 | H | −CH₂CHCH₂− with CH₃ | phenyl | CH₂CH₂CH₃ | Colorless plate-like crystals | 134.5–137.5 |
| 438 | 8 | H | −CH₂− | −CH₂−cyclohexyl | H | Colorless needle-like crystals | 192.5–193.5 |
| 439 | 6 | H | −(CH₂)₃− | 2-carbamoylcyclohexyl | H | Colorless needle-like crystals | 122–124 |
| 440 | 6 | H | " | 3-methylcyclohexyl | CH₃ | Colorless needle-like crystals | 137–140 |

TABLE 26-continued

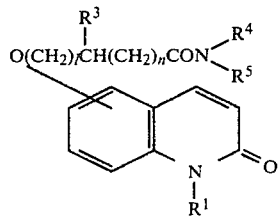

(1-2)

| Example No. | Position of the sub- stituted side-chain | R¹ | $R^3$<br>$(CH_2)_l\overset{\|}{C}H(CH_2)_n$ | R⁴ | R⁵ | Crystal form | Melting point (°C.) |
|---|---|---|---|---|---|---|---|
| 441 | 6 | H | " | —CH₂CH₂—C₆H₃(OCH₃)₂ (with OCH₃ groups) | cyclohexyl | Colorless crystals | 78–81 |
| 442 | 6 | H | " | cyclohexyl-NH₂ | H | Pale-yellowish crystals | 157–160 |
| 443 | 6 | H | " | cyclohexyl-NHCOCH₃ | H | Colorless needle-like crystals | 105–109 |
| 444 | 6 | H | —CH₂CH(CH₃)CH₂— | cyclohexyl | CH₃ | Colorless needle-like crystals | 180–182 |
| 445 | 6 | H | —CH₂CH(OH)CH₂— | cyclohexyl | H | Colorless needle-like crystals | 201–203 |
| 446 | 6 | H | —(CH₂)₃— | —CH₂CH₂—C₆H₃(OCH₃)₂ | CH₃ | Colorless needle-like crystals | 127.5–129.5 |
| 447 | 6 | H | " | —CH(CH₃)CH₂—cyclopentyl | C₂H₅ | Colorless rhombic crystals | 105–107 |
| 448 | 6 | H | " | CH₂—cyclohexyl | CH₃ | Colorless needle-like crystals | 166.5–168 |
| 449 | 6 | H | " | cyclohexyl-Cl | (CH₂)₇CH₃ | Colorless needle-like crystals | 127–128.5 |
| 450 | 6 | H | " | cyclohexyl-CH₃ | " | Colorless crystals | 63.5–66.0 |
| 451 | 6 | H | " | cyclohexyl-OH | " | Colorless crystals | 86.0–89.5 |

TABLE 27

(1-3)

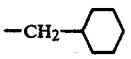

| Example No. | Position of the substituted side-chain | Bonding at 3- and 4- positions | $R^1$ | $(R^2)_m$ | Positions of the substituted $R^2$ group | $(CH_2)_l\overset{R^3}{C}H(CH_2)_n$ | $R^4$ | $R^5$ | Crystal form | Melting point (°C.) |
|---|---|---|---|---|---|---|---|---|---|---|
| 452 | 5 | Single bond | H | Br | 8 | —CH$_2$— | 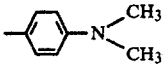 | H | Colorless needle-like crystals | 212–212.5 |
| 453 | 5 | Single bond | H | Br | " | " |  | H | Colorless needle-like crystals | 258–259.5 |
| 454 | 5 | Single bond | H | Br | " | —(CH$_2$)$_3$— |  | CH$_3$ | Colorless needle-like crystals | 134–135 |
| 455 | 5 | Single bond | H | Br | " | " | 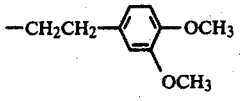 | H | Colorless needle-like crystals | 260.5–261 (decomposed) |
| 456 | 5 | Single bond | H | I | " | " | —CH$_2$CH$_2$— | H | Colorless needle-like crystals | 190–191 |
| 457 | 5 | Single bond | H | (I)$_2$ | 6 8 | " |  | —(CH$_2$)$_3$CH$_3$ | Colorless needle-like crystals | 109.5–110.5 |
| 458 | 5 | Single bond | H | (Cl)$_2$ | 6 8 | " |  | C$_2$H$_5$ | Colorless rhombic crystals | 130–132 |
| 459 | 5 | Single bond | H | (Cl)$_2$ | 6 8 | " | 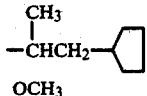 | H | Colorless rhombic crystals | 270–271 (decomposed) |
| 460 | 6 | Double bond | H | Cl | 5 | —CH$_2$— | 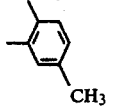 | H | Colorless rhombic crystals | 225–226 |
| 461 | 6 | Double bond | H | Cl | " | " |  | H | Colorless needle-like crystals | 311.5–313 (decomposed) |
| 462 | 6 | Double bond | H | Cl | " | —(CH$_2$)$_3$— |  | CH$_3$ | Colorless needle-like crystals | 179–180.5 |
| 463 | 6 | Double bond | H | Cl | " | " |  | " | Colorless needle-like crystals | 191.5–193 |
| 464 | 6 | Double bond | CH$_3$ | Cl | " | " |  | " | Pale-yellowish needle-like crystals | 137–138 |
| 465 | 6 | Double bond | H | Cl | " | " |  | C$_2$H$_5$ | Colorless needle-like crystals | 134.5–136 |
| 466 | 8 | Single bond | H | (Cl)$_3$ | 5 6 7 | " |  | CH$_3$ | Colorless needle-like crystals | 131–132.5 |

TABLE 27-continued

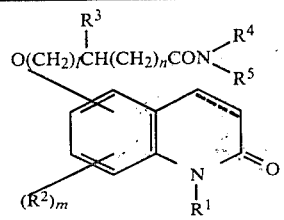

(1-3)

| Example No. | Position of the substituted side-chain | Bonding at 3- and 4-positions | R¹ | (R²)ₘ | Positions of the substituted R² group | R³ (CH₂)ₚCH(CH₂)ₙ | R⁴ | R⁵ | Crystal form | Melting point (°C.) |
|---|---|---|---|---|---|---|---|---|---|---|
| 467 | 6 | Double bond | H | Cl | 5 | " | ◯ | —(CH₂)₃CH₃ | Colorless needle-like crystals | 178.5–179.5 |
| 468 | 5 | Single bond | H | OCH₂—◯ | 8 | " | ◯ | CH₃ | Colorless prism-like crystals | 106.5–110 |
| 469 | 5 | Single bond | H | " | " | " | ◯ | —(CH₂)₂CH₃ | Colorless plate-like crystals | 88–90.5 |

EXAMPLE 470

The process of Example 394 is repeated by using a suitable starting material to obtain 6-{3-[N-benzyl-N-(2-3′,4′-dimethoxyphenylethyl)aminocarbonyl]propoxy}-3,4-dihydrocarbostyril. This compound is identified by the following physicochemical properties.

State: Colorless oil

Silica gel thin-layer chromatography: (Silica gel: "Silica-Gel 60 F-254" manufactured by Merck & Co., Inc.); Developing solvent: 8/1 (V/V) a mixture of chloroform-methanol Rf=0.65

Elemental analysis: Calcd. for $C_{30}H_{34}N_2O_5$: C, 71.69%; H, 6.82%; N, 5.57%; Found: C, 71.84%; H, 6.75%; N, 5.29%

Nuclear magnetic resonance spectrum (NMR): $\delta CDCl_3$=1.9–3.1 ppm (10H, m), 3.4 ppm (2H, t), 3.7–4.0 ppm (8H, m), 4.4 ppm (2H, d), 6.4–6.7 ppm (6H, m), 6.9–7.3 ppm (7H, m), 9.3 ppm (1H, br.)

The 6.9–7.3 ppm signal overlaps with the CHCl₃ proton signal.

Infrared absorption spectrum (IR): $\nu_{max}^{film}$ (cm⁻¹)=3220, 3002, 2940, 2840, 1670, 1638, 1595, 1500, 1450, 1360, 1240, 1157, 1013, 960, 850, 800, 740

EXAMPLE 471

3.3 g of 6-{3-[N-methyl-N-(2-methylcyclohexyl)-aminocarbonyl]-2-methylpropoxy}-3,4-dihydrocarbostyril and 3.4 g of 90% DDQ are added to 100 ml of dioxane and this mixture is refluxed for 9.5 hours and then cooled. After the reaction, the solvent is distilled off and the obtained residue is dissolved in chloroform and the organic layer is washed with aqueous saturated NaHCO₃ solution, and with water, dried with anhydrous Na₂SO₄ and then treated with an active charcoal treatment. After distilling off the solvent, the resultant residue is refined by silica gel column chromatography (silica gel: Wakogel C-200; eluent: 10:1 chloroform-methanol (V/V)) and the crude crystals are recrystallized from benzene-ligron to produce 1.2 g of 6-{3-[N-methyl-N-(2-methylcyclohexyl)aminocarbonyl]-2-methylpropoxy}carbostyril in the form of colorless needle-like crystals. Melting point: 146°–149° C.

EXAMPLE 472

To a solution of 2.8 g of 1-methyl-6-[3-(N-methyl-N-cyclohexylaminocarbonyl)propoxy]carbostyril in 50 ml of methanol is added 0.1 g of palladium black, and the mixture is reacted at 50° C. under hydrogen pressure of 2.5 atm. for 8 hours. After the reaction, the catalyst is filtered out and the filtrate is concentrated and evaporated to dryness. The residue is recrystallized from ligroin to obtain 1.9 g of 1-methyl-6-[3-(N-methyl-N-cyclohexylaminocarbonyl)propoxy]-3,4-dihydrocarbostyril in the form of colorless needle-like crystals with melting point of 104.5°–106.5° C.

EXAMPLE 473

To a solution of 1.7 g of 6-[3-(N-cyclohexyl-N-methylaminocarbonyl)propoxy]-3,4-dihydrocarbostyril in 50 ml of DMF is added 0.3 g of sodium hydroxide at room temperature under agitation. After the end of hydrogen generation, 1 ml of methyl iodide is added dropwise to the solution and the mixture is agitated at room temperature for 3 hours. After the reaction, the solvent is distilled off under reduced pressure and the residue is dissolved in 200 ml of chloroform. The chloroform layer is washed with an aqueous K₂CO₃ solution and water and then dried with anhydrous Na₂SO₄. After filtering out the inorganic matter, the mother liquor is concentrated and the residue is recrystallized from ligroin to obtain 0.9 g of 1-methyl-6-[3-(N-cyclohexyl-N-methylaminocarbonyl)propoxy]-3,4-dihydrocarbostyril in the form of colorless needle-like crystals with melting point of 104.5°–106.5° C.

What is claimed is:

1. A compound of the formula,

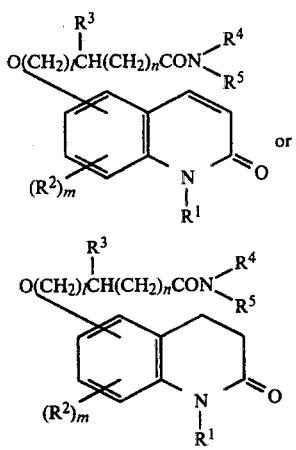

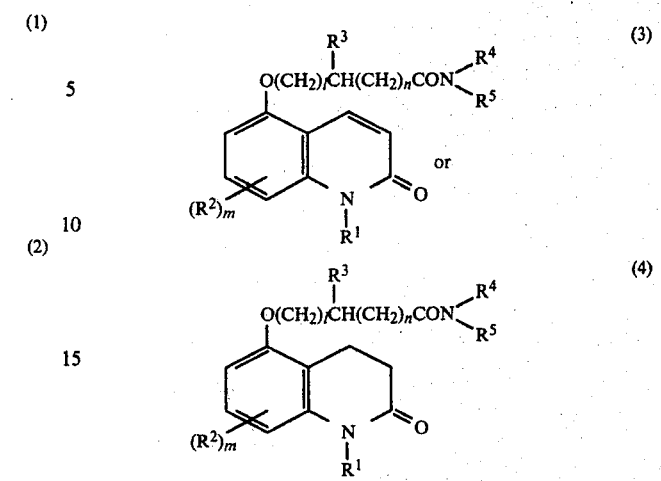

wherein $R^1$ is hydrogen, $C_{1-4}$ alkyl, $C_{2-4}$ alkenyl or phenyl $C_{1-4}$ alkyl; $R^2$ is hydrogen, halogen, hydroxy or phenyl $C_{1-4}$ alkoxy; $R^3$ is hydrogen, hydroxy or $C_{1-4}$ alkyl; $R^4$ is phenyl, $C_{3-8}$ cycloalkyl, $C_{3-8}$ cycloalkyl $C_{1-4}$ alkyl or 2-(3,4-dimethoxyphenyl)ethyl or phenyl or $C_{3-8}$ cycloalkyl substituted by no more than two groups selected from $C_{1-4}$ alkyl, $C_{1-4}$ alkoxy, halogen, $C_{1-4}$ alkanoylamino, $C_{1-4}$ alkanoyloxy, $C_{1-4}$ alkoxycarbonyl, $C_{1-4}$ alkanoyl, $C_{1-4}$ alkylcarbamoyl, $C_{1-4}$ alkylamine, nitro, carboxy, hydroxyl, amninosulfonyl, carbamoyl, and amino; $R^5$ is hydrogen, $C_{1-8}$ alkyl, $C_{2-4}$ alkenyl, phenyl, $C_{3-8}$ cycloalkyl, phenyl $C_{1-4}$ alkyl or $C_{3-8}$ cycloalkyl $C_{1-4}$ alkyl or sustituted phenyl $C_{1-4}$ alkyl substituted in the phenyl group by no more than two $C_{1-4}$ alkoxy groups; m is an integer of 1 to 3; and l and n, which can be the same or different, are 0 or an integer of 1 to 7 such that the sum of l and n does not exceed 7.

2. A compound according to claim 1, wherein $R^4$ is a substituted or an unsubstituted $C_{3-8}$ cycloalkyl group.

3. A compound according to claim 2, wherein $R^5$ is $C_{1-8}$ alkyl.

4. A compound according to claim 2, wherein $R^5$ is $C_{2-4}$ alkenyl.

5. A compound according to claim 2, wherein $R^5$ is phenyl.

6. A compound according to claim 2, wherein $R^5$ is $C_{3-8}$ cycloalkyl.

7. A compound according to claim 2, wherein $R^5$ is a substituted or an unsubstituted phenyl $C_{1-4}$ alkyl group.

8. A compound according to claim 2, wherein $R^5$ is $C_{3-8}$ cycloalkyl $C_{1-4}$ alkyl.

9. A compound according to claim 2, wherein $R^5$ is hydrogen.

10. A compound according to claim 2, wherein $R^1$ is hydrogen.

11. A compound according to claim 2, wherein $R^2$ is hydrogen.

12. A compound according to claim 2, wherein $R^3$ is hydrogen.

13. A compound according to claim 2, of the formula (1).

14. A compound according to claim 2, of the formula,

15. A compound according to claim 14, of the formula (3).

16. A compound according to claim 14, of the formula (4).

17. A compound according to claim 2, of the formula,

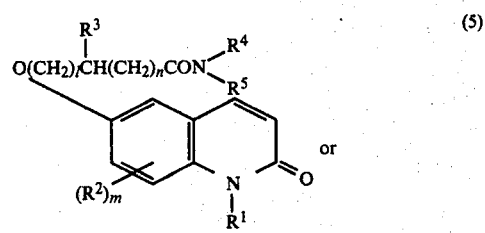

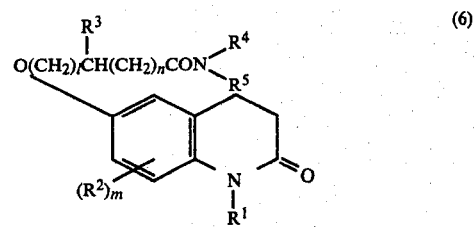

18. A compound according to claim 17, of the formula (5).

19. A compound according to claim 17, of the formula (6).

20. A compound according to claim 3, of the formula,

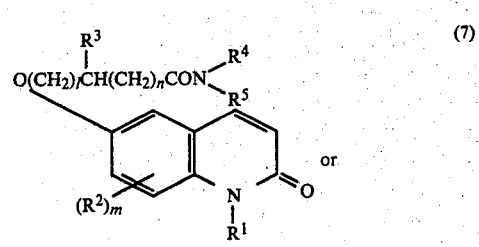

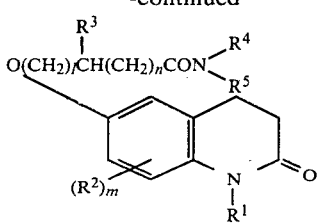
(8)

21. A compound according to claim 20, wherein each of $R_1$, $R_2$ and $R_3$ is hydrogen.

22. A compound according to claim 21, of the formula (7).

23. 6-[3-(N-Methyl-N-cyclohexylaminocarbonyl)-propoxy]-carbostyril.

24. 6-[3-(N-Ethyl-N-cyclohexylaminocarbonyl)-propoxy]-carbostyril.

25. 6-[3-(N-Butyl-N-cyclohexylaminocarbonyl)-propoxy]-carbostyril.

26. 6-[3-(N-Ethyl-N-cyclopropylaminocarbonyl)-propoxy]carbostyril.

27. 6-[3-(N-Ethyl-N-cyclopentylaminocarbonyl)-propoxy]carbostyril.

28. 6-[3-(N-Ethyl-N-cycloheptylaminocarbonyl)-propoxy]carbostyril.

29. 6-[3-(N-Ethyl-N-cyclooctylaminocarbonyl)-propoxy]-carbostyril.

30. 6-[3-(N-Pentyl-N-cyclohexylaminocarbonyl)-propoxy]carbostyril.

31. 6-[3-(N-Hexyl-N-cyclohexylaminocarbonyl)-propoxy]-carbostyril.

32. 6-[3-(N-Octyl-N-cyclohexylaminocarbonyl)-propoxy]-carbostyril.

33. 6-[3-(N-Heptyl-N-cyclohexylaminocarbonyl)-propoxy]carbostyril.

34. 6-[3-(N-Methyl-N-cyclohexylaminocarbonyl)-2-methylpropoxy]carbostyril.

35. 6-{3-[N-(2-3′,4′-Dimethoxyphenylethyl)-N-cyclohexylaminocarbonyl]propoxy}carbostyril.

* * * * *